ns*

(12) United States Patent
Gudas et al.

(10) Patent No.: US 11,160,769 B2
(45) Date of Patent: *Nov. 2, 2021

(54) METHODS OF TREATING METABOLIC SYNDROME RELATED CONDITIONS USING RETINOIC ACID RECEPTOR AGONISTS

(71) Applicant: Cornell University, Ithaca, NY (US)

(72) Inventors: Lorraine J Gudas, New York, NY (US); Yannick Benoit, Ontario (CA); Ronald Perez, Somerset, NJ (US); Xiao-Han Tang, Staten Island, NY (US); Steven Trasino, Brooklyn, NY (US)

(73) Assignee: Cornell University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/112,159

(22) PCT Filed: Jan. 16, 2015

(86) PCT No.: PCT/US2015/011820
§ 371 (c)(1),
(2) Date: Jul. 15, 2016

(87) PCT Pub. No.: WO2015/109231
PCT Pub. Date: Jul. 23, 2015

(65) Prior Publication Data
US 2018/0263924 A1  Sep. 20, 2018

Related U.S. Application Data

(63) Continuation-in-part of application No. PCT/US2014/012083, filed on Jan. 17, 2014.

(60) Provisional application No. 61/990,808, filed on May 9, 2014.

(51) Int. Cl.
*A61K 31/07* (2006.01)
*A61K 45/06* (2006.01)
*A61K 31/426* (2006.01)
*A61K 31/192* (2006.01)
*A61P 1/16* (2006.01)
*A61P 9/00* (2006.01)
*A61P 3/04* (2006.01)
*A61P 3/06* (2006.01)
*A61P 3/10* (2006.01)
*A61P 13/12* (2006.01)

(52) U.S. Cl.
CPC ............ *A61K 31/07* (2013.01); *A61K 31/192* (2013.01); *A61K 31/426* (2013.01); *A61K 45/06* (2013.01); *A61P 1/16* (2018.01); *A61P 3/04* (2018.01); *A61P 3/06* (2018.01); *A61P 3/10* (2018.01); *A61P 9/00* (2018.01); *A61P 13/12* (2018.01)

(58) Field of Classification Search
USPC ........................................................ 514/365
See application file for complete search history.

(56) References Cited

U.S. PATENT DOCUMENTS

| 9,585,857 B2 | 3/2017 | Gudas et al. |
| 10,010,512 B2 | 7/2018 | Gudas et al. |
| 2008/0139842 A1 | 6/2008 | Shudo et al. |
| 2009/0137671 A1 | 5/2009 | Noy |
| 2018/0263924 A1 | 9/2018 | Gudas et al. |
| 2018/0296545 A1 | 10/2018 | Gudas et al. |

FOREIGN PATENT DOCUMENTS

| CA | 2935334 | 7/2014 |
| EP | 0 698 392 | 2/1996 |
| EP | 1224 178 B1 | 8/2003 |
| WO | WO 98/42340 | 10/1998 |
| WO | WO 98/48055 | 10/1998 |
| WO | WO 2005/094333 A2 | 10/2005 |
| WO | WO 2006/108008 | 12/2006 |
| WO | WO 2007/009083 A2 | 1/2007 |
| WO | WO2008/064136 | 5/2008 |
| WO | WO 2011/163183 A2 | 12/2011 |
| WO | WO 2012/162698 | 11/2012 |
| WO | WO 2012/178108 A1 | 12/2012 |
| WO | WO 2014/113695 | 7/2014 |
| WO | WO2015/109231 | 7/2015 |

OTHER PUBLICATIONS

International Search Report for corresponding application No. PCT/US2015/011820 dated May 6, 2015.
Zabali et al. "Effecta of Vitamin A and insulin on the antioxidative state of diabetic rat heart a comparison study with combination tratment" Cell Biochmistry and Function, Jun. 2002, vol. 20 pp. 75-80.

(Continued)

*Primary Examiner* — Kathrien A Cruz
(74) *Attorney, Agent, or Firm* — Mark S. Cohen; Pearl Cohen Zedek Latzer Baratz LLP

(57) ABSTRACT

This invention relates to pharmaceutical compositions and methods for treating (including managing) or preventing metabolic syndrome related conditions using one or more RAR e.g., RAR agonists. Such conditions include, but are not limited to, diseases in pancreas, liver, kidney, testes, muscle, or adipose tissue, as well as other organs that are associated with high fat diet and/or vitamin A deficiency, as well as other conditions associated with abnormal level of triglyceride, cholesterol and/or glucose.

7 Claims, 22 Drawing Sheets
Specification includes a Sequence Listing.

(56) References Cited

OTHER PUBLICATIONS

Abahusain et al. "Retinal, a-tocopherol and carotenolds in diabetes" European Jornal of Clinical Nutrition, Aug. 1999, vol. 53 pp. 630-635 entire document.

Tsin et al "Vitamin A Homeostasis in the Diabetic Rat" Journal of Clinical Biochemistry and Nutrition 1993, vol. 15, pp. 23-31 entire document.

European Search Report for corresponding application No. 15737537.9 dated Sep. 25, 2017.

Lund B W et al: "Discovery of a potent. orally available. and isoform-selective retinoic acid beta2 Receptor Agonist" Journal of Medicinal Chemistry. American Chemical Society.vol. 48. No. 24. Apr. 11, 2005 (Apr. 11, 2005). pp. 7517-7519.

Miwako Ishido et al: "Oral Administration 1.4.6.9 of Synthetic Retinoid Am80 Inhibits the Development of Type 1 Diabetes in X.P A Non-Obese Diabetic (NOD) Mice.". Biological & Pharmaceutical Bulletin Jan 2009. vol. 32. No. 1. Jan. 2009 (Jan. 2009). pp. 157-159. Xp002773750. Issn: 0918-6158.

Douguet D et al: "Quantitative 1-10 Structure-Activity Relationship Studies of Rar Alpha, Beta, Gamma Retinoid Agonists", Quantitative Structure-Activity Relationships, VCH Publishers, Deerfield Beach, Fl, US, vol. 18, No. 2, Jan. 1, 1999 (Jan. 1, 1999), pp. 107-123, XP000957375, ISSN: 0931-8771.

Office Action from corresponding Canadian Application No. 2,937,107 dated Mar. 12, 2018.

Office Action from corresponding Chinese Application No. 201580012615.9 dated Aug. 13, 2018.

Savitha Subramanian "Increased levels of invariant natural killer T lymphocytes worsens metabolic abnormalities and atherosclerosis in obese mice" The abstract, paragraph 2 in the right column on p. 2833 and paragraph 2 in the left column on p. 2835. Journal of Lipid Research, vol. 54 Nov. 30, 2013.

Guariguata L, Whiting D, Weil C, Unwin N. The International Diabetes Federation diabetes atlas methodology for estimating global and national prevalence of diabetes in adults. Diabetes research and clinical practiceDec. 2011;94(3):322-32.

Whiting DR, Guariguata L, Weil C, Shaw J. IDF diabetes atlas: global estimates of the prevalence of diabetes for 2011 and 2030. Diabetes research and clinical practice. [Research Support, Non-U.S. Gov't]. Dec. 2011;94(3):311-21.

Huang ES, Basu A, O'Grady M, Capretta JC. Projecting the future diabetes population size and related costs for the U.S. Diabetes Care. [Research Support, N.I.H., Extramural Research Support, Non-U.S. Gov't]. Dec. 2009;32(12):2225-9.

Oliver-Krasinski JM, Stoffers DA. On the origin of the beta cell. Genes & development. [Research Support, N.I.H., Extramural Review]. Aug. 1, 2008;22(15):1998-2021.

Waldron-Lynch F, Herold KC. Immunomodulatory therapy to preserve pancreatic beta-cell function in type 1 diabetes. Nature reviews Drug discovery. [Review]. Jun. 2011;10(6):429-52.

Waldron-Lynch F, von Herrath M, Herold KC. Towards a curative therapy in type 1 diabetes: remission of autoimmunity, maintenance and augmentation of beta cell mass. Novartis Foundation symposium2008;292:146-55; discussion 55-8, 202-3.

Charbonnel B, Penfornis A, Varroud-Vial M, Kusnik-Joinville O, Detournay B. Insulin therapy for diabetes mellitus: Treatment regimens and associated costs. Diabetes & metabolismDec. 13, 2011.

Soria B, Andreu E, Berná G, Fuentes E, Gil A, León-Quinto T, Martín F, Montanya E, Nadal A, Reig JA, Ripoll C, Roche E, Sanchez-Andrés JV, Segura J. Engineering pancreatic islets. Pflügers Archiv—European Journal of Physiology2000;440(1):1-18.

Zaret KS, Grompe M. Generation and regeneration of cells of the liver and pancreas. Science. [Research Support, N.I.H., Extramural Research Support, Non-U.S. Gov't Review]. Dec. 5, 2008;322(5907):1490-4.

Weir GC, Cavelti-Weder C, Bonner-Weir S. Stem cell approaches for diabetes: towards beta cell replacement. Genome medicine2011;3(9):61.

Sui J, Mehta M, Shi B, Morahan G, Jiang FX. Directed Differentiation of Embryonic Stem Cells Allows Exploration of Novel Transcription Factor Genes for Pancreas Development. Stem cell reviewsJan. 26, 2012;1(1):1-10.

Ben-Yehudah A, White C, Navara CS, Castro CA, Ize-Ludlow D, Shaffer B, Sukhwani M, Mathews CE, Chaillet JR, Witchel SF. Evaluating protocols for embryonic stem cell differentiation into insulin-secreting beta-cells using insulin II-GFP as a specific and noninvasive reporter. Cloning Stem CellsJun. 2009;11(2):245-57.

Blyszczuk P, Czyz J, Kania G, Wagner M, Roll U, St-Onge L, Wobus AM. Expression of Pax4 in embryonic stem cells promotes differentiation of nestin-positive progenitor and insulin-producing cells. Proc Natl Acad Sci U S A. [Research Support, Non-U.S. Gov't]. Feb. 4, 2003;100(3):998-1003.

Borowiak M, Maehr R, Chen S, Chen AE, Tang W, Fox JL, Schreiber SL, Melton DA. Small molecules efficiently direct endodermal differentiation of mouse and human embryonic stem cells. Cell Stem CellApr. 3, 2009;4(4):348-58.

D'Amour KA, Bang AG, Eliazer S, Kelly OG, Agulnick AD, Smart NG, Moorman MA, Kroon E, Carpenter MK, Baetge EE. Production of pancreatic hormone-expressing endocrine cells from human embryonic stem cells. Nat Biotechnol. [Research Support, Non-U.S. Gov't]. Nov. 2006;24(11):1392-401.

Kroon E, Martinson LA, Kadoya K, Bang AG, Kelly OG, Eliazer S, Young H, Richardson M, Smart NG, Cunningham J, Agulnick AD, D'Amour KA, Carpenter MK, Baetge EE. Pancreatic endoderm derived from human embryonic stem cells generates glucose-responsive insulin-secreting cells in vivo. Nat BiotechnolApr. 2008;26(4):443-52.

Micallef SJ, Janes ME, Knezevic K, Davis RP, Elefanty AG, Stanley EG. Retinoic acid induces Pdx1-positive endoderm in differentiating mouse embryonic stem cells. DiabetesFeb. 2005;54(2):301-5.

Laursen KB, Wong PM, Gudas LJ. Epigenetic regulation by RARalpha maintains ligand-independent transcriptional activity. Nucleic acids researchJan. 2012;40(1):102-15.

Jaramillo M, Banerjee I. Endothelial cell co-culture mediates maturation of human embryonic stem cell to pancreatic insulin producing cells in a directed differentiation approach. J Vis Exp2012(61).

Chen Y, Pan FC, Brandes N, Afelik S, Solter M, Pieler T. Retinoic acid signaling is essential for pancreas development and promotes endocrine at the expense of exocrine cell differentiation in Xenopus. Developmental biology. [Comparative Study Research Support, Non-U.S. Gov't]. Jul. 1, 2004;271(1):144-60.

Ostrom M, Loffler KA, Edfalk S, Selander L, Dahl U, Ricordi C, Jeon J, Correa-Medina M, Diez J, Edlund H. Retinoic acid promotes the generation of pancreatic endocrine progenitor cells and their further differentiation into beta-cells. PLoS One. [Research Support, Non-U.S. Gov't]. 2008;3(7):e2841.

Matthews KA, Rhoten WB, Driscoll HK, Chertow BS. Vitamin A deficiency impairs fetal islet development and causes subsequent glucose intolerance in adult rats. The Journal of nutrition. [Research Support, U.S. Gov't, P.H.S.]. Aug. 2004;134(8):1958-63.

Chertow BS, Blaner WS, Baranetsky NG, Sivitz WI, Cordle MB, Thompson D, Meda P. Effects of vitamin A deficiency and repletion on rat insulin secretion in vivo and in vitro from isolated islets. J Clin Invest. [In Vitro Research Support, Non-U.S. Gov't Research Support, U.S. Gov't, P.H.S.]. Jan. 1987;79(1):163-9.

Dodge R, Loomans C, Sharma A, Bonner-Weir S. Developmental pathways during in vitro progression of human islet neogenesis. Differentiation. [Research Support, N.I.H., Extramural Research Support, Non-U.S. Gov't]. Feb. 2009;77(2):135-47.

Dolle P, Ruberte E, Leroy P, Morriss-Kay G, Chambon P. Retinoic acid receptors and cellular retinoid binding proteins. I. A systematic study of their differential pattern of transcription during mouse organogenesis. Development. [Research Support, Non-U.S. Gov't]. Dec. 1990;110(4):1133-51.

Ghyselinck NB, Dupe V, Dierich A, Messaddeq N, Garnier JM, Rochette-Egly C, Chambon P, Mark M. Role of the retinoic acid receptor beta (RARβ) during mouse development. The International journal of developmental biology. [Research Support, Non-U.S. Gov't Research Support, U.S. Gov't, P.H.S.]. Jun. 1997;41(3):425-47.

(56) References Cited

OTHER PUBLICATIONS

Martinez-Ceballos E, Gudas LJ. Hoxa1 is required for the retinoic acid-induced differentiation of embryonic stem cells into neurons. Journal of neuroscience research. [Research Support, N.I.H., Extramural]. Oct. 2008;86(13):2809-19.

Martinez-Ceballos E, Chambon P, Gudas LJ. Differences in gene expression between wild type and Hoxa1 knockout embryonic stem cells after retinoic acid treatment or leukemia inhibitory factor (LIF) removal. The Journal of biological chemistry. [Research Support, N.I.H., Extramural Research Support, U.S. Gov't, P.H.S.]. Apr. 22, 2005;280(16):16484-98.

Benoit YD, Lussier C, Ducharme PA, Sivret S, Schnapp LM, Basora N, Beaulieu JF. Integrin alpha8beta1 regulates adhesion, migration and proliferation of human intestinal crypt cells via a predominant RhoA/ROCK-dependent mechanism. Biology of the cell / under the auspices of the European Cell Biology Organization. [Research Support, Non-U.S. Gov't]. Dec. 2009;101(12):695-708.

Auclair BA, Benoit YD, Rivard N, Mishina Y, Perreault N. Bone morphogenetic protein signaling is essential for terminal differentiation of the intestinal secretory cell lineage. GastroenterologySep. 2007;133(3):887-96.

Yoshino J, Mills KF, Yoon MJ, Imai S. Nicotinamide mononucleotide, a key NAD(+) intermediate, treats the pathophysiology of diet- and age-induced diabetes in mice. Cell MetabOct. 5, 2011;14(4):528-36.

Spokoini R, Kfir-Erenfeld S, Yefenof E, Sionov RV. Glycogen synthase kinase-3 plays a central role in mediating glucocorticoid-induced apoptosis. Mol EndocrinolJun. 2010;24(6):1136-50.

Yamaguchi TP, Takada S, Yoshikawa Y, Wu N, McMahon AP. T (Brachyury) is a direct target of Wnt3a during paraxial mesoderm specification. Genes & developmentDec. 15, 1999;13(24):3185-90.

Otonkoski T, Beattie GM, Mally MI, Ricordi C, Hayek A. Nicotinamide is a potent inducer of endocrine differentiation in cultured human fetal pancreatic cells. J Clin InvestSep. 1993;92(3):1459-66.

Lumelsky N, Blondel O, Laeng P, Velasco I, Ravin R, McKay R. Differentiation of embryonic stem cells to insulin-secreting structures similar to pancreatic islets. Science. [Research Support, Non-U.S. Gov't]. May 18, 2001;292(5520):1389-94.

Marchand M, Schroeder IS, Markossian S, Skoudy A, Negre D, Cosset FL, Real P, Kaiser C, Wobus AM, Savatier P. Mouse ES cells over-expressing the transcription factor NeuroD1 show increased differentiation towards endocrine lineages and insulin-expressing cells. The International journal of developmental biology. [Research Support, Non-U.S. Gov't]. 2009;53(4):569-78.

Langton S, Gudas LJ. CYP26A1 knockout embryonic stem cells exhibit reduced differentiation and growth arrest in response to retinoic acid. Developmental biology. [Research Support, N.I.H., Extramural Research Support, U.S. Gov't, Non-P.H.S.]. Mar. 15, 2008;315(2):331-54.

Soria B. In-vitro differentiation of pancreatic beta-cells. DifferentiationOct. 2001;68(4-5):205-19.

Van Hoof D, D'Amour KA, German MS. Derivation of insulin-producing cells from human embryonic stem cells. Stem cell research. [Research Support, Non-U.S. Gov't Review]. Sep.-Nov. 2009;3(2-3):73-87.

Bernardo AS, Hay CW, Docherty K. Pancreatic transcription factors and their role in the birth, life and survival of the pancreatic beta cell. Mol Cell EndocrinolNov. 6, 2008;294(1-2):1-9.

Kashyap V, Rezende NC, Scotland KB, Shaffer SM, Persson JL, Gudas LJ, Mongan NP. Regulation of stem cell pluripotency and differentiation involves a mutual regulatory circuit of the NANOG, OCT4, and SOX2 pluripotency transcription factors with polycomb repressive complexes and stem cell microRNAs. Stem cells and developmentSep. 2009;18(7):1093-108.

Rukstalis JM, Habener JF. Neurogenin3: a master regulator of pancreatic islet differentiation and regeneration. IsletsNov.-Dec. 2009;1(3):177-84.

Gosmain Y, Katz LS, Masson MH, Cheyssac C, Poisson C, Philippe J. Pax6 is crucial for beta-cell function, insulin biosynthesis, and glucose-induced insulin secretion. Mol Endocrinol. [Research Support, Non-U.S. Gov't]. Apr. 2012;26(4):696-709.

Ahlgren U, Pfaff SL, Jessell TM, Edlund T, Edlund H. Independent requirement for ISL1 in formation of pancreatic mesenchyme and islet cells. Nature. [Research Support, Non-U.S. Gov't]. Jan. 16, 1997;385(6613):257-60.

Naujok O, Francini F, Picton S, Bailey CJ, Lenzen S, Jorns A. Changes in gene expression and morphology of mouse embryonic stem cells on differentiation into insulin-producing cells in vitro and in vivo. Diabetes Metab Res RevJul. 2009;25(5):464-76.

Gasa R, Mrejen C, Leachman N, Otten M, Barnes M, Wang J, Chakrabarti S, Mirmira R, German M. Proendocrine genes coordinate the pancreatic islet differentiation program in vitro. Proc Natl Acad Sci U S ASep. 7, 2004;101(36):13245-50.

Steiner DF, Cunningham D, Spigelman L, Aten B. Insulin biosynthesis: evidence for a precursor. ScienceAug. 11, 1967;157(3789):697-700.

Daly ME, Vale C, Walker M, Littlefield A, Alberti KG, Mathers JC. Acute effects on insulin sensitivity and diurnal metabolic profiles of a high-sucrose compared with a high-starch diet. Am J Clin NutrJun. 1998;67(6):1186-96.

Cryer PE, Axelrod L, Grossman AB, Heller SR, Montori VM, Seaquist ER, Service FJ. Evaluation and management of adult hypoglycemic disorders: an Endocrine Society Clinical Practice Guideline. The Journal of clinical endocrinology and metabolismMar. 2009;94(3):709-28.

Cai J, Yu C, Liu Y, Chen S, Guo Y, Yong J, Lu W, Ding M, Deng H. Generation of homogeneous PDX1(+) pancreatic progenitors from human ES cell-derived endoderm cells. J Mol Cell Biol. [Research Support, Non-U.S. Gov't]. Feb. 2010;2(1):50-60.

Jonsson J, Carlsson L, Edlund T, Edlund H. Insulin-promoter-factor 1 is required for pancreas development in mice. NatureOct. 13, 1994;371(6498):606-9.

Fujimoto K, Polonsky KS. Pdx1 and other factors that regulate pancreatic beta-cell survival. Diabetes, obesity & metabolismNov. 2009;11 Suppl 4:30-7.

Dalgin G, Ward AB, Hao le T, Beattie CE, Nechiporuk A, Prince VE. Zebrafish mnx1 controls cell fate choice in the developing endocrine pancreas. DevelopmentNov. 2011;138(21):4597-608.

Vetere A, Marsich E, Di Piazza M, Koncan R, Micali F, Paoletti S. Neurogenin3 triggers beta-cell differentiation of retinoic acid-derived endoderm cells. The Biochemical journalMay 1, 2003;371(Pt 3):831-41.

Dohrmann C, Gruss P, Lemaire L. Pax genes and the differentiation of hormone producing endocrine cells in the pancreas. Mech DevMar. 15, 2000;92(1):47-54.

American Diabetes A. Diagnosis and classification of diabetes mellitus. Diabetes CareJan. 2005;28 Suppl 1:S37-42.

Del Prato S, Marchetti P. Beta- and alpha-cell dysfunction in type 2 diabetes. Horm Metab ResNov.-Dec. 2004;36(11-12):775-81.

Riserus U, Willett WC, Hu FB. Dietary fats and prevention of type 2 diabetes. Prog Lipid ResJan. 2009;48(1):44-51.

Sirchia SM, Ren M, Pili R, Sironi E, Somenzi G, Ghidoni R, Toma S, Nicolo G, Sacchi N. Endogenous reactivation of the RARβ2 tumor suppressor gene epigenetically silenced in breast cancer. Cancer researchMay 1, 2002;62(9):2455-61.

Youssef EM, Estecio MR, Issa JP. Methylation and regulation of expression of different retinoic acid receptor beta isoforms in human colon cancer. Cancer Biol TherJan. 2004;3(1):82-6.

House MG, Herman JG, Guo MZ, Hooker CM, Schulick RD, Lillemoe KD, Cameron JL, Hruban RH, Maitra A, Yeo CJ. Aberrant hypermethylation of tumor suppressor genes in pancreatic endocrine neoplasms. Ann SurgSep. 2003;238(3):423-31; discussion 31-2.

Sato N, Fukushima N, Hruban RH, Goggins M. CpG island methylation profile of pancreatic intraepithelial neoplasia. Mod PatholMar. 2008;21(3):238-44.

Volkmar M, Dedeurwaerder S, Cunha DA, Ndlovu MN, Defrance M, Deplus R, Calonne E, Volkmar U, Igoillo-Esteve M, Naamane N, Del Guerra S, Masini M, Bugliani M, Marchetti P, Cnop M, Eizirik DL, Fuks F. DNA methylation profiling identifies epigenetic dysregulation in pancreatic islets from type 2 diabetic patients. EMBO JMar. 21, 2012;31(6):1405-26.

Lund, B. W.; Piu, F.; Gauthier, N. K.; Eeg, A.; Currier, E.; Sherbukhin,V.; Brann, M. R.; Hacksell, U.; Olsson, R. Discovery of a Potent,Orally

(56) References Cited

OTHER PUBLICATIONS

Available, and Isoform-Selective Retinoic Acid beta2 Receptor Agonist. J. Med. Chem. 2005, 48, 7517-7519.
Vivat-Hannah V et al, Synergistic Cytotoxicity Exhibited by Combination Treatment of Selective Retinoid Ligands with Taxol (Paclitaxel). Cancer Res. 2001, 61, 8703-8711.
Millikan LE, Adapalene: an update on newer comparative studies between the various retinoids. Int.J.Dermatol..2000, 39, 784-88.
Chen JY et al (1995) RAR-specific agonist/antagonists which dissociate transactivation and AP1 transrepression inhibit anchorage-independent cell proliferation. EMBO J. 1995, 14, 1187-97.
Lazo M, Hernaez R, Eberhardt MS, Bonekamp S, Kamel I, Guallar E, Koteish A, Brancati FL, Clark JM.Prevalence of nonalcoholic fatty liver disease in the United States: the Third National Health and Nutrition Examination Survey, 1988-1994. Am J Epidemiol. 2013; 1:38-45.
Loomba R, Sanyal AJ. The global NAFLD epidemic. Nat Rev Gastroenterol Hepatol. 2013; 11:686-90.
Baffy G, Brunt EM, Caldwell SH.Hepatocellular carcinoma in non-alcoholic fatty liver disease: an emerging menace. J Hepatol. 2012;6:1384-91.
Reeves HL, Friedman SL. Activation of hepatic stellate cells—a key issue in liver fibrosis. Front Biosci. 2002;7:808-26.
Puche JE, Saiman Y, Friedman SL. Hepatic stellate cells and liver fibrosis. Compr Physiol. 2013;4):1473-92.
Geerts, A. History, heterogeneity, developmental biology, and functions of quiescent hepatic stellate cells. Semin. Liver Dis. 2001;21:311-335.
Brun PJ, Yang KJ, Lee SJ, Yuen JJ, Blaner WS. Retinoids: Potent regulators of metabolism. Biofactors. 2013 2):151-63.
(CDC) CfDCaP. Vital signs: prevalence, treatment, and control of high levels of low-density lipoprotein cholesterol—United States, 1999-2002 and 2005-200. MMWR Morb Mortal Wkly Rep. 2011;60(4):109-14. PubMed PMID: 21293326.
Martin SS, Abd TT, Jones SR, Michos ED, Blumenthal RS, Blaha MJ. 2013 American Cholesterol Treatment Guideline: What Was Done Well and What Could Be Done Better. J Am Coll Cardiol. 2014. doi: 10.1016/j.jacc.2014.02.578. PubMed PMID: 24681146.
Mampuya WM, Frid D, Rocco M, Huang J, Brennan DM, Hazen SL, Cho L. Treatment strategies in patients with statin intolerance: the Cleveland Clinic experience. Am Heart J. 2013;166(3):597-603. doi: 10.1016/j.ahj.2013.06.004. PubMed PMID: 24016512.
Tang XH, Gudas LJ. Retinoids, retinoic acid receptors, and cancer. Annu Rev Pathol. 2011;6:345-64. doi: 10.1146/annurev-pathol-011110-130303. PubMed PMID: 21073338.
Baldwin HE, Nighland M, Kendall C, Mays DA, Grossman R, Newburger J. 40 years of topical tretinoin use in review. J Drugs Dermatol. 2013;12(6):638-42. PubMed PMID: 23839179.
Ellis CN, Swanson NA, Grekin RC, Goldstein NG, Bassett DR, Anderson TF, Voorhees JJ. Etretinate therapy causes increases in lipid levels in patients with psoriasis. Arch Dermatol. 1982;118(8):559-62. PubMed PMID: 7103524.
Lyons F, Laker MF, Marsden JR, Manuel R, Shuster S. Effect of oral 13-cis-retinoic acid on serum lipids. Br J Dermatol. 1982;107(5):591-5. PubMed PMID: 6215057.
Marsden J. Hyperlipidaemia due to isotretinoin and etretinate: possible mechanisms and consequences. Br J Dermatol. 1986;114(4):401-7. PubMed PMID: 3516195.
Barth JH, Macdonald-Hull SP, Mark J, Jones RG, Cunliffe WJ. Isotretinoin therapy for acne vulgaris: a re-evaluation of the need for measurements of plasma lipids and liver function tests. Br J Dermatol. 1993;129(6):704-7. PubMed PMID: 8286255.
Amengual J, Ribot J, Bonet ML, Palou A. Retinoic acid treatment enhances lipid oxidation and inhibits lipid biosynthesis capacities in the liver of mice. Cell Physiol Biochem. 2010;25(6):657-66. doi: 10.1159/000315085. PubMed PMID: 20511711.
Kim SC, Kim CK, Axe D, Cook A, Lee M, Li T, Smallwood N, Chiang JY, Hardwick JP, Moore DD, Lee YK. All-trans-retinoic acid ameliorates hepatic steatosis in mice by a novel transcriptional cascade. Hepatology. 2013. doi: 10.1002/hep.26699. PubMed PMID: 24038081.
Thacher SM, Vasudevan J, Chandraratna RA. Therapeutic applications for ligands of retinoid receptors. Curr Pharm Des. 2000;6(1):25-58. PubMed PMID: 10637371.
Laursen KB, Mongan NP, Zhuang Y, Ng MM, Benoit YD, Gudas LJ. Polycomb recruitment attenuates retinoic acid-induced transcription of the bivalent NR2F1 gene. Nucleic Acids Res. 2013;41(13):6430-43. doi: 10.1093/nar/gkt367. PubMed PMID: 23666625.
Buchovercky CM, Turley SD, Brown HM, Kyle SM, McDonald JG, Liu B, Pieper AA, Huang W, Katz DB, Russell DW, Shendure J, Justice MY. A suppressor screen in Mecp2 mutant mice implicates cholesterol metabolism in Rett syndrome. Nature Genetics. Sep;45(9):1013-20; Epub Jul. 28, 2013.
Justice, MJ, Public Research Seminar (A genetic suppressor screen in mice reveals that lipid metabolism is a therapeutic target for Rett Syndrome) at Sloan Kettering Institute, May 1, 2014.
Examination Report of Canadian Application No. 2,937,107 dated Dec. 28, 2018.

METHODS OF TREATING METABOLIC SYNDROME RELATED CONDITIONS USING RETINOIC ACID RECEPTOR AGONISTS

CROSS-REFERENCE TO RELATED APPLICATIONS

This application is a National Phase Application of PCT International Application PCT/US15/11820, filed. Jan. 16, 2015, which claims priority to PCT Patent Application PCT/US14/12083, filed Jan. 17, 2014, and also claims priority to and the benefit of U.S. Provisional Application 61/990,808, filed May 9, 2014. All applications above are incorporated herein in their entirety.

GOVERNMENT FUNDING

This invention was made with Government support under Grant Numbers DE010389 and CA043796 awarded by the National Institutes of Health. The United States Government has certain rights in the invention.

FIELD

The invention relates to the treatment or prevention of certain metabolic syndrome related conditions. For example, the invention relates to controlling the level cholesterol, triglyceride, and/or glucose in a subject in need thereof, as well as treating or preventing diseases or conditions caused by fat accumulation or vitamin A deficiency in a subject in need thereof.

BACKGROUND

Metabolic syndrome is caused by a cluster of metabolic risk factors which include, but are not limited to, insulin resistance, hypertension (high blood pressure), cholesterol abnormalities, and an increased risk for blood clotting. Examples of metabolic syndrome related conditions include vitamin deficiencies, diabetes, fatty liver, high blood pressure, insulin resistance, obesity, abnormal cholesterol and/or triglyceride levels, artery and heart diseases.

After smoking, high fat diet is said to be the second most lethal habit, causing 300,000 deaths each year in the U.S. alone. High fat diet leads to many health problems, including obesity, stroke, cancer, high blood pressure, diabetes, osteoarthritis, rheumatoid arthritis, multiple sclerosis, heart disease, and diseases in other organs such as liver and kidney.

Diabetes is a group of diseases characterized by high blood glucose levels that result from defects in the body's ability to produce and/or use insulin. In 2011 there were an estimated 366 million cases of diabetes worldwide, according to the International Diabetes Federation, and these cases are estimated to increase to 522 million by 2030 (1, 2). In the U.S. there were 23.7 million diagnosed cases, with an estimated healthcare cost of $113 billion (2, 3). Type II diabetes results when insulin-directed metabolism of glucose is impaired in peripheral tissues such as fat and muscle, and production of insulin by pancreatic β-cells cannot meet metabolic demands due to loss of β-cell number and function (4). In type I diabetes, auto-immune destruction of insulin-producing pancreatic β-cells gives rise to hyperglycemia (5). Each year in the United States there are over 30,000 new cases of type I diabetes diagnosed (6). Patients with type I diabetes can control their blood glucose level with insulin supplements (7). However, the differentiation of stem cells into pancreatic β-cells could be a long term, better solution (8-10).

Type II diabetes is more common. In early stages of type II diabetes the body does not use insulin properly, a phenomenon known as insulin resistance. In response to insulin resistance the pancreas will make extra insulin to make up for it. But over time there won't be enough insulin to keep blood glucose at normal levels because insulin-producing pancreatic β-cells will fail to cope with increasing demand leading to their destruction and decreased function. Type II diabetes is an increasingly prevalent disease that due to a high frequency of complications leads to a significant reduction of life expectancy. Because of diabetes associated microvascular complications, type II diabetes is currently the most frequent cause of adult-onset loss of vision, renal failure, and amputations in the industrialized world. In addition, the presence of type II diabetes is associated with a two to five fold increase in cardiovascular disease risk. After long duration of disease, most patients with type II diabetes will eventually fail on oral therapy and become insulin dependent with the necessity for daily injections and multiple daily glucose measurements.

A third type of diabetes, gestational diabetes, is developed by many women usually around the 24th week of pregnancy. Treatment for gestational diabetes aims to keep blood glucose levels equal to those of pregnant women who don't have gestational diabetes.

Some patients with diabetes can manage their conditions with healthy eating and exercise. Some will need to have prescribed medications and/or insulin to keep blood glucose levels. In addition, diabetes is a progressive disease. Even if medication is not required at first, it may be needed overtime.

Non-alcoholic fatty liver disease (NAFLD) is marked by lipid accumulation in hepatocytes (steatosis) without evidence of hepatitis or liver fibrosis (69, 70). NAFLD is a major risk factor for development of non-alcohol steatohepatitis (NASH) and hepatocellular carcinoma (71). Driven by rising rates of obesity, diabetes and insulin resistance, NAFLD is currently the most common form of liver disease in the United States with an estimated 55 million cases (69). At the current rate, NAFLD will reach epidemic proportions in the United States by 2030; yet no FDA approved pharmacological therapy exist for prevention or treatment of NAFLD (69).

Over the last decade, experimental animal and human data suggests that hepatic stellate cells (HSCs) are an important cellular target for development of pharmacological therapies for prevention or treatment of NAFLD spectrum liver diseases (73). HSCs are star-like cells that reside in the liver sinusoids whose main function are to store 80-90% of the total body vitamin A (VA) pool (74). During hepatic injury HSCs losing their VA storage capacity, trans-differentiate into myofibroblasts and orchestrate wound healing by secreting components of extra-cellular matrix including type 1 collagen (colla1) and alpha-smooth muscle actin (α-SMA) (72, 73). During pathogenesis of unchecked NAFLD, HSCs proliferate and become highly fibrotic through hyper-secretion colla1 and α-SMA leading to liver scarring and an inflammation cascade that drives further hepatic fibrosis and liver damage (72,73).

Diabetes is the most common cause of kidney failure, accounting for nearly 44 percent of new cases. Even when diabetes is controlled, the disease can lead to Chronic Kidney Disease (CKD) and kidney failure. Nearly 24 million people in the United States have diabetes, and nearly 180,000 people are living with kidney failure as a result of diabetes. People with kidney failure undergo either dialysis, an artificial blood-cleaning process, or transplantation to receive a healthy kidney from a donor. In 2005, care for patients with kidney failure cost the United States nearly $32 billion.

Triglycerides are composed of glycerol and various fatty acids, which are used to store energy and provide energy to muscles. Triglycerides are the end product of digesting and breaking down fats in meals, but some triglycerides are made in the body from other energy sources such as carbohydrates. Normally only small amounts are found in the blood. Extra triglycerides are stored in different places of the body in case they are needed later. High blood triglyceride levels (e.g., as in hypertriglyceridemia) have been linked to obesity, diabetes, and a greater chance for heart disease.

Cholesterol is a sterol, one of three major classes of lipids which all animal cells make and utilize to construct their membranes. It is also the precursor of the steroid hormones, bile acids and vitamin D. Since cholesterol is insoluble in water, it is transported in the blood plasma within protein particles (lipoproteins). Elevated serum cholesterol levels are a major risk factor for development of atherosclerosis, myocardial infarction, and ischemic stroke. Approximately 71 million American adults have significantly elevated cholesterol levels, and among these adults only 1 out of 3 have this condition under control ((CDC) CfDCaP., 2011, MMWR Morb Mortal Wkly Rep. 60(4): 109-14).

In view of the health risks, the American Heart Association recommends that everyone over the age of 20 should get a lipid panel test to measure cholesterol and triglycerides at least every five years. A healthy diet and exercise plan can lower triglyceride levels, improve cholesterol, and lower the risk of heart disease and other hypertriglyceridemia or hypercholesterolemia-associated diseases. It takes time for participants to lose body weight and improve their plasma triglyceride and cholesterol levels. Often even after these levels are normalized, the great majority of participants regain body weight and fall back to the previous hyperlipidemia and hypercholesterolemia conditions when followed for 3-5 years. In certain conditions, such as familial hypercholesterolemia, medication or even surgery is required.

Drugs useful for the treatment of hypertriglyceridemia include fat absorption inhibitors that block pancreatic triglyceride lipase in the intestine, thermogenic agents that increase basal metabolism rate, as well as anorectics that suppress appetite. Drugs useful for the treatment of hypercholesterolemia include inhibitors for cholesterol biosynthesis (statins), cholesterol absorption inhibitors, bile acid sequestrants, fibric acid derivatives and high doses (3-6 g/day) of niacin. Each of these drugs has its therapeutic limitations, and severe side-effects have been reported for some drugs. Current lipid lowering therapies do not sufficiently address the high triglyceride and cholesterol levels that are now known to be an important risk factor for cardiovascular disease without unwanted side effects.

Despite of multiple drugs under investigation, the health risks associated with high triglyceride and cholesterol levels are actually increasing. A new guideline was recently issued by the American College of Cardiology and the American Heart Association (ACC-AHA). This new guideline would increase the number of U.S. adults receiving or eligible for cholesterol control therapy from 43.2 million (37.5%) to 56.0 million (48.6%), with most of this increase in numbers (10.4 million of 12.8 million) would occur among adults who are without cardiovascular disease but would be classified solely on the basis of their 10-year risk of a cardiovascular event (Pencina et al., 2014, N. Engl. J. Med. 370 (15): 1422-1431). In addition, more than 50 million Americans are currently prescribed statins, but up to 20% of adults with elevated cholesterol are unable to use statins due to side effects such as muscle achiness and weakness (Mampuya et al., 2013, Am Heart J., 166(3): 597-603. doi: 10.1016/j.ahj.2013.06.004).

Retinoids are structurally related to vitamin A (VA) and are used to treat dermatological disorders and some cancers (Tang et al., 2011, Annu Rev Pathol., 6:345-64. doi: 10.1146/annurev-pathol-011110-130303; Baldwin et al., 2013, J Drugs Dermatol., 12(6): 638-42. PubMed PMID: 23839179). Previously, numerous studies have demonstrated that a common side effect of retinoid administration to humans and rodents is both hypertriglyceridemia and hypercholesterolemia (Ellis et al., 1982, Arch Dermatol., 118(8): 559-62; Lyons et al., 1982, Br J Dermatol., 107(5): 591-5; Marsden J., 1986, Br J Dermatol., 114(4): 401-7; Barth et al., 1993, Br J Dermatol., 129(6): 704-7). Although elevated serum lipid profiles of subjects on retinoid therapy revert back to baseline levels upon cessation of treatment, these observations have raised concern that retinoid (RA) therapy could increase risk for cardiovascular disease (Marsden J., 1986, Br J Dermatol., 114(4): 401-7). Standeven et al. (1996, Fundamental and Applied Toxicology 33, 264-271) reported that retinoic acid receptors mediate retinoid-induced hypertriglyceridemia in rats.

There is an unmet medical need for methods, medicaments and pharmaceutical compositions to treat (including managing) the above metabolic syndrome related conditions, particularly with regard to treatments having disease-modifying properties, rapid impact, and at the same time showing a good safety profile. The present invention provides compositions and methods to meet the unmet medical needs.

SUMMARY

This invention discloses pharmaceutical compositions and methods for treating (including managing) or preventing metabolic syndrome related conditions. Such conditions include, but are not limited to, diseases in pancreas, liver, kidney, testes, muscle, or adipose tissue, as well as other organs that are associated with high fat diet and/or vitamin A deficiency, as well as other conditions associated with abnormal level of triglyceride, cholesterol and/or glucose.

According to certain embodiments, the invention provides a method of treating or preventing a disease in a subject in need thereof comprising administering to the subject vitamin A or a retinoic acid receptor-beta (RARβ) agonist, where the disease is selected from the group consisting of diabetes, a cardiovascular disease, a liver disease, a kidney disease, obesity, hyperlipidemia, hypertriglyceridemia, or hyperglycemia.

According to certain embodiments, the invention provides a method of treating or preventing a pancreatic disease in a subject in need thereof comprising administering to the subject vitamin A or a retinoic acid receptor-beta (RARβ) agonist.

In certain embodiments, the pancreatic disease is associated with obesity.

In certain embodiments, the pancreatic disease is associated with a high fat diet.

In certain embodiments, the pancreatic disease is associated with vitamin A deficiency in the pancreas.

The pancreatic disease may be diabetes, which may be type I or type II diabetes, or gestational diabetes.

According to certain embodiments, the invention provides a method of increasing RARβ level in a subject in need thereof comprising administering to the subject vitamin A or a retinoic acid receptor-beta (RARβ) agonist.

In certain embodiments, RARβ level is increased in an organ.

The organ may be pancreas, liver, kidney, testes, muscle, or adipose tissue.

According to certain embodiments, the invention provides a method of treating or preventing the degeneration of pancreatic beta cells in a subject in need thereof comprising administering to the subject vitamin A or a retinoic acid receptor-beta (RARβ) agonist.

According to certain embodiments, the invention provides a method of maintaining or improving the function of pancreatic beta cells in a subject in need thereof comprising administering to the subject vitamin A or a retinoic acid receptor-beta (RARβ) agonist.

According to certain embodiments, the invention provides a method of controlling insulin secretion in a subject in need thereof comprising administering to the subject vitamin A or a retinoic acid receptor-beta (RARβ) agonist.

According to certain embodiments, the invention provides a method of maintaining or improving pancreatic insulin secretion in a subject in need thereof comprising administering to the subject vitamin A or a retinoic acid receptor-beta (RARβ) agonist.

According to certain embodiments, the invention provides a method of controlling insulin sensitivity in a subject in need thereof comprising administering to the subject vitamin A or a retinoic acid receptor-beta (RARβ) agonist.

According to certain embodiments, the invention provides a method of maintaining or improving insulin sensitivity in a subject in need thereof comprising administering to the subject vitamin A or a retinoic acid receptor-beta (RARβ) agonist.

According to certain embodiments, the invention provides a method of controlling insulin metabolism in a subject in need thereof comprising administering to the subject vitamin A or a retinoic acid receptor-beta (RARβ) agonist.

According to certain embodiments, the invention provides a method of maintaining or improving insulin metabolism in a subject in need thereof comprising administering to the subject vitamin A or a retinoic acid receptor-beta (RARβ) agonist.

According to certain embodiments, the invention provides a method of controlling insulin resistance in a subject in need thereof comprising administering to the subject vitamin A or a retinoic acid receptor-beta (RARβ) agonist.

Vitamin A or a retinoic acid receptor-beta (RARβ) agonist may simultaneously control insulin resistance and insulin secretion according to one embodiment of the invention. As such, the number of large pancreatic islets and/or pancreatic insulin content may be reduced in the subject in need thereof.

According to certain embodiments, the invention provides a method of controlling the level of glucagon in a subject in need thereof comprising administering to said subject vitamin A or a retinoic acid receptor-beta (RARβ) agonist.

According to certain embodiments, the invention provides a method of maintaining or improving the level of glucagon in a subject in need thereof comprising administering to said subject vitamin A or a retinoic acid receptor-beta (RARβ) agonist.

According to certain embodiments, the invention provides a method of treating or preventing fat deposit of a subject in need thereof comprising administering to the subject vitamin A or a retinoic acid receptor-beta (RARβ) agonist.

According to certain embodiments, the invention provides a method of controlling body weight in a subject in need thereof comprising administering to the subject vitamin A or a retinoic acid receptor-beta (RARβ) agonist.

According to certain embodiments, the invention provides a method of controlling inflammation of a subject in need thereof comprising administering to the subject vitamin A or a retinoic acid receptor-beta (RARβ) agonist.

According to certain embodiments, the invention provides a method of treating or preventing inflammation of a subject in need thereof comprising administering to the subject vitamin A or a retinoic acid receptor-beta (RARβ) agonist.

According to certain embodiments, the invention provides a method of decreasing the level of an inflammatory mediator in a subject in need thereof comprising administering to the subject vitamin A or a retinoic acid receptor-beta (RARβ) agonist.

According to certain embodiments, the invention provides a method of controlling oxidative stress in a subject in need thereof comprising administering to the subject vitamin A or a retinoic acid receptor-beta (RARβ) agonist.

According to certain embodiments, the invention provides a method of decreasing oxidative stress in a subject in need thereof comprising administering to the subject vitamin A or a retinoic acid receptor-beta (RARβ) agonist.

In certain embodiments, the production of the inflammatory mediator is decreased.

In certain embodiments, the secretion of the inflammatory mediator is decreased.

The inflammatory mediator may be monocyte chemotactic protein (mcp-1) or tumor necrosis factor alpha (tnf-α) according to certain embodiments.

In certain embodiments, the fat deposit, inflammation or oxidative stress is in an organ.

The organ may be pancreas, liver, kidney, testes, muscle, or adipose tissue.

According to certain embodiments, the invention provides a method of treating or preventing a liver disease in a subject in need thereof comprising administering to the subject vitamin A or a retinoic acid receptor-beta (RARβ) agonist.

In certain embodiments, the liver disease is associated with obesity.

In certain embodiments, the liver disease is associated with a high fat diet.

In certain embodiments, the liver disease is associated with vitamin A deficiency.

In certain embodiments, the liver disease is fatty liver disease (FLD), liver fibrosis, or hepatic steatosis.

In certain embodiments, the liver disease is non-alcoholic FLD (NAFLD), alcohol associated FLD, or non-alcoholic steatohepatitis (NASH).

In certain embodiments, the liver disease is associated with reduced vitamin A level in the liver.

According to certain embodiments, the invention provides a method of decreasing the activation of hepatic stellate cells (HSCs) in a subject in need thereof comprising administering to the subject vitamin A or a retinoic acid receptor-beta (RARβ) agonist.

According to certain embodiments, the invention provides a method of decreasing the level of hepatic reactive oxygen species (ROS) in a subject in need thereof comprising administering to the subject vitamin A or a retinoic acid receptor-beta (RARβ) agonist.

According to certain embodiments, the invention provides a method of decreasing the level of alpha smooth muscle actin (α-SMA) in a subject in need thereof comprising administering to the subject vitamin A or a retinoic acid receptor-beta (RARβ) agonist.

According to certain embodiments, the invention provides a method of increasing the level of lethicin:retinol acyltransferase (LRAT) in the liver of a subject in need thereof comprising administering to the subject vitamin A or a retinoic acid receptor-beta (RARβ) agonist.

According to certain embodiments, the invention provides a method of increasing the level of RARβ in the liver of a subject in need thereof comprising administering to the subject vitamin A or a retinoic acid receptor-beta (RARβ) agonist.

According to certain embodiments, the invention provides a method of decreasing the level of SRBP1c in the liver of a subject in need thereof comprising administering to the subject vitamin A or a retinoic acid receptor-beta (RARβ) agonist.

In certain embodiments, the subject has a liver disease.

In certain embodiments, the liver disease is fatty liver disease (FLD), liver fibrosis, or hepatic steatosis.

In certain embodiments, the liver disease is non-alcoholic FLD (NAFLD), alcohol associated FLD, or non-alcoholic steatohepatitis (NASH).

In certain embodiments, the liver disease is associated with reduced vitamin A level in the liver.

In certain embodiments, the liver disease is associated with a pancreas disease.

According to certain embodiments, the invention provides a method of treating or preventing a kidney disease in a subject in need thereof comprising administering to the subject vitamin A or a retinoic acid receptor-beta (RARβ) agonist.

In certain embodiments, the kidney disease is associated with obesity.

In certain embodiments, the kidney disease is associated with a high fat diet.

In certain embodiments, the kidney disease is kidney fibrosis.

In certain embodiments, the kidney disease is a chronic kidney disease.

In certain embodiments, the kidney disease is diabetic nephropathy.

In certain embodiments, the kidney disease is associated with a pancreatic disease.

In certain embodiments, the kidney disease is associated with a liver disease.

In certain embodiments, the kidney disease is associated with reduced vitamin A level in the kidney.

According to certain embodiments, the invention provides a method of increasing the level of lethicin:retinol acyltransferase (LRAT) in the kidney of a subject in need thereof comprising administering to the subject vitamin A or a retinoic acid receptor-beta (RARβ) agonist.

According to certain embodiments, the invention provides a method of treating or preventing a disease associated with an organ-specific vitamin A deficiency in a subject in need thereof comprising administering to the subject vitamin A or a retinoic acid receptor-beta (RARβ) agonist.

In certain embodiments, the organ-specific vitamin A deficiency is associated with obesity.

In certain embodiments, the organ-specific vitamin A deficiency is associated with a high fat diet.

In certain embodiments, the subject has a normal serum level of vitamin A or retinyl esters.

In certain embodiments, the subject has an abnormal level of vitamin A or retinyl esters in a non-serum sample.

The organ may be pancreas, liver, kidney, testes, muscle, or adipose tissue.

According to certain embodiments, the invention provides a method of treating or preventing fibrosis in a subject in need thereof comprising administering to the subject vitamin A or a retinoic acid receptor-beta (RARβ) agonist.

According to certain embodiments, the invention provides a method of decreasing the accumulation of fat in a subject in need thereof comprising administering to the subject vitamin A or a retinoic acid receptor-beta (RARβ) agonist.

In certain embodiments, the fibrosis or accumulation of fat is in an organ.

The organ may pancreas, liver, kidney, testes, muscle, or adipose tissue.

According to certain embodiments, the vitamin A or agonist of retinoic acid receptor-beta (RARβ) is administered three times daily.

In certain embodiments, the vitamin A or agonist of retinoic acid receptor-beta (RARβ) is administered at an amount from 30-200 mg per day.

In certain embodiments, the vitamin A or agonist is administered at an amount from 50-150 mg per day.

In certain embodiments, the vitamin A or agonist is administered at an amount from 50-100 mg per day.

In certain embodiments, the vitamin A or agonist is administered at an amount from 100-150 mg per day.

In certain embodiments, the vitamin A or agonist of retinoic acid receptor-beta (RARβ) is administered orally.

In certain embodiments, the vitamin A or agonist of retinoic acid receptor-beta (RARβ) is administered intravenously or subcutaneously.

In certain embodiments, the vitamin A or agonist of retinoic acid receptor-beta (RARβ) does not elevate serum triglyceride in the subject.

In certain embodiments, the vitamin A or agonist of retinoic acid receptor-beta (RARβ) does not increase cardiovascular risk in the subject.

In certain embodiments, a therapeutic effective amount of the vitamin A or agonist of RARβ is administered.

In certain embodiments, both vitamin A and an agonist of RARβ are both administered to the subject.

In certain embodiments, vitamin A and an agonist of RARβ are administered concomitantly.

In certain embodiments, vitamin A and an agonist of RARβ are administered sequentially.

According to certain embodiments, the invention provides a pharmaceutical composition comprising vitamin A or a retinoic acid receptor-beta (RARβ) agonist or a pharmaceutically acceptable salt thereof at an amount from about 10 mg to about 60 mg.

In certain embodiments, the amount of the vitamin A or agonist is from 15 mg to about 50 mg.

In certain embodiments, the amount of the vitamin A or agonist is from 15 mg to about 35 mg.

In certain embodiments, the amount of the vitamin A or agonist is from about 35 mg to about 50 mg.

In certain embodiments, the amount of the vitamin A or agonist is from about 30 mg to about 200 mg.

In certain embodiments, the amount of the vitamin A or agonist is from about 50 mg to about 150 mg.

In certain embodiments, the amount of the vitamin A or agonist is from about 50 mg to about 100 mg.

In certain embodiments, the amount of the vitamin A or agonist is from about 100 mg to about 150 mg.

According to certain embodiments, the invention provides a pharmaceutical composition comprising vitamin A or a retinoic acid receptor-beta (RARβ) agonist or a pharmaceutically acceptable salt thereof at a concentration from about 0.1 mg to about 10 mg per 100 ml.

In certain embodiments, the concentration is from about 0.5 mg to about 5 mg per 100 ml.

In certain embodiments, the concentration is from about 1 mg to about 3 mg per 100 ml.

In certain embodiments, the concentration is from about 1.5 mg to about 2.5 mg per 100 ml.

In certain embodiments, the agonist is a highly specific RARβ agonist.

In certain embodiments, the agonist is AC261066.

In certain embodiments, the agonist is AC55649.

In certain embodiments, the pharmaceutical composition comprises both vitamin A and an agonist of RARβ.

According to certain embodiments, the invention provides a method of controlling triglyceride level in a subject in need thereof, comprising administering to the subject vitamin A or a retinoic acid receptor-beta (RARβ) agonist.

According to certain embodiments, the invention provides a method of controlling cholesterol level in a subject in need thereof, comprising administering to the subject vitamin A or a retinoic acid receptor-beta (RARβ) agonist.

According to certain embodiments, the invention provides a method of treating or preventing hypertriglyceridemia or a condition associated with hypertriglyceridemia in a subject in need thereof, comprising administering to the subject vitamin A or a retinoic acid receptor-beta (RARβ) agonist.

According to certain embodiments, the invention provides a method of treating or preventing hypercholesterolemia or a condition associated with hypercholesterolemia in a subject in need thereof, comprising administering to the subject vitamin A or a retinoic acid receptor-beta (RARβ) agonist.

According to certain embodiments, the invention provides a method of reducing the production of HMG-CoA reductase in a subject in need thereof, comprising administering to the subject vitamin A or a retinoic acid receptor-beta (RARβ) agonist.

According to certain embodiments, the invention provides a method of reducing a clinically significant side effect of elevated blood triglyceride and/or cholesterol level caused by a drug in a subject in need thereof, comprising administering to the subject treated by said drug vitamin A or a retinoic acid receptor-beta (RARβ) agonist.

In certain embodiments, the triglyceride and/or cholesterol level in an organ (e.g., pancreas, liver, kidney, testes, muscle, or adipose tissue) is controlled.

According to certain embodiments, the invention provides a method of regulating the expression of genes involved in lipogenesis and lipid catabolism.

In certain embodiments, the expression of such genes is regulated in an organ (e.g., pancreas, liver, kidney, testes, muscle, or adipose tissue). The regulation may result in an increase of oxidation of lipids or a decrease in lipogenesis.

According to certain embodiments, the invention provides a method of controlling glucose level in a subject in need thereof, comprising administering to said subject vitamin A or a retinoic acid receptor-beta (RARβ) agonist.

According to certain embodiments, the invention provides a method of controlling glucose intolerance in a subject in need thereof, comprising administering to said subject vitamin A or a retinoic acid receptor-beta (RARβ) agonist.

In certain embodiments, the glucose level in an organ (e.g., pancreas, liver, kidney, testes, muscle, or adipose tissue) is controlled.

The subject in need may have a metabolic syndrome related condition according to one embodiment of the invention.

The subject in need may have a condition selected from the group consisting of diabetes, cardiovascular disease, hyperglycemia, and hyperlipidemia.

According to certain embodiments, the invention provides a method of controlling insulin resistance in a subject in need thereof, comprising administering to said subject vitamin A or a retinoic acid receptor-beta (RARβ) agonist.

The retinoic acid receptor-beta (RARβ) agonist of the present invention may reduce triglyceride or cholesterol synthesis in the subject according to certain embodiments.

The retinoic acid receptor-beta (RARβ) agonist may reduce triglyceride or cholesterol transport in the subject according to certain embodiments.

The retinoic acid receptor-beta (RARβ) agonist is a highly specific RARβ agonist according to certain embodiments.

The retinoic acid receptor-beta (RARβ) agonist is a highly specific RARβ2 agonist according to certain embodiments.

The retinoic acid receptor-beta (RARβ) agonist is AC201066 according to certain embodiments.

The retinoic acid receptor-beta (RARβ) agonist is AC55649 according to certain embodiments.

The condition associated with hypertriglyceridemia/hypercholesterolemia is diabetes according to certain embodiments.

The condition associated with hypertriglyceridemia/hypercholesterolemia is a cardiovascular disease according to certain embodiments.

The condition associated with hypertriglyceridemia/hypercholesterolemia is hyperlipidemia according to certain embodiments.

The agonist of retinoic acid receptor-beta (RARβ) is administered three times daily according to certain embodiments.

The retinoic acid receptor-beta (RARβ) agonist is administered at an amount from about 30 mg to about 200 mg per day according to certain embodiments.

The retinoic acid receptor-beta (RARβ) agonist is administered at an amount from about 50 mg to about 150 mg per day according to certain embodiments.

The retinoic acid receptor-beta (RARβ) agonist is administered at an amount from about 50 mg to about 100 mg per day according to certain embodiments.

The retinoic acid receptor-beta (RARβ) agonist is administered at an amount from about 100 mg to about 150 mg per day according to certain embodiments.

The retinoic acid receptor-beta (RARβ) agonist is administered orally according to certain embodiments.

The retinoic acid receptor-beta (RARβ) agonist is administered intravenously or subcutaneously according to certain embodiments.

The method may further comprise administering a second drug according to certain embodiments.

The second drug is a drug for treating hypertriglyceridemia or a condition associated with hypertriglyceridemia according to certain embodiments.

The second drug is a drug for treating hypercholesterolemia or a condition associated with hypercholesterolemia according to certain embodiments.

The second drug is another retinoic acid receptor-beta (RARβ) agonist according to certain embodiments.

According to certain embodiments, the triglyceride level in the blood of the subject is reduced to be less than 150 mg/dL.

According to certain embodiments, the triglyceride level in the blood of the subject is reduced to be 150 to 199 mg/dL.

According to certain embodiments, the cholesterol level in the blood of the subject is reduced to be 200 mg/dL or less.

According to certain embodiments, the cholesterol level in the blood of the subject is reduced to be 201 to 240 mg/dL.

According to certain embodiments, the production of HMG-CoA reductase in the subject is reduced at the mRNA level.

According to certain embodiments, the therapeutic effect of vitamin A or a retinoic acid receptor-beta (RARβ) agonist may be achieved from about 1 day to about 8 days after the agonist is administered to the subject in need.

According to certain embodiments, the invention provides a pharmaceutical composition comprising vitamin A or a retinoic acid receptor-beta (RARβ) agonist having at least 70% RARβ2 binding affinity of AC261066, or a pharmaceutically acceptable salt thereof at an amount from about 10 mg to about 60 mg.

The pharmaceutical composition may contain the agonist at an amount from 15 mg to about 50 mg according to certain embodiments.

The pharmaceutical composition may contain the agonist at an amount from 15 mg to about 35 mg according to certain embodiments.

The pharmaceutical composition may contain the agonist at an amount from about 35 mg to about 50 mg according to certain embodiments.

The pharmaceutical composition may contain the agonist at an amount from about 30 mg to about 200 mg according to certain embodiments.

The pharmaceutical composition may contain the agonist at an amount from about 50 mg to about 150 mg according to certain embodiments.

The pharmaceutical composition may contain the agonist at an amount from about 50 mg to about 100 mg according to certain embodiments.

The pharmaceutical composition may contain the agonist at an amount from about 100 mg to about 150 mg according to certain embodiments.

According to certain embodiments, the invention provides a pharmaceutical composition comprising vitamin A or a retinoic acid receptor-beta (RARβ) agonist or a pharmaceutically acceptable salt thereof at a concentration from about 0.1 mg to about 10 mg per 100 ml.

The pharmaceutical composition may contain the agonist at a concentration from about 0.5 mg to about 5 mg per 100 ml according to certain embodiments.

The pharmaceutical composition may contain the agonist at a concentration from about 1 mg to about 3 mg per 100 ml according to certain embodiments.

The pharmaceutical composition may contain the agonist at a concentration from about 1.5 mg to about 2.5 mg per 100 ml according to certain embodiments.

The pharmaceutical composition may further comprise another agonist of RARβ according to certain embodiments.

The retinoic acid receptor-beta (RARβ) agonist of the pharmaceutical composition is a highly specific RARβ2 agonist according to certain embodiments.

The retinoic acid receptor-beta (RARβ) agonist of the pharmaceutical composition is AC261066 according to certain embodiments.

The retinoic acid receptor-beta (RARβ) agonist of the pharmaceutical composition is AC55649 according to certain embodiments.

DETAILED DESCRIPTION

Figure 1:
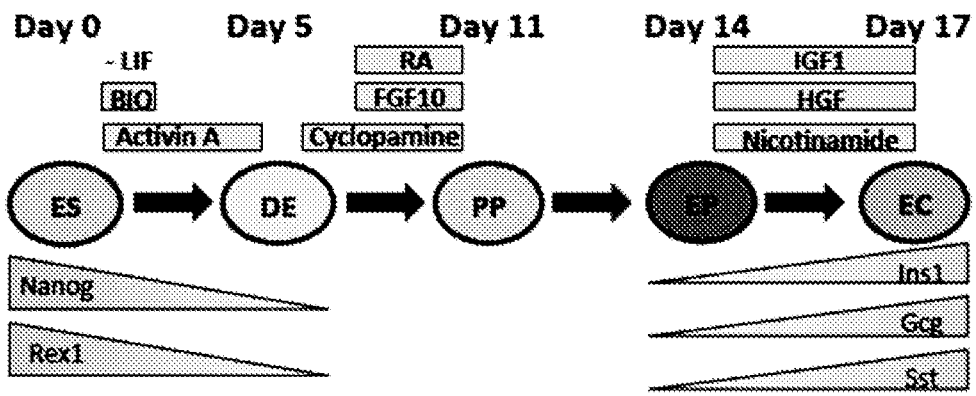
FIG. 1: Pancreatic endocrine differentiation protocol and its impact on the molecular level. (A) Schematic representation of the endocrine differentiation protocol adapted from D'Amour et al. (2006) used on mouse ES cells. Briefly, embryonic stem (ES) cells are treated with different growth factors to successively differentiate into definitive endoderm (DE), pancreatic progenitor (PP), endocrine progenitor (EP), and endocrine cells (EC). (B) WT mouse ES cells were subjected to the 17-day differentiation protocol. Each lane represents a different condition at specific time points. RT-PCR analyses were performed to monitor the expression of pancreatic differentiation markers such as insulin-1 (Ins1), glucagon (Gcg), somatostatin (Sst), neurogenin-3 (Ngn3), Pdx1 and Sox17, as well as the stem cell markers Nanog and Rex1. HPRT1 amplification was used as a control housekeeping gene. Pancreas extracts from C57BL/6 WT mice were used as a positive control.
Figure 1:
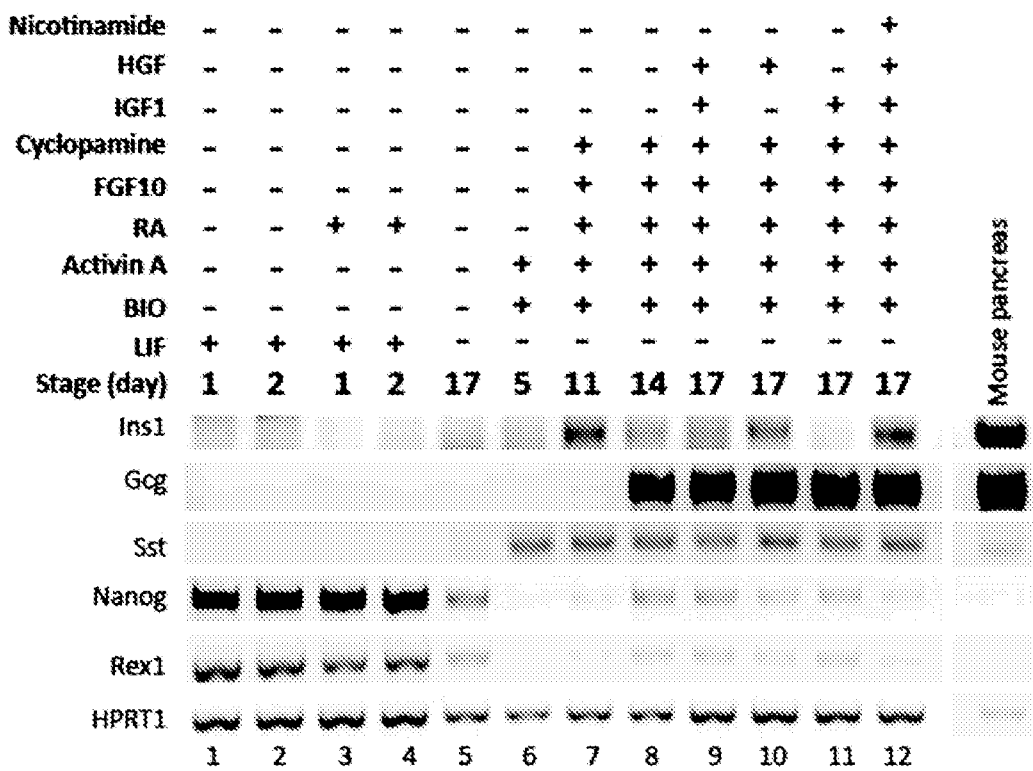

As discussed above, there remains a need to provide alternate therapies or management for the treatment or prevention of certain metabolic syndrome related conditions, including controlling the level of cholesterol, triglyceride and/or glucose in a subject in need thereof, as well as treating or preventing diseases caused by fat accumulation or vitamin A deficiency in a subject in need thereof. Accordingly, the present invention relates to uses of vitamin A and retinoic acid receptor β (RARβ) agonists in this regard.

Mouse embryonic stem (ES) cells are pluripotent cells derived from the inner cell mass of blastocyst-stage (day 3.5) embryos (10, 11). Upon LIF removal, ES cells spontaneously differentiate into all three primary embryonic germ layers: endoderm, mesoderm, and ectoderm (10). Several research groups have shown that the directed differentiation of ES cells along the endocrine pathway can be achieved by using a wide range of growth/differentiation factors, including retinoic acid (RA) treatment (12-17).

Although the effects of RA on cells and tissues are known to occur through the activation of retinoic acid receptors (RARα, RARβ, and RARγ) and their isoforms (6, 18), the events occurring downstream of RA signaling that direct the differentiation of definitive endoderm into endocrine precursors are poorly understood (4, 5, 19).

A series of in vivo experiments, including some in Xenopus revealed, however, that RA signaling is crucial for endocrine pancreatic development (20). For instance, mice containing an inducible transgene for the dominant negative RARα403 mutant, used to ablate retinoic acid-dependent processes in vivo, lacked both a dorsal and ventral pancreas, and died at the neonatal stage (21). Impaired pancreatic islet development and repletion were also observed in vivo, in vitamin A deficiency models (22, 23). Moreover, a study of the developmental pathways involved during in vitro islet neogenesis revealed a 3-fold induction of RARβ transcripts from "adherent" to "expanded" stages of endocrine differentiation (24). Another study, based on the role of CRABP1 and RBP4 in pancreatic differentiation, corroborated the up-regulation of RARβ in early differentiation (11). While previous studies suggested that RARβ is essential to pancreas development, little is known about its functional role in pancreas formation and islet maintenance in adults (25, 26).

Vitamin A metabolite all trans-retinoic acid (RA) acting through its cognate receptors, retinoic acid receptor (RAR) alpha, beta, gamma, possesses anti-obesity and anti-lipogenic properties through regulation of genes involved in energy metabolism and adipogenesis (75).

Using animal models, the present inventors have discovered that retinoic acid receptor β (RARβ) plays an important role in organ development, maintenance, and function. The inventors discovered that vitamin A and RARβ agonists increase RARβ function and signaling; vitamin A and these RARβ agonists also increase the level of RARβ.

The present inventors also discovered that vitamin A and RARβ agonists are effective in treating and preventing high fat diet associated disease in pancreas, liver, kidney, testes, muscle, or adipose tissue and other organs. Furthermore, the inventors discovered that vitamin A and such (RARβ) agonists can restore vitamin A signaling in organs that show vitamin A deficiencies.

Vitamin A and these RARβ agonists, according to the discovery of the present inventors, increase insulin signaling, decrease fat deposit, prevent inflammation, and decrease oxidative stress in various organs, including pancreas, liver, kidney, testes, muscle, or adipose tissue. They also decrease the level of alpha smooth muscle actin (α-SMA) but increase the level of lethicin:retinol acyltransferase (LRAT) and RARβ. When used to treat liver diseases, vitamin A and these RARβ agonists decrease the activation of hepatic stellate cells (HSCs) and the level of hepatic reactive oxygen species (ROS).

The present inventors discovered that vitamin A or agonists of retinoic acid receptor-beta (RARβ) do not elevate serum triglyceride or increase cardiovascular risk at a clinically significant level.

As described above, a common side effect of retinoid agonist administration to humans and rodents includes both elevated triglyceride and cholesterol levels. The inventors of the present application carefully studied different types of retinoid agonists using carefully-designed animal models. Contrary to the reports that retinoid agonists increase triglyceride and cholesterol levels, the inventors discovered that RARβ (e.g., RARβ2) agonists can actually lower serum cholesterol and/or triglyceride level in animals.

The present invention thus also provides pharmaceutical compositions comprising a RARβ2 agonist, and uses of such agonists to control hypertriglyceridemia and/or hypercholesterolemia, as well as conditions associated thereof.

The retinoic acid receptor (RAR) is a type of nuclear receptor that is activated by both all-trans retinoic acid and 9-cis retinoic acid. There are three retinoic acid receptors (RAR), RARα, RARβ, and RARγ, encoded by the RARα, RARβ, RARγ genes, respectively. Each receptor isoform has several splice variants: two—for α, four—for β, and two—for γ.

RAR heterodimerizes with RXR and in the absence of ligand, the RAR/RXR dimer binds to hormone response elements known as retinoic acid response elements (RAREs) complexed with corepressor protein. Binding of agonist ligands to RAR results in dissociation of corepressor and recruitment of coactivator protein that, in turn, promotes transcription of the downstream target gene into mRNA and eventually protein.

There are three retinoic acid receptors (RAR), RARα, RARβ, and RARγ, encoded by the RARα, RARβ, RARγ genes, respectively. Each receptor isoform has several splice variants: two—for α, four—for β, and two—for γ.

The RARβ subtype consists of four known isoforms RARβ1, RARβ2, RARβ3 and RARβ4. The ligand binding domains of the four isoforms are identical, while the variation between the isoforms is located within the proximal N-terminus, which encompasses the ligand-independent activation domain (AF-1) (Lund et al., 2005, J. Med. Chem. 48: 7517-7519).

It has been reported that the ligand binding domain, i.e., AF-2, of a given RAR isotype cooperates with the AF-1 domain in a promoter context manner (Lund et al., 2005, J. Med. Chem. 48: 7517-7519; Nagpal et al., 1992, Cell, 70, 1007-1019; Nagpal et al., 1993, EMBO J. 12, 2349-2360.) The AF-2 domains are conserved between the isoforms, the AF-1 domains are not (Lund et al., 2005, J. Med. Chem. 48: 7517-7519, Gelman et al. 1999, J. Biol. Chem., 274, 7681-7688; Benecke et al. 2000, EMBO Rep., 1, 151-157.) Relying on RARβ (e.g., RARβ2) receptor-ligand crystal structure, various RARβ agonists have been designed and identified (Lund et al., 2005, J. Med. Chem. 48: 7517-7519; Germain et al., 2004, EMBO reports, 5(9): 877-882).

Figure 26:
FIG. 26. Modeling structure reproduced from Lund et al., 2005, J. Med. Chem. 48: 7517-7519.

The cooperation and complexes formed between AC261066 and/or AC 55649 with AF-1 and AF-2 may serve as an effective model system for identifying and selecting additional compounds that may be used to control hypertriglyceridemia, hypercholesterolemia and conditions associated thereof according to embodiments of the present invention (e.g., FIG. 26).

Known RARβ agonists include but are not limited to: AC261066, AC55649, Tazarotene, Adapalene, 9-cis-retinoic acid, and TTNPB. AC261066 and AC55649 are highly-specific RARβ agonists. The term "highly-specific RARβ agonists" also include other agonists having a binding affinity similar to AC261066 or AC55649, e.g., at least 50% or greater, preferably 75% or greater, more preferably 90% or greater of the RARβ binding affinity of AC261066 or AC55649. The term "highly-specific RARβ2 agonists" include agonists having a binding affinity similar to AC261066 or AC55649, e.g., at least 50% or greater, preferably 75% or greater, more preferably 90% or greater of the RARβ2 binding affinity of AC261066 or AC55649. A highly-specific RARβ (e.g., RARβ2) agonist preferably has an affinity for RARβ (e.g., RARβ2) greater than 6.00 pEC50, more preferably greater than 6.50 pEC50, more preferably greater than 7.00 pEC50, more preferably greater than 7.50 pEC50, more preferably greater than 7.75 pEC50, and even more preferably greater than 8.00 pEC50.

RARβ agonists include the fluorinated alkoxythiazoles previously described (65), such as:

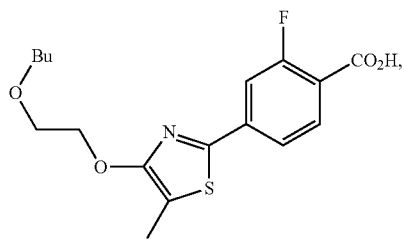

4'-Octyl-[1,1'-biphenyl]-4-carboxylic acid (65), Adapalene (67), BMS-231973, BMS-228987, BMS-276393, BMS-209641 (66), BMS-189453 {4-[(1E)-2-(5,6-Dihydro-5,5-dimethyl-8-phenyl-2-naphthalenyl)ethenyl]-benzoic acid} (68), CD2019 (6-[4-methoxy-3-(1-methylcyclohexyl)phenyl]naphthalene-2-carboxylic acid), compounds described in WO2008/064136 and WO2007009083 and tazarotene (ethyl 6-[2-(4,4-dimethyl-3,4-dihydro-2H-1-benzothiopyran-6-yl)ethynyl]pyridine-3-carboxylate). Structures of some RARβ agonists are provided below:

AC261066:

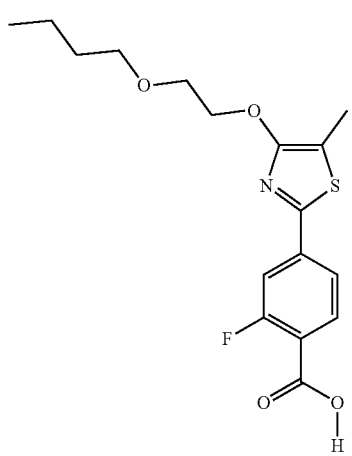

AC55649:

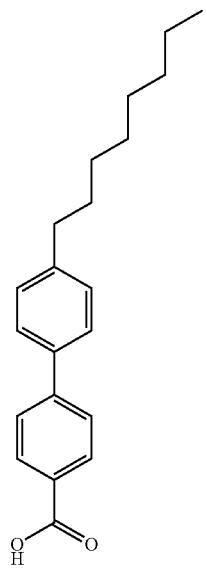

Tazarotene:

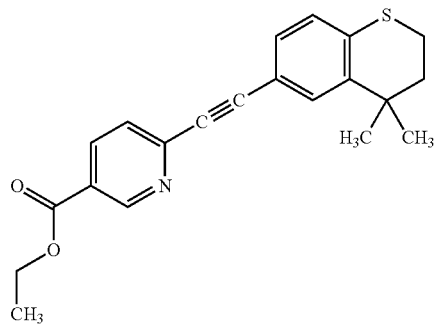

Adapalene:

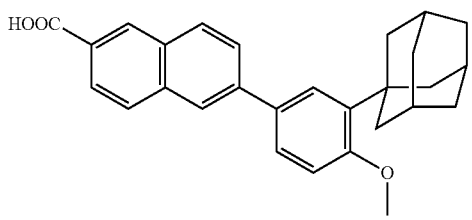

9-cis-retinoic acid:

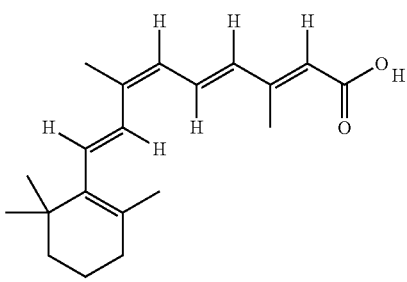

TTNPB:

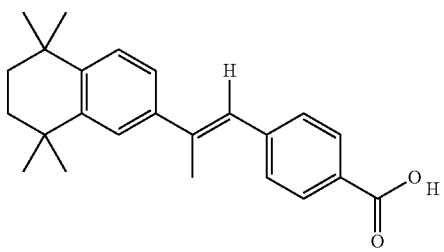

RARβ agonists also include those disclosed in published PCT patent application WO2008/064136, WO2007/009083 and published U.S. patent application US2009/0176837, each of which is incorporated herein by reference in its entirety. The highly specific RARβ agonists, e.g., AC261066 and AC55649, are highly isoform-selective agonists for the human RARβ2 receptors as described in Lund et al. (2005, J. Med. Chem., 48, 7517-7519, incorporated herein by reference in its entirety).

RARβ2 receptor agonist of the present invention may be selected from the following compounds or an ester thereof (RARβ2 binding activities indicated in Tables 1 and 2 below):

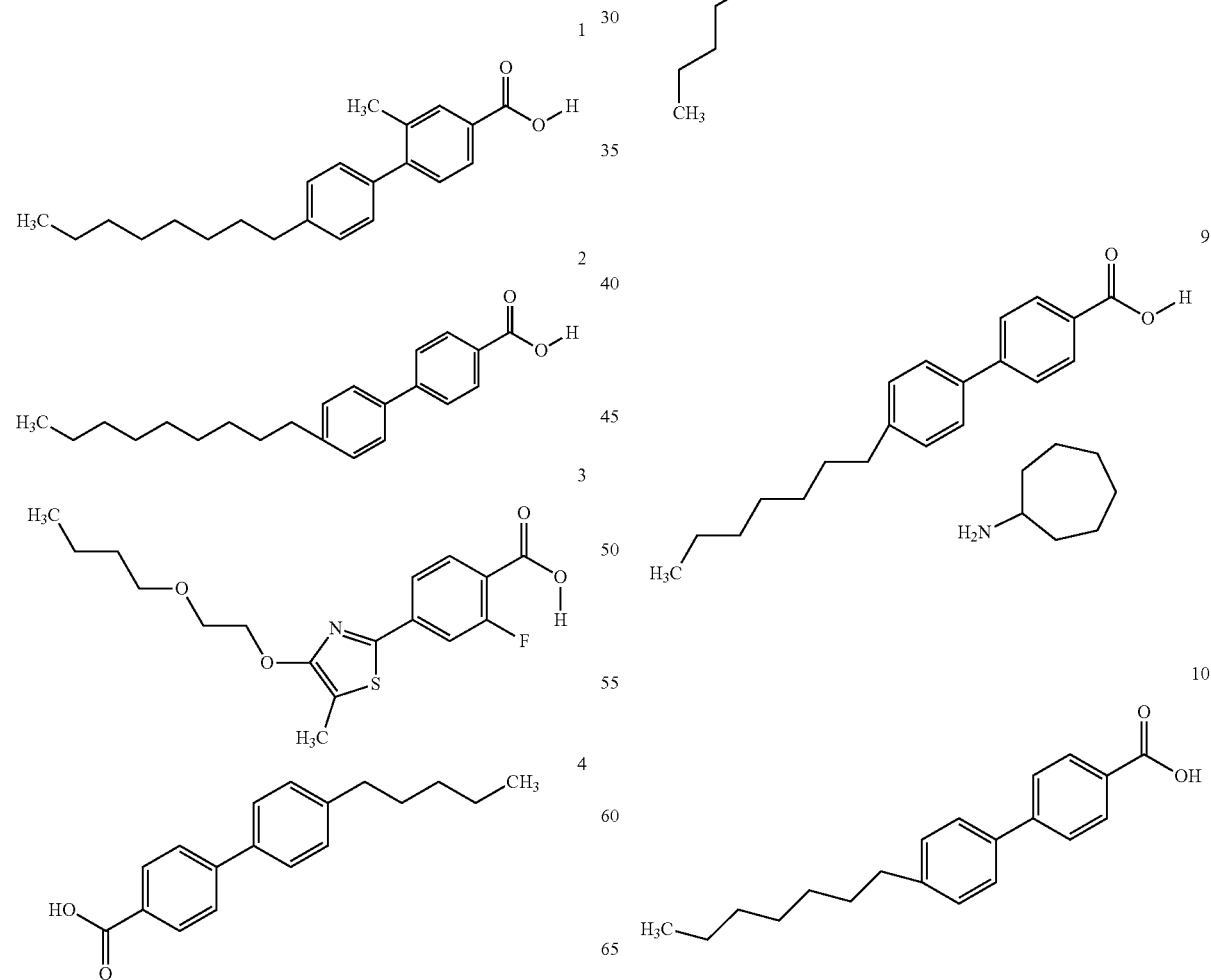

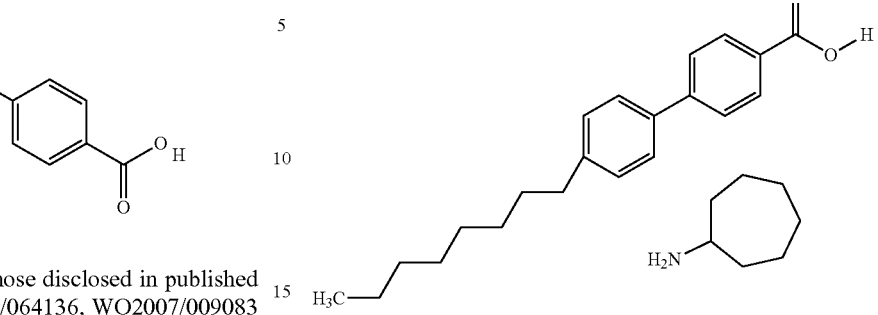

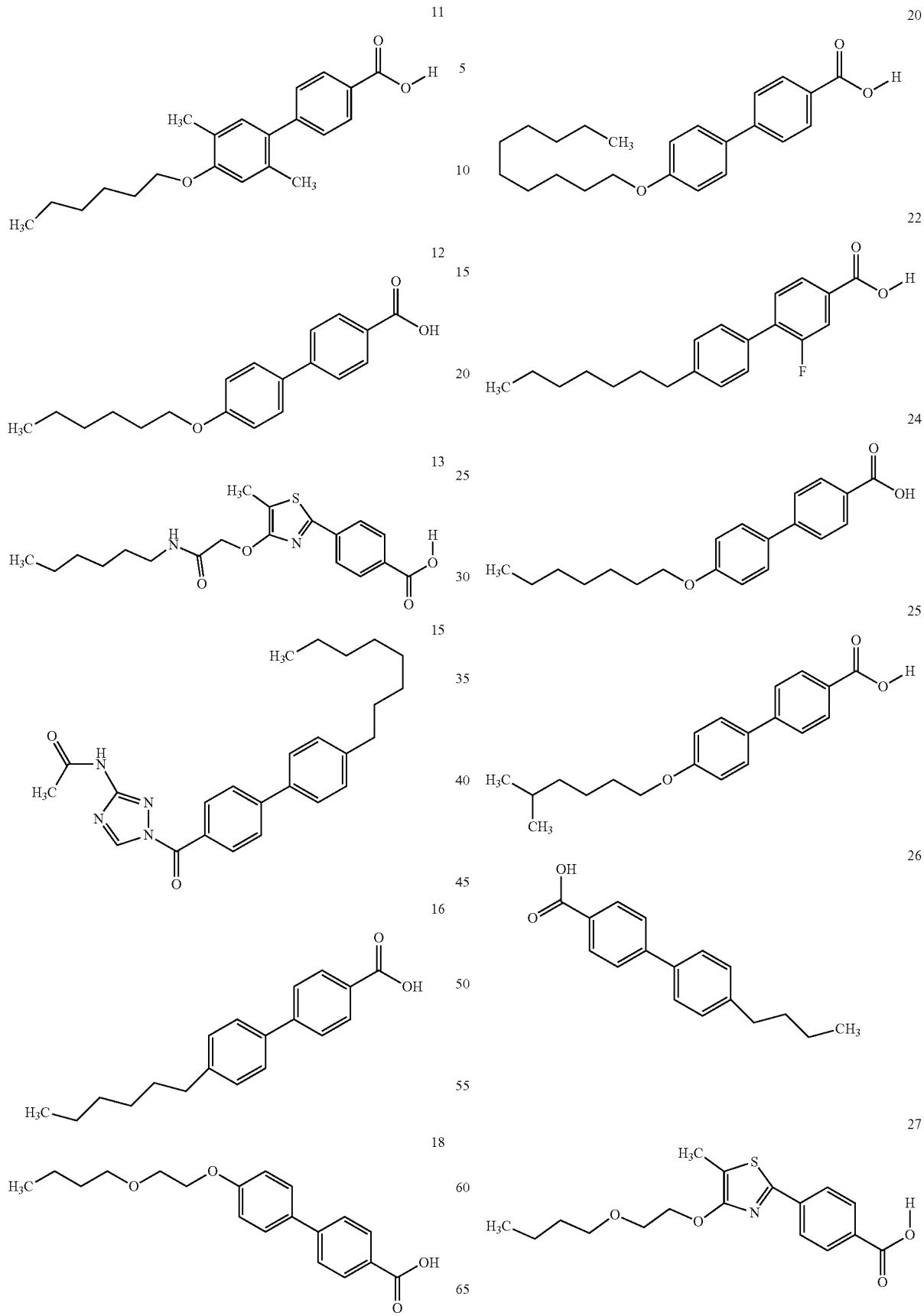

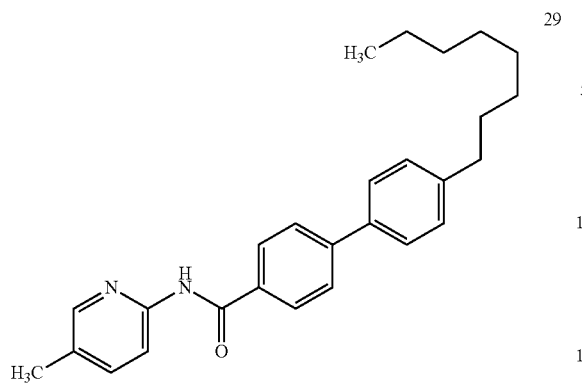
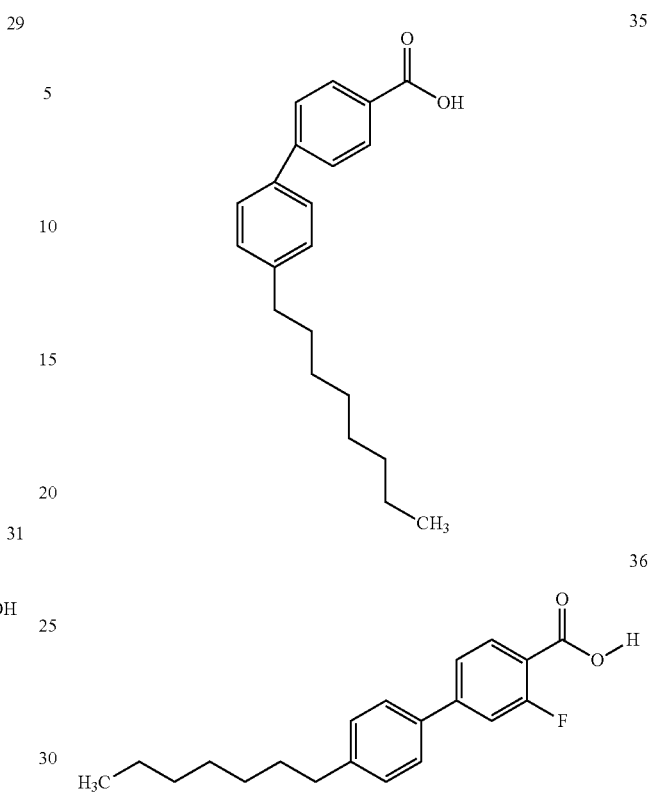
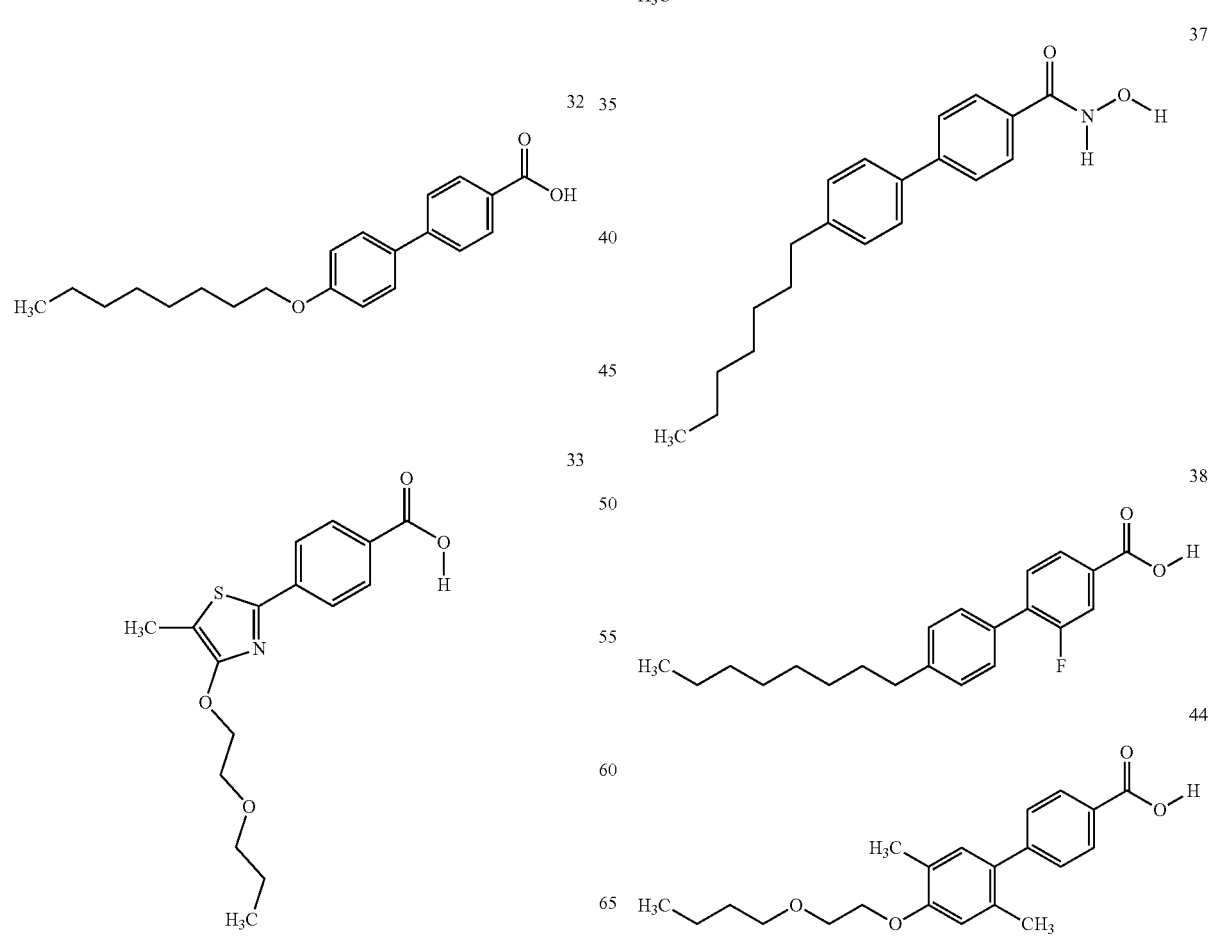

45
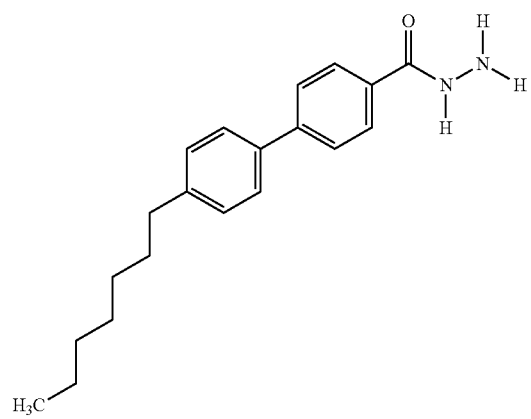
46
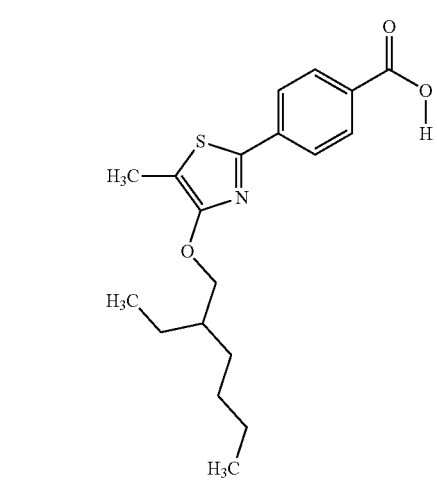
47
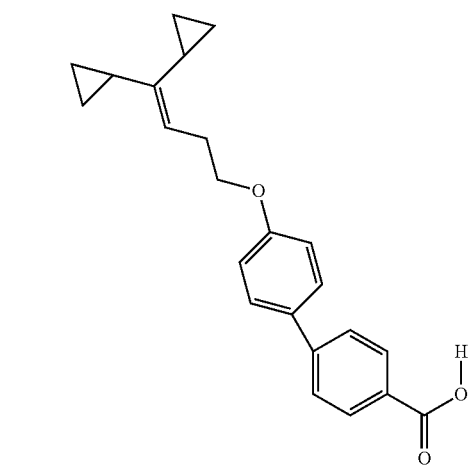
49
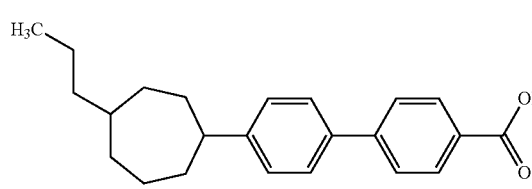
50
51
52
53
54
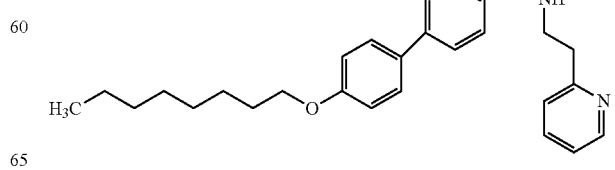

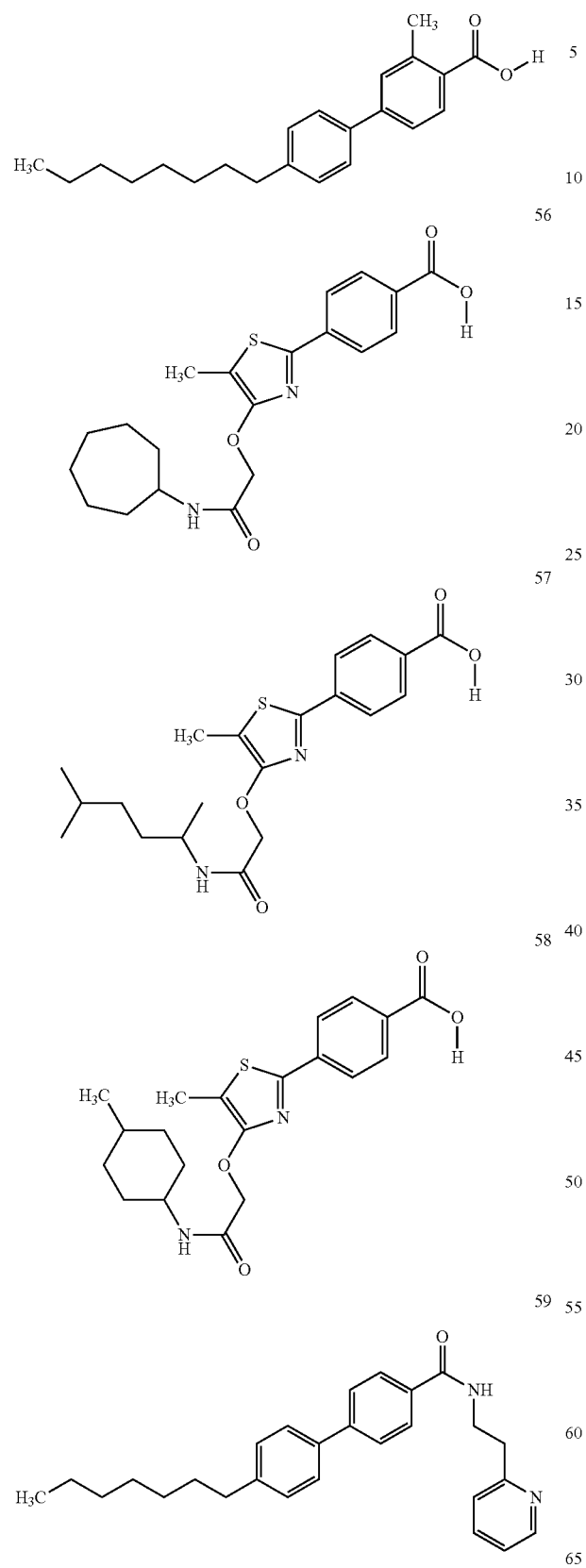
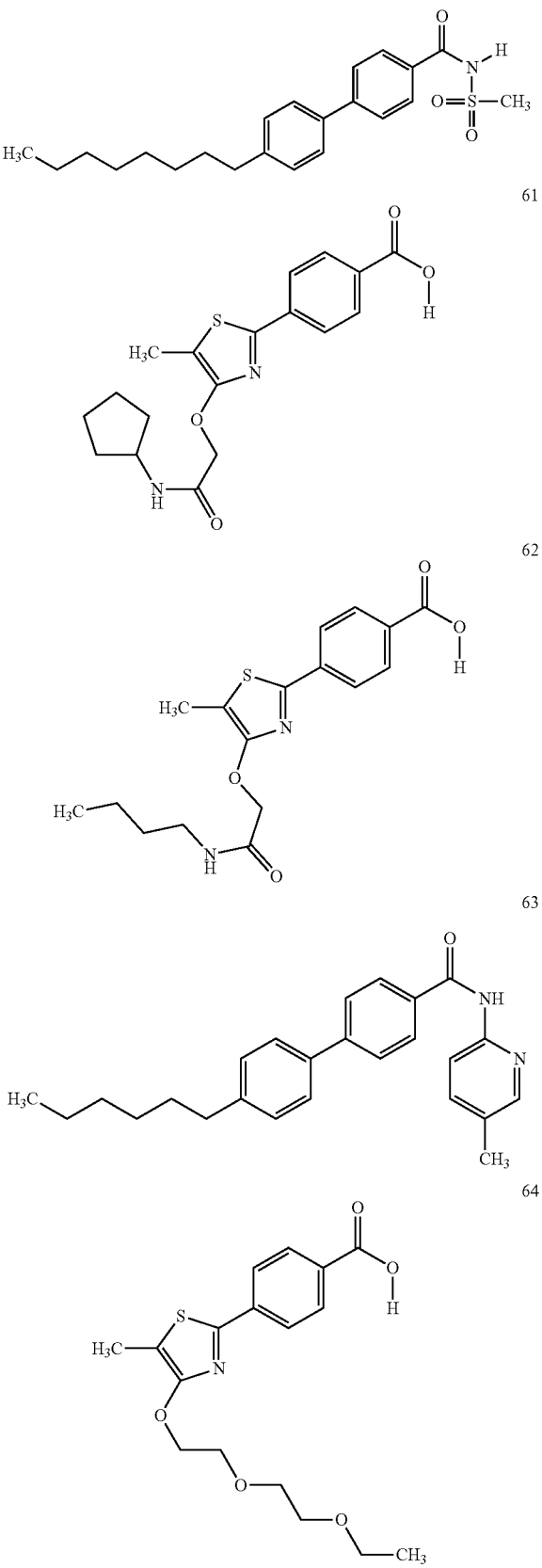

The functional receptor assay, receptor selection and amplification may be performed as described in WO2007/009083. For example, Technology (R-SAT) may be used to investigate the pharmacological properties of known and novel RARβ agonists useful for the present invention. R-SAT is disclosed, for example, in U.S. Pat. Nos. 5,707,798, 5,912,132, and 5,955,281, Piu et al., 2006, Beta Arrestin 2 modulates the activity of Nuclear Receptor RAR beta 2 through activation of ERK2 kinase, Oncogen, 25(2): 218-29 and Burstein et al., 2006, Integrative Functional Assays, Chemical Genomics and High Throughput Screening: Harnessing signal transduction pathways to a common HTS readout, Curr Pharm Des, 12(14): 1717-29 all of which are hereby incorporated herein by reference in their entireties, including any drawings.

The relevant RARβ2 receptor modulating activities of the above compounds are provided in Table 1 and Table 2 of WO2007/009083:

TABLE 1

| Compound no. | RARβ2 | |
|---|---|---|
| | % Eff. | pEC50 |
| 1 | 39 | 8.64 |
| 2 | 126 | 8.10 |
| 3 | 107 | 8.02 |
| 4 | 44 | 7.82 |
| 6 | 104 | 7.73 |
| 8 | 79 | 7.66 |
| 9 | 76 | 7.59 |
| 10 | 64 | 7.58 |
| 11 | 78 | 7.56 |
| 12 | 72 | 7.54 |
| 13 | 85 | 7.38 |
| 15 | 76 | 7.37 |
| 16 | 37 | 7.34 |
| 18 | 108 | 7.32 |
| 20 | 98 | 7.26 |
| 22 | 36 | 7.24 |
| 24 | 58 | 7.21 |
| 25 | 65 | 7.20 |
| 26 | 36 | 7.15 |
| 27 | 95 | 7.12 |
| 29 | 78 | 7.08 |
| 31 | 80 | 7.02 |
| 32 | 70 | 7.02 |
| 33 | 98 | 6.96 |
| 35 | 83 | 6.94 |
| 36 | 42 | 6.91 |
| 37 | 49 | 6.87 |
| 38 | 70 | 6.81 |
| 44 | 41 | 6.61 |
| 45 | 78 | 6.59 |
| 46 | 54 | 6.58 |
| 47 | 58 | 6.58 |
| 49 | 59 | 6.55 |
| 50 | 85 | 6.53 |
| 51 | 59 | 6.51 |
| 52 | 45 | 6.41 |
| 53 | 99 | 6.29 |
| 54 | 39 | 6.18 |
| 55 | 84 | 6.17 |
| 56 | 105 | 6.17 |
| 57 | 77 | 6.17 |
| 58 | 66 | 6.15 |
| 59 | 35 | 6.11 |
| 60 | 51 | 6.08 |
| 61 | 39 | 6.08 |
| 62 | 37 | 6.08 |
| 63 | 36 | 6.05 |
| 64 | 77 | 6.00 |

TABLE 2

| Compound no. | RARβ2 | |
|---|---|---|
| | % Eff. | pEC50 |
| 5 | 124 | 7.79 |
| 7 | 95 | 7.71 |
| 14 | 93 | 7.38 |
| 17 | 33 | 7.34 |
| 19 | 36 | 7.28 |
| 21 | 106 | 7.26 |
| 23 | 46 | 7.22 |
| 28 | 70 | 7.09 |
| 30 | 62 | 7.04 |
| 34 | 71 | 6.95 |
| 39 | 42 | 6.76 |
| 40 | 82 | 6.75 |
| 41 | 25 | 6.75 |
| 42 | 46 | 6.71 |
| 43 | 67 | 6.67 |
| 48 | 49 | 6.56 |

The highly specific RARβ agonist, e.g., AC261066, can prevent hepatic steatosis and activation of HSCs, marked by decreased expression of α-SMA. AC261066 can significantly diminish hepatic gene expression of pro-inflammatory mediators tumor necrosis factor-alpha (TNFα) and monocyte chemotactic protein-1 (MCP-1).

As used herein, the term "subject" means an animal, preferably a mammal, and most preferably a human. A subject in need thereof may be a patient having a metabolic syndrome related condition as discussed herein. For example, the subject may have insulin resistance, hypertension (high blood pressure), vitamin A deficiency, diabetes, fatty liver, high blood pressure, insulin resistance, obesity, abnormal (e.g., elevated) cholesterol, triglyceride and/or glucose levels, artery and heart diseases. Vitamin A deficiency and abnormal (e.g., elevated) cholesterol, triglyceride and/or glucose levels may be indicated by measurement in serum or a non-serum sample, including a sample from an organ (e.g., pancreas, liver, kidney, testes, muscle, or adipose tissue), of an animal, e.g., human.

As used herein, the term "vitamin A deficiency" refers to a lack of vitamin A or related metabolites including trans retinol, or a decreased level thereof in a serum sample or a non-serum sample, including a sample from an organ (e.g., pancreas, liver, kidney, testes, muscle, or adipose tissue), of an animal, e.g., human. An animal having vitamin A deficiency according to the present invention may have a normal vitamin A (or related metabolites) level as measured using a serum sample, but still exhibits vitamin A deficiency as measured using a non-serum sample from the animal.

As used herein, the term "hyperglycemia" refers to a condition of high blood sugar in which an excessive amount of glucose circulates in the blood plasma. This is generally a glucose level higher than 11.1 mmol/l (200 mg/dl), but symptoms may not start to become noticeable until even higher values such as 15-20 mmol/l (~250-300 mg/dl). A subject with a consistent range between ~5.6 and ~7 mmol/l (100-126 mg/dl) (American Diabetes Association guidelines) is considered hyperglycemic, while above 7 mmol/l (126 mg/dl) is generally held to have diabetes. Chronic levels exceeding 7 mmol/l (125 mg/dl) can produce organ damage.

As used herein, the term "hypertriglyceridemia" refers to a condition in which the triglyceride level is elevated with regard to the normal average level of triglycerides in a respective reference subject typically of the same ethnic background, age and gender. Typically, triglyceride tests are blood tests that measure the total amount of triglycerides in the blood. The National Cholesterol Education Program (NCEP) sets guidelines for fasting triglyceride levels as follows: normal triglycerides means there are less than 150 milligrams per deciliter (mg/dL); borderline high triglycerides are 150 to 199 mg/dL; while high triglycerides are 200 to 499 mg/dL and very high triglycerides are 500 mg/dL or higher (NCEP, Expert Panel on Detection, Evaluation, and Treatment of High Blood Cholesterol in Adults (Adult Treatment Panel III), 2002, Circulation, 106: 3143-3421). By way of a non-limiting example, with regard to humans the term hypertriglyceridemia in particular refers to blood triglyceride levels above about 150 mg/dl, in particular above about 180 mg/dl, or it could be a lower level that a physician treating the subject would consider to be significant. For borderline patients, non-pharmacologic measures are usually prescribed, e.g., a change in lifestyle including increased exercise, low fat diet and smoking cessation. When levels of triglycerides are greater than 200 mg/dL, drug treatment is typically given.

As used herein, the term "hypercholesterolemia" refers to a condition in which the cholesterol level is elevated with regard to the normal average level of cholesterol in a respective reference subject typically of the same ethnic background, age and gender. Typically, cholesterol tests are blood tests that measure the total amount of cholesterol in the blood. By way of non-limiting example, with regard to humans the term in particular refers to blood cholesterol levels above about 200, in particular above about 240 mg/dl, or it could be a lower level that a physician treating the subject would consider to be significant.

Often, tests for cholesterol are done with fasting for 9 to 12 hours, and it provides results for four different types of lipids (lipid panels).
Total cholesterol
LDL (low-density lipoprotein), the "bad cholesterol"
HDL (high-density lipoprotein), the "good cholesterol"
Triglycerides, another form of fat in the blood
Some lipid panels provide more detailed information, with information on the presence and sizes of various fat particles in the blood.

As a non-limiting guideline, for total cholesterol: 200 milligrams per deciliter (mg/dL) or less is considered normal. 201 to 240 mg/dL is borderline. Greater than 240 mg/dL is considered high.

As a non-limiting guideline, for HDL ("good cholesterol"), more is better: HDL 60 mg/dL or higher is good—it protects against heart disease. HDL between 40 and 59 mg/dL are acceptable. Less than 40 mg/dL HDL is low, increasing the risk of heart disease.

As a non-limiting guideline, for LDL ("bad cholesterol"), lower is better: An LDL of less than 100 mg/dL is optimal. An LDL of 100 to 129 mg/dL is near-optimal. LDL between 130 and 159 mg/dL is borderline high. LDL cholesterol between 160 and 189 mg/dL is high. An LDL of 190 mg/dL or more is considered very high.

As used herein, the term "condition associated with hypertriglyceridemia" refers to a disease condition which can be caused by and have as a symptom of elevated blood triglyceride levels, or a condition in which a physician treating the subject would consider controlling the level of triglyceride as helpful for the treatment or prevention of the condition. Conditions associated with hypertriglyceridemia include, but are not limited to, hyperlipidemia, atherosclerosis, cardiovascular diseases, stroke, insulin resistance, diabetes mellitus, diabetic nephropathy, idiopathic pancreatitis, metabolic syndrome, high blood pressure, obesity, high sugar diet, alcohol abuse, chronic renal failure, Rett Syndrome, and glycogen storage diseases, etc. Conditions associated with hypertriglyceridemia also include situations where the treatment of an unrelated disease causes elevated triglyceride levels as a drug side effect.

Rett Syndrome is an X-linked syndrome characterized by a series of symptoms, including loss of language, loss of coordination, and an autism-like presentation. Some of the effects of this syndrome appear to result from dysregulation of both cholesterol and triglyceride metabolism and might be treated with statins (Buchovecky et al, Nature Genetics, 45(9): 1013-20; Justice, M J, Seminar at Sloan Kettering Institute, May 1, 2014).

Hypertriglyceridemia may be classified as either primary or acquired (Assmann, et al., 1991, Am. J. Cardiol., 68: 13A-16A; Mancini et al., 1991, Am. J. Cardiol., 68: 17A-21A). Primary hypertriglyceridemias are inherited disorders, which include chylomicronemia (type I hyperlipoproteinemia), type V hyperlipoproteinemia, type III hyperlipoproteinemia (remnant hyperlipidemia or familial dysbetalipoproteinemia), familial hypertriglyceridemia, familial combined hyperlipidemia, and hepatic lipase deficiency (Assmann et al., 1991). The severity of the symptoms depends in part on whether the patient is homozygous or heterozygous. Primary hypertriglyceridemias may present as early as childhood. Acquired hypertriglyceridemia may be attributed to many factors, including metabolic disorders such as type II diabetes, diabetic nephropathy, metabolic syndrome, insulin resistance, pre-diabetes, syndrome X, obesity, hyperuricemia, Alström's syndrome, Rett Syndrome, and type I glycogen storage disease (Kreisberg, 1998, Am. J. Cardiol., 82: 67U-73U; Schmidt et al., 1996, Metabolism, 45: 699-706; Paisey et al., 2004, Clin. Endocrinol., 60: 228-231; Greene et al., 1991, J Pediatr., 119: 398-403). These conditions may also present in childhood. Similarly, hormonal disturbances may cause hypertriglyceridemia. In addition to insulin, triglyceride levels may be elevated as a result of hypothyroidism or polycystic ovary syndrome (Kvetny et al., 2004, Clin. Endocrinol., 61: 232-238; Pirwany et al., 2001, Clin. Endocrinol., 54: 447-453).

Acquired hypertriglyceridemia can be due to lifestyle factors such as diet (high sugar or carbohydrate intake) or alcohol consumption (Coughlan et al., 2000, Postgrad. Med., 108: 77-84). Chronic disease states such as renal disease (including nephrotic syndrome and renal failure) or paraproteinemia can also cause elevated triglycerides (Attman et al., 1997, Contrib. Nephrol., 120:1-10; Oda et al., 1998, Nephrol. Dial. Transplant., 13:45-49; Matteucci et al., 1996, Clin. Rheumatol., 15: 20-24). These disorders may also manifest in childhood.

As used herein, the term "condition associated with hypercholesterolemia" refers to a disease condition which can be caused by and have as a symptom of elevated blood cholesterol levels, or a condition in which a physician treating the subject would consider it helpful for the treatment or prevention of the condition by controlling the level of cholesterol of the subject. Conditions associated with hypercholesterolemia include, but are not limited to, hyperlipidemia, atherosclerosis, cardiovascular diseases, myocardial infarction, stroke, angina pectoris, ischemic colitis, transient ischemic attacks, Rett Syndrome, and peripheral artery disease. Conditions associated with hypercholesterolemia also include situations where the treatment of an unrelated disease causes elevated cholesterol level as a drug side effect.

Causes for conditions associated with hypercholesterolemia can be for example diabetes, diabetic nephropathy, nephritic syndrome, overweight, gout, alcohol abuse, hypothyroidism, anorexia nervosa, Zieve's syndrome, pregnancy, Rett Syndrome, and metabolic syndrome. There is also a genetic form of this metabolic derangement resulting in familial hypercholesterolemia. In addition, hypercholesterolemia contributes directly to the pathology of many forms of disease conditions, e.g. atherosclerosis, cardiovascular diseases, myocardial infarction, stroke, angina pectoris, ischemic colitis, transient ischemic attacks, and/or peripheral artery disease.

Some types of hypercholesterolemia lead to specific physical findings. For example, familial hypercholesterolemia (Type IIa hyperlipoproteinemia) may be associated with xanthelasma palpebrarum (yellowish patches underneath the skin around the eyelids), arcus senilis (white or gray discoloration of the peripheral cornea), and xanthomata (deposition of yellowish cholesterol-rich material) of the tendons, especially of the fingers. Type III hyperlipidemia may be associated with xanthomata of the palms, knees and elbows.

Longstanding elevation of serum cholesterol can lead to atherosclerosis. Over a period of decades, chronically elevated serum cholesterol contributes to formation of atheromatous plaques in the arteries. This can lead to progressive stenosis (narrowing) or even complete occlusion (blockage) of the involved arteries. Alternatively smaller plaques may rupture and cause a clot to form and obstruct blood flow. A sudden occlusion of a coronary artery results in a myocardial infarction or heart attack. An occlusion of an artery supplying the brain can cause a stroke. If the development of the stenosis or occlusion is gradual, blood supply to the tissues and organs slowly diminishes until organ function becomes impaired. At this point, tissue ischemia (restriction in blood supply) may manifest as specific symptoms. For example, temporary ischemia of the brain (commonly referred to as a transient ischemic attack) may manifest as temporary loss of vision, dizziness and impairment of balance, aphasia (difficulty speaking), paresis (weakness) and paresthesia (numbness or tingling), usually on one side of the body. Insufficient blood supply to the heart may manifest as chest pain, and ischemia of the eye may manifest as transient visual loss in one eye. Insufficient blood supply to the legs may manifest as calf pain when walking, while in the intestines it may present as abdominal pain after eating a meal.

Hyperlipidemias are conditions of abnormal plasma lipid/lipoprotein levels. Specific types of hyperlipidemias associated with vascular disease include Type IIb and Type IV hyperlipidemias. Type IV hyperlipidemia is characterized by elevated plasma levels of very low density lipoprotein (VLDL). Type IIb hyperlipidemia is characterized by elevated levels of VLDL and low density lipoprotein (LDL). One of the major causes of atherosclerosis and the related diseases, coronary heart disease (CHD), peripheral arterial disease (PAD), and cerebrovascular disease, is dyslipidemia. Dyslipidemia is an imbalance of each of the lipid components: total cholesterol (TC), high density lipoprotein (HDL) cholesterol, low density lipoprotein (LDL) cholesterol, and serum triglycerides. Because of their link with vascular disease, a number of approaches for controlling hyperlipidemias have been developed. Such approaches include changes in lifestyle, e.g. diet, exercise, and the like, as well drug therapy. Drugs finding use in the management of plasma lipid profiles include: bile acid binding resins; niacin; HMG-CoA reductase inhibitors; fabric acid derivatives, e.g. gemfibrozil; and the like.

Lipoproteins are classified by their density: very low density lipoprotein (VLDL), intermediate density lipoprotein (IDL), low density lipoprotein (LDL) and high density lipoprotein (HDL). All the lipoproteins carry cholesterol, but elevated levels of the lipoproteins other than HDL (termed non-HDL cholesterol), particularly LDL-cholesterol, are associated with an increased risk of atherosclerosis and coronary heart disease. In contrast, HDL ("good" cholesterol) helps remove cholesterol from the body tissues by efflux and carry cholesterol back to the liver for disposal. A high level of HDL cholesterol may lower one's chances of developing heart disease or stroke. LDL ("bad" cholesterol) carries mostly fat and only a small amount of protein from the liver to other parts of the body. A certain level of LDL in the blood is normal and healthy because LDL moves cholesterol to the parts of the body that need it. But it is sometimes called "bad cholesterol" because a high level may increase one's chances of developing heart disease. VLDL contains very little protein and it distributes the triglyceride produced by the liver. A high VLDL cholesterol level (e.g., as in hypercholesterolemia) can cause the buildup of cholesterol in the arteries and increases the risk of heart disease and stroke. An increase in plasma triglyceride levels causes a decrease in HDL levels.

Elevated levels of non-HDL cholesterol and LDL ("bad" cholesterol) in the blood may be a consequence of diet, obesity, inherited (genetic) diseases (such as LDL receptor mutations in familial hypercholesterolemia), or the presence of other diseases such as diabetes and an underactive thyroid.

The inventors of the present application have discovered and identified that specific RARβ (e.g., RARβ2) agonists significantly decrease circulating triglycerides and cholesterol levels. The present invention thus establishes a new, specific role for RARβ (e.g., RARβ2) agonists in lowering cholesterol and triglycerides in animals. The present invention provides pharmaceutical compositions comprising a RARβ (e.g., RARβ2) agonist, and uses of such RARβ (e.g., RARβ2) agonists for controlling the levels of triglyceride and/or cholesterol in a subject in need thereof. In addition, the inventors discovered that specific RARβ (e.g., RARβ2) agonists reduce the production of HMG-CoA reductase and transcription factor, e.g., by reducing HMG-CoA reductase mRNA or protein levels. The specific RARβ (e.g., RARβ2) agonists of the present invention also reduce the production (e.g., at mRNA and protein levels) of the sterol regulatory element binding protein 2 (SREBP-2), a transcription factor that regulates the genes of cholesterol metabolism. SREBP-2 increases HMG-CoA reductase mRNA.

HMG-CoA reductase (3-hydroxy-3-methyl-glutaryl-CoA reductase or HMGCR) is the rate-controlling enzyme of the mevalonate pathway which leads to the production of cholesterol, isoprenoids and related molecules. HMG-CoA reductase is the target of statins, a collection of drugs that are prescribed to limit cholesterol production, thus treating heart diseases. The reduction of HMG-CoA reductase production could lead to a decrease in the amount of cholesterol production.

As used herein, the term "control" refers to decrease, reduce or maintain the level of a molecule, e.g., triglyceride, cholesterol or glucose in a subject. The level may be measured in a serum sample or a non-serum sample, including a sample from an organ (e.g., pancreas, liver, kidney, testes, muscle, or adipose tissue). The control may be at the stage of triglyceride or cholesterol synthesis, transport or function. As used herein, the terms "decrease" and "reduce" are used interchangeably to refer to a negative change in the level, activity or function of a molecule, cell or organ. It is meant that the particular level, activity or function is lower by about 25%, about 50%, about 75%, about 90%, about 1-fold, about 2-fold, about 5 fold, about 10-fold, about 25-fold, about 50-fold, or about 100 fold, or lower, when compared to a control.

As used herein, the terms "elevate", "increase", "improve" and "enhance" are used interchangeably to refer to a positive change in the level, activity or function of a molecule, cell or organ. It is meant that the particular level, activity or function is higher by about 25%, about 50%, about 75%, about 90%, about 1-fold, about 2-fold, about 5 fold, about 10-fold, about 25-fold, about 50-fold, or about 100 fold, or higher, when compared to a control.

The expression "therapeutically effective" or "therapeutic effect" refers to a benefit including, but not limited to, the treatment or amelioration of symptoms of a condition discussed herein. It will be appreciated that the therapeutically effective amount or the amount of agent required to provide a therapeutic effect will vary depending upon the intended application (in vitro or in vivo), or the subject and disease condition being treated (e.g., nature of the severity of the condition to be treated, the particular inhibitor, the route of administration and the age, weight, general health, and response of the individual patient), which can be readily determined by a person of skill in the art. For example, an amount of vitamin A or an agonist of RARβ is therapeutically effective if it is sufficient to effect the treatment or amelioration of symptoms of a condition discussed herein.

The term "clinically significant side effect" is used herein to refer to a level of an undesired side effect caused by the administration of any drug or pharmaceutical composition that a physician treating the subject would consider significant. Such side effect may be elevated triglyceride and/or cholesterol level (e.g., in a serum sample or a non-serum sample, including a sample from an organ (e.g., pancreas, liver, kidney, testes, muscle, or adipose tissue)) or an increased cardiovascular risk. The term "clinically significant level" is used herein to refer to a level of a side effect such as cardiovascular risk caused by the administration of a pharmaceutical composition (e.g., vitamin A or RARβ agonist) that a physician treating the subject would consider to be significant.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 30%, preferably 20%, more preferably 10%.

As used herein, the term "comprises" means "includes, but is not limited to."

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

If a pharmaceutically acceptable salt of vitamin A or agonist of RARβ is utilized in pharmaceutical compositions, the salt preferably is derived from an inorganic or organic acid or base. For reviews of suitable salts, see, e.g., Berge et al, J. Pharm. Sci. 66: 1-19 (1977) wad Remington: The Science and Practice of Pharmacy, 20th Ed., ed. A. Gennaro, Lippincott Williams & Wilkins, 2000.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The term "carrier" is used interchangeably herein, and includes any and all solvents, diluents, and other liquid vehicles, dispersion or suspension aids, surface active agents, isotonic agents, thickening or emulsifying agents, preservatives, solid binders, lubricants and the like, as suited to the particular dosage form desired. Remington: The Science and Practice of Pharmacy, 20th Ed., ed. A. Gennaro, Lippincott Williams & Wilkins, 2000 discloses various carriers used in formulating pharmaceutically acceptable compositions and known techniques for the preparation thereof.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain solvents, diluents, and other liquid vehicles, dispersion or suspension aids, surface active agents, pH modifiers, isotonic agents, thickening or emulsifying agents, stabilizers and preservatives, solid binders, lubricants and the like, as suited to the particular dosage form desired.

The vitamin A or agonist of RARβ can be administered by any method known to one skilled in the art. For example, vitamin A or agonist of RARβ may be administered orally or parenterally.

The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art.

Combination therapies that comprise the combination of vitamin A and agonist of RARβ of the present invention, and further with one or more other therapeutic agents can be used, for example, to: 1) enhance the therapeutic effect(s) of the methods of the present invention and/or the one or more other therapeutic agents; 2) reduce the side effects exhibited by the methods of the present invention and/or the one or more other therapeutic agents; and/or 3) reduce the effective dose of vitamin A or agonist of RARβ of the present invention and/or the one or more other therapeutic agents.

The RARβ (e.g., RARβ2) agonist of the present invention may be used in combination with a second drug for treating hypertriglyceridemia and hyertryglyceridemia associated condition. Non-limiting examples of the second drug may be a fat absorption inhibitors by blocking pancreatic triglyceride lipase in the intestine, such as Orlistat; a thermogenic agent which increases basal metabolism rate and "fat burning", such as thyroid hormones and β3-adrenergic agonists; or an appetite suppressant drug (suppression of food intake), such as serotonin agonists, sympathomimetic agents and leptin.

The RARβ (e.g., RARβ2) agonist of the present invention may be used in combination with a second drug for treating hypercholesterolemia and hypercholesterolemia-associated condition. Non-limiting examples of the second drug may be an HMG-CoA reductase inhibitor (inhibitors for cholesterol biosynthesis; so-called "statins"); a cholesterol absorption inhibitor (such as ezetimibe); a bile acid sequestrant (such as cholestyramine and colestipol); a fibric acid derivative (such as fenofibrate and gemfibrozil); a high dose (3-6 g/day) of niacin; an apolipoprotein inhibitor (such as monoclonal antibodies and antisense oligonucleotides mipomersen and ISIS-APOCIII); a proprotein convertase subtilisin/kexin type 9 (PCSK9) inhibitor (such as monoclonal antibodies alirocumab, evolocumab, bococizumab, RG-7652 and LY3015014, as well as antisense oligonucleotides ALN-PCS02 and SPC5001).

In a particular embodiment of the invention the pharmaceutical composition for use in the present invention is also compatible with physical exercise, a diet and/or dietary therapy approaches to reduce or prevent hypertriglyceridemia and/or hypercholesterolemia. Such diets or dietary therapies relate e.g. to the reduction of caloric intake, fat intake and/or cholesterol intake. In addition, reducing saturated dietary fat may be recommended to reduce total blood cholesterol and LDL in a subject in need thereof according to the present invention. If necessary, other treatments such as LDL apheresis or even surgery (for particularly severe subtypes of familial hypercholesterolemia) may be performed.

Many drugs available to treat diseases have been reported to elevate triglyceride or cholesterol levels in patents. The RARβ (e.g., RARβ2) agonist of the present invention may be used in combination with a second drug used to treat an unrelated condition where the second drug causes a clinically significant level of side effect by increasing triglyceride and/or cholesterol levels in the subject. The second drug includes but is not limited to one selected from the group consisting of diuretics (including thiazide) and loop diuretics; β-blockers (e.g., Atenolol, Bisoprolol, Metoprolol, Nadolol, Propanolol); protease Inhibitors; angiotensin converting enzyme inhibitors; estrogen replacement therapy; oral contraceptives with second and third generation progestogens; estrogen receptor modulators; prednisones, amiodarones; cyclosporine; progestin; anabolic steroids; retinoids; and acitretin; immunosuppressive drugs (such as rapamycin); protease inhibitors (such as ritonavir); indinavir; and nelfinavir; and antipsychotics (such as clozapine).

The amount or suitable dosage of vitamin A or agonist of RARβ depends upon a number of factors, including the nature of the severity of the condition to be treated, the route of administration and the age, weight, general health, and response of the individual subject. In certain embodiments, the suitable dose level is one that achieves this therapeutic response and also minimizes any side effects associated with the administration. For example, vitamin A or agonist of RARβ may be administered at an amount from about 30 mg to about 200 mg per day, e.g., about 50 mg to about 150 mg per day, about 50 to about 100 mg per day, about 100 mg to about 150 mg per day.

Vitamin A or agonist of RARβ may be administered in single or divided or multiple doses. It will be understood that a suitable dosage of vitamin A or agonist of RARβ may be taken at any time of the day or night, with food or without food. In some embodiments, the treatment period during which an agent is administered is then followed by a non-treatment period of a particular time duration, during which the therapeutic agents are not administered to the patient. This non-treatment period can then be followed by a series of subsequent treatment and non-treatment periods of the same or different frequencies for the same or different lengths of time. The expression profile of one or more such genes (e.g., as listed in Table 5 below) may be a therapeutic effect indicator which may be used to direct therapeutic regimen and doses according to the present invention.

The therapeutic effect of vitamin A or retinoic acid receptor-beta (RARβ) agonist may be achieved relatively quickly from about 1 day to about 8 days (e.g., 2 days, 3 days, 4 days, 5 days, 6 days, 7 days) after it is administered to the subject in need, it may take longer time.

The pharmaceutical composition for use in the present invention can be administered when triglyceride, cholesterol and/or glucose levels are already elevated in a subject, but can also be administered in advance, if the triglyceride, cholesterol and/or glucose levels are expected to rise in the near future or if any potential rise of triglyceride, cholesterol or glucose levels would be detrimental for the health and/or status of the patient. In the latter case (detrimental effect) the pharmaceutical composition for use in the present invention is in particular administered to anticipate and prevent peaks of triglyceride, cholesterol and/or glucose levels.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

EXAMPLES

The present description is further illustrated by the following examples, which should not be construed as limiting in any way. The contents of all cited references (including literature references, issued patents, published patent applications as cited throughout this application) are hereby expressly incorporated by reference.

Example 1

Materials and Methods

Cell Culture and Isolation of RARβ Homozygous ES Cell Line. Mouse J1 wild-type ES cells were cultured as described previously (27). C57BL/6 RARβ heterozygous mice were provided by Dr. Pierre Chambon (Strasbourg-Cedex, France) (26). Homozygous RARβ-null mice were obtained following mating of RARβ heterozygous mice. Blastocysts were harvested on day E3.5 and individually cultured on ES cell medium as previously described (28).

Pancreatic endocrine differentiation protocol. A slightly modified version of the established protocols published by Borowiak (14) and D'Amour (15) was used to carry out differentiation of hormone expressing endocrine cells from mouse ESCs. Prior to differentiation, ESCs were seeded at $5 \times 10^5$ on 30 mm gelatin-coated plates. After overnight culture, cells were exposed to 250 nM BIO-Acetoxime (EMD Bioscience, San Diego, Calif.)+50 ng/ml activin A (R&D Systems, Minneapolis, Minn.) in Advanced RPMI (GIBCO, Grand Island, N.Y.) supplemented with 1× L-Glu and 0.2% FBS (GIBCO) for 1 day, and then to activin A alone in the same media. Cells were then cultured for 4 days to induce endoderm differentiation. For pancreatic progenitor induction, the cells were transferred to 50 ng/ml FGF10 (R&D Systems), 7.5 µM cyclopamine (Calbiochem, San Diego, Calif.) in DMEM supplemented with 1× L-Glu, 1× Pen/Strep, and 1× B27 (Invitrogen, Grand Island, N.Y.) for 2 days. At day 7, cells were transferred to FGF10, cyclopamine and 2 µM all-trans RA (Sigma, St. Louis, Mo.) in DMEM supplemented with 1× L-Glu, 1× Pen/Strep, and 1× B27 (Invitrogen) for 4 days. At day 11, cells were cultured in the presence of DMEM supplemented with 1× L-Glu, 1× Pen/Strep, and 1× B27 for 3 days. At day 14, CMRL (Invitrogen) medium was added and supplemented with 1× L-Glu, 1× Pen/Strep, 1× B27, 50 ng/ml IGF-1 (R&D Systems), 50 ng/ml HGF (R&D Systems), and 10 mM nicotinamide (Sigma) for 3 more days. All stock compounds were made in either PBS or ethanol.

RT-PCR analysis. Various markers for endodermal (day 5), pancreatic progenitor (day 11), endocrine progenitor (day 14) and endocrine (day 17) differentiation were analyzed by semi-quantitative RT-PCR in J1 wild-type and RARβ KO ESCs. Specific primers used and amplification conditions are listed in Table-3. Primers were designed around introns whenever possible. Primers not designed around introns are shown in Table 1 with an asterisk. Total RNA extraction, semi-quantitative and quantitative PCR reactions were performed as previously described (18). Amplified PCR products were resolved on 1.5% agarose gels and visualized by staining with ethidium bromide. PCR bands were sequenced for verification of the correct amplicon. Quantitation of semi-quantitative gels was performed using ImageJ software (National Institutes of Health) from three experimental biological repeats.

TABLE 3

Primer sequences used for RT-PCR
All primers for RT-PCR are designed around introns, except those marked with *.

| Primer | Application | Forward sequence (5'→3') | Reverse sequence (5'→3') | Product size (bp) |
|---|---|---|---|---|
| mIns1 | RT-PCR | TAGTGACCAGCTATAATCAGAG (SEQ ID No. 1) | ACGCCAAGGTCTGAAGGTCC (SEQ ID No. 2) | 289 |
| mGcg | RT-PCR | CGCCGTGCCCAAGATTTT (SEQ ID No. 3) | CCTGCGGCCGAGTTCCT (SEQ ID No. 4) | 232 |
| mSst* | RT-PCR | GAGCCCAACCAGACAGAGAA (SEQ ID No. 5) | GAAGTTCTTGCAGCCAGCTT (SEQ ID No. 6) | 150 |
| mNgn3* | RT-PCR | CTGCGCATAGCGGACCACAGCTTC (SEQ ID No. 7) | CTTCACAAGAAGTCTGAGAACACCAG (SEQ ID No. 8) | 233 |
| mRARβ | RT-PCR | GATCCTGGATTTCTACACCG (SEQ ID No. 9) | CACTGACGCCATAGTGGTA (SEQ ID No. 10) | 248 |
| mNanog | RT-PCR | AAAGGATGAAGTGCAAGCGGTGG (SEQ ID No. 11) | CTGGCTTTGCCCTGACTTTAA (SEQ ID No. 12) | 520 |

TABLE 3-continued

Primer sequences used for RT-PCR
All primers for RT-PCR are designed around introns, except those marked with *.

| Primer | Application | Forward sequence (5'→3') | Reverse sequence (5'→3') | Product size (bp) |
|---|---|---|---|---|
| mRex1 | RT-PCR | GAAAGCAGGATCGCCTCACTGTGC (SEQ ID No. 13) | CGATAAGACACCACAGTACACAC (SEQ ID No. 14) | 641 |
| mCyp26a1 | RT-PCR | GAAACATTGCAGATGGTGCTTCAG (SEQ ID No. 15) | CGGCTGAAGGCCTGCATAATCAC (SEQ ID No. 16) | 272 |
| mPax-6 | RT-PCR | GCAACCCCAGTCCCCAGTCAGA (SEQ ID No. 17) | AGTCCATTCCCGGGCTCCAGTTCA (SEQ ID No. 18) | 399 |
| mIsl-1* | RT-PCR | CCCGGGGGCCACTATTTG (SEQ ID No. 19) | CGGGCACGCATCACGAA (SEQ ID No. 20) | 397 |
| mIapp* | RT-PCR | TGGGCTGTAGTTCCTGAAGC (SEQ ID No. 21) | GCACTTCCGTTTGTCCATCT (SEQ ID No. 22) | 199 |
| HPRT1 | RT-PCR | TGCTCGAGATGTGATGAAGG (SEQ ID No. 23) | TCCCCTGTTGACTGGTCATT (SEQ ID No. 24) | 192 |

Indirect Immunofluorescence. Immunofluorescence assays on cells and tissue sections were performed as previously described (29). Briefly, differentiated samples were fixed using 4% (w/v) paraformaldehyde and membrane permeabilization (for cells only) was done with 0.3% (w/v) Triton-X 100 (Sigma). Unspecific sites were blocked using 2% BSA for 30 min prior to incubation with rabbit polyclonal anti-PDX1 (Millipore, 06-1379, 1:1000), rabbit anti-C-Peptide (Cell Signaling, 4593, 1:500, Danvers, Mass.) and mouse monoclonal anti-Glucagon (Abcam, ab10988, 1:200) primary antibodies. Phalloidin-TRITC (Millipore, FAK100, 1:1000, Billerica, Mass.) was used to stain the actin stress fiber network (F-actin). Nuclei were stained using DAPI contained in Vectashield® mounting medium for fluorescence (Vector labs, Burlingame, Calif.). Quantitation of C-peptide positive stained cells and islet surface area was performed using NIS-Elements Advanced Research software (Nikon).

Western blot analysis. Proteins were extracted from mouse pancreas, separated by SDS-PAGE, and transferred onto nitrocellulose membranes as previously described (30, 31). Membranes were blocked in PBS containing 5% skim milk and 0.1% TWEEN 20 (BioRad, Hercules, Calif.). Rabbit anti-C-Peptide (Cell Signaling, 4593, 1:500), mouse monoclonal anti-Glucagon (Abcam, ab10988, 1:500) and anti-actin (Millipore, MAB1501, 1:2000) primary antibodies were incubated with membranes overnight at 4° C.

Mouse Blood Glucose Assays. C57BL/6 WT and RARβ KO mice were used for this experiment as previously described (26). Briefly, mice were fasted for 15 hours overnight and a 50% dextrose solution (2 g/kg body weight) was injected intraperitoneally. Blood glucose levels were measured from the tail vein at 0, 15, 30, 60, and 120 min using the One Touch Blood Glucose Monitoring System (LifeScan) (32).

Statistical analysis. All experiments were performed at least 3 times (n>3) using independent biological triplicates. Results were presented as means±SEM. All statistical tests were performed using GraphPad InStat software version 3.10. A p-value of ≤0.05 indicated statistical significance.

Example 2

Pancreatic Differentiation and Assessment of Pancreatic Markers in WT Mouse ES Cells The endocrine differentiation protocol was selected because it included RA-treatment at day 7 and also showed expression of later stage endocrine markers using human ES cells (15). The D'Amour et al. (2006) pancreatic differentiation protocol was used with some slight modifications to generate pancreatic endocrine cells in culture through the use of specific growth factors (FIG. 1A). The first modification replaced Wnt3a with BIO-acetoxime (BIO). Wnt3a has been documented as being important for mesendoderm specification and BIO-acetoxime is a selective inhibitor of GSK-3β which indirectly acts as a Wnt3a agonist during cell differentiation (33, 34). Second, nicotinamide was included during the last stage of differentiation because various published protocols included this reagent due to strong evidence for its efficacy in pancreatic differentiation (35, 36).

To characterize the impact of the differentiation protocol on pancreatic endocrine specification in WT ES cells, cellular extracts were harvested at various time points during the procedure (FIG. 1B). The mRNA levels of various differentiation markers were assessed by RT-PCR for the different experimental conditions. LIF withdrawal combined with the addition of BIO and Activin A to the culture system caused a drastic decrease in the levels of ES cell markers Nanog and Rex1 (FIG. 1B, lane 6) compared to untreated and RA-treated ES cells (FIG. 1B, lanes 1 to 4). Such a phenomenon was observed throughout the subsequent phases of the differentiation protocol (FIG. 1B, lanes 7 to 12). While robust expression of glucagon, a functional marker of α-cells (37), was observed by day-14 (FIG. 1B, lane 8), somatostatin, a hormone secreted by δ-cells (37), was detectable as early as day-5 (FIG. 1B, lane 6). Insulin-1 (β-cell marker)(37) was detected by day-11 of the differentiation protocol but its expression fluctuated depending on the uses of HGF, IGF1, or both factors together during the endocrine cell differentiation stage (FIG. 1B, lanes 9 to 11). The most consistent expression of all 3 pancreatic endocrine differentiation markers tested was observed by combining HGF and IGF1 with nicotinamide, from day-14 to 17 (FIG.

1B, lane 12). Even though keeping ES cells in culture, at confluence and in absence of LIF for 17 days, caused a decrease in Nanog and Rex1 expression, such conditions failed to induce any of the differentiation markers tested (FIG. 1B, lane 5).

These observations confirm the conversion of ES cells to endocrine cells able to express pancreatic hormone-encoding genes, according to a method described previously (15). Such a biological model represents a powerful tool to investigate the role of RARβ at specific stages of pancreatic endocrine differentiation.

Example 3

RAR Knockout Delays Pdx1 Expression in Pancreatic Endocrine Differentiation

Figure 2A:
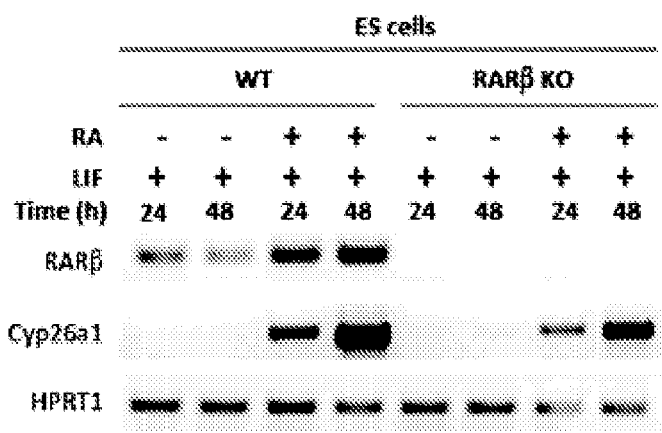
FIG. 2: Impact of RARβ deletion on Pdx1 expression through pancreatic endocrine differentiation process. (A) RT-PCR analysis confirming the suppression of RARβ in KO ES cells. Analysis of Cyp26a1, a RA-responsive gene, demonstrates the presence of RA signaling activity via other receptors in RARβ KO cells. HPRT1 was used as a control housekeeping gene. (B) Indirect immunofluorescence staining for Pdx1 (green) in WT and RARβ KO, at 5, 11, 14, and 17 days in the absence (untreated) or in the presence (treated) of growth factors used in the differentiation protocol. Cells were counterstained using rhodamine-conjugated phalloidin, which binds to F-actin (red) and nuclei were stained with DAPI (blue) (Bars=50 μm).

As previously mentioned, the RA signaling, including the participation of RARβ, was suggested to be crucial for the onset of pancreatic endocrine differentiation (11, 20, 21, 24). In order to study the specific role of RARβ in such a process, WT and RARβ KO mouse ES cells were subjected to the endocrine differentiation protocol described above. RT-PCR analysis confirmed the absence of RARβ transcript in KO cells (FIG. 2A). The RARβ2 isoform, like Cyp26a1, represents a RA-inducible gene (38). This explains why stronger RARβ signal was observed in the presence of RA, in WT cells compared to untreated ones (FIG. 2A). RA-dependent Cyp26a1 expression was observed in both WT and RARβ KO ES cells, suggesting that KO cells are still responding to RA stimuli (FIG. 2A). Using this model of RARβ deletion, the inventors sought to determine the impact of such a retinoid receptor on the expression of Pdx1, which consists in a master regulator of pancreatic cell fate (39-41).

Figure 2B:
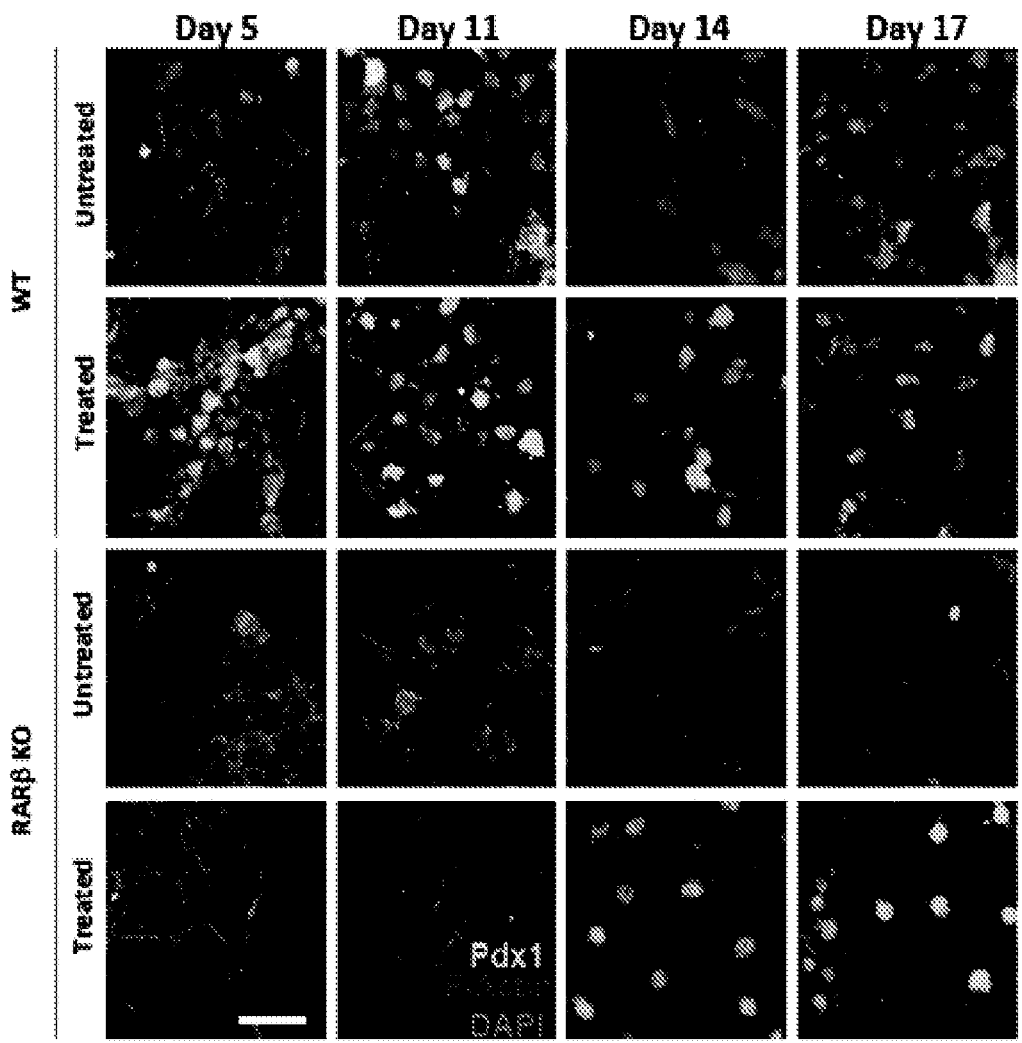

WT and RARβ KO ES cells were differentiated into pancreatic endocrine cells, as described in FIG. 1, and indirect immunofluorescence staining for Pdx1 was performed at the different stages of the protocol (FIG. 2B). Pdx1 expression was observed in WT differentiating cells by day-5, and was still present at all the other stages tested in a heterogeneous pattern (FIG. 2B). In contrast, Pdx1 protein was absent from nuclei of differencing cells at day-5 and 11, and was only detected by day-14 of the protocol in RARβ null cells (FIG. 2B).

These observations suggest that the absence of RARβ in this cell culture system undergoing pancreatic differentiation engenders a delay in the induction of Pdx1, which could potentially affect subsequent key steps of endocrine specialization.

Example 4

Absence of RARβ Expression Impairs the Global Pancreatic Endocrine Differentiation Process Considering the finding that RARβ deletion in ES cells delays the expression of Pdx1 during their specialization into pancreatic endocrine cells, the inventors decided to further investigate the impact of such a phenomenon on early, intermediate, and late molecular genetic events throughout the differentiation process. As reported in many studies on reprogramming, decreased expression of pluripotency factors, including Nanog, in ES cells is essential for proper differentiation (42). Nanog levels were previously shown to decrease around day-5 during the pancreatic endocrine differentiation protocol (FIG. 1B). A comparison of Nanog transcript levels in WT and RARβ KO differentiating cells, showed a sustained expression of this pluripotency factor in KO cells while it is severely repressed in WT controls (FIG. 3A). On the other hand, the expression of Neurogenin-3 (Ngn3), a master transcription factor during onset of pancreatic endocrine lineages (39, 41, 43), displayed a phased induction pattern in WT cells but was not induced in RARβ knockout (FIG. 3A).

Like Ngn3, Paired-box 6 (Pax6) and Islet1 (Isl-1) represent two important transcription factors in pancreatic islet cell differentiation, which are expressed from intermediate ("'mid'") to terminally differentiated ("'late'") stages (39, 40, 44, 45). While no difference were noted for Pax6 expression patterns, Isl-1 displayed a delayed expression peak in RARβ KO cells as compared to WT (day-14 versus day-11) (FIG. 3B).

Finally, the expression of different functional endocrine differentiation markers such as, glucagon (Gcg; α-cells), insulin-1 (Ins1; β-cells) and islet amyloid polypeptide (IAPP; β-cells) was analyzed in RARβ KO and WT differentiating cells (15, 46, 47) (FIG. 3C). In all cases, RARβ KO cells showed impaired expression of those functional markers as compared to WT (FIG. 3C). Specifically, by day-17 Gcg, Ins1, and Iapp respectively presented ~5-fold (p=0.04), ~120-fold (p=0.013), and ~7-fold (p=0.0002) increases in WT differentiated cells as compared to RARβ KO (FIG. 3C). Somatostatin (Sst), a functional marker of δ-cells (37) also displayed a decreased expression in RARβ deficient cells (not shown).

Taken together, these observations show that RARβ and retinoid signaling play a central role in pancreatic endocrine differentiation by regulating the expression of certain master genes at early and intermediate stages of the specialization process, which as a result impairs the expression of functional markers of pancreatic islet cells.

Example 5

Figure 3:
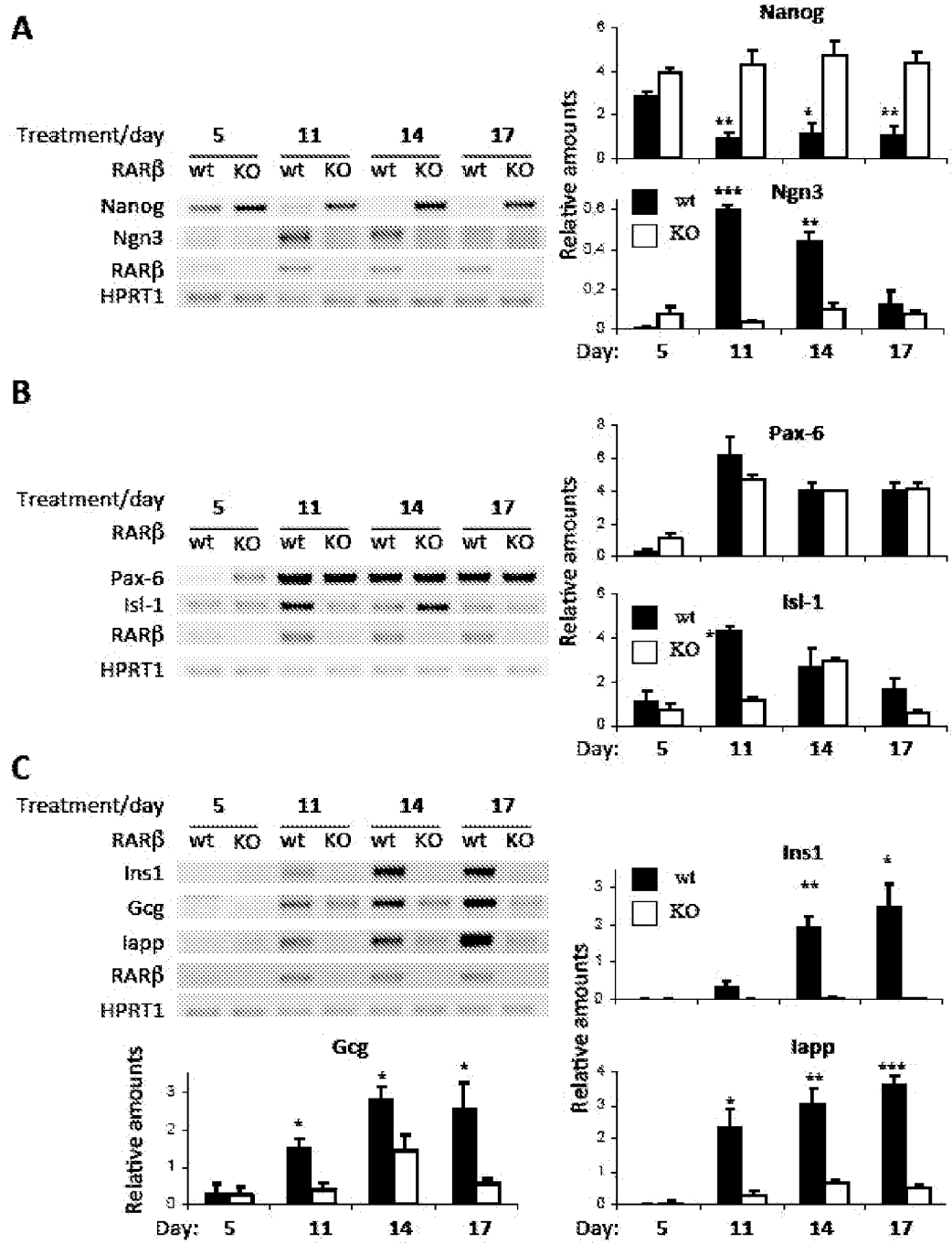
FIG. 3: Expression of pancreatic differentiation markers in WT and RARβ knockout (KO) ES cells. Transcript expression analyses of (A) early, (B) mid, and (C) late stage endocrine pancreatic differentiation markers in WT and RARβ KO ES cells. RT-PCR amplification of (A) Nanog, Ngn3, (B) Pax6, Is1-1, and (C) Ins1, Gcg, and Iapp mRNA was performed in both cell lines at 5, 11, 14, and 17 days of the differentiation protocol. In each case, RARβ expression was monitored in both cell lines and HPRT1 was used as a control housekeeping gene. Relative amounts, normalized to HPRT1 levels for each marker tested, are shown in histograms (n=3; *: p≤0.05; : p≤0.0079; *: p≤0.0003).
Figure 4A:
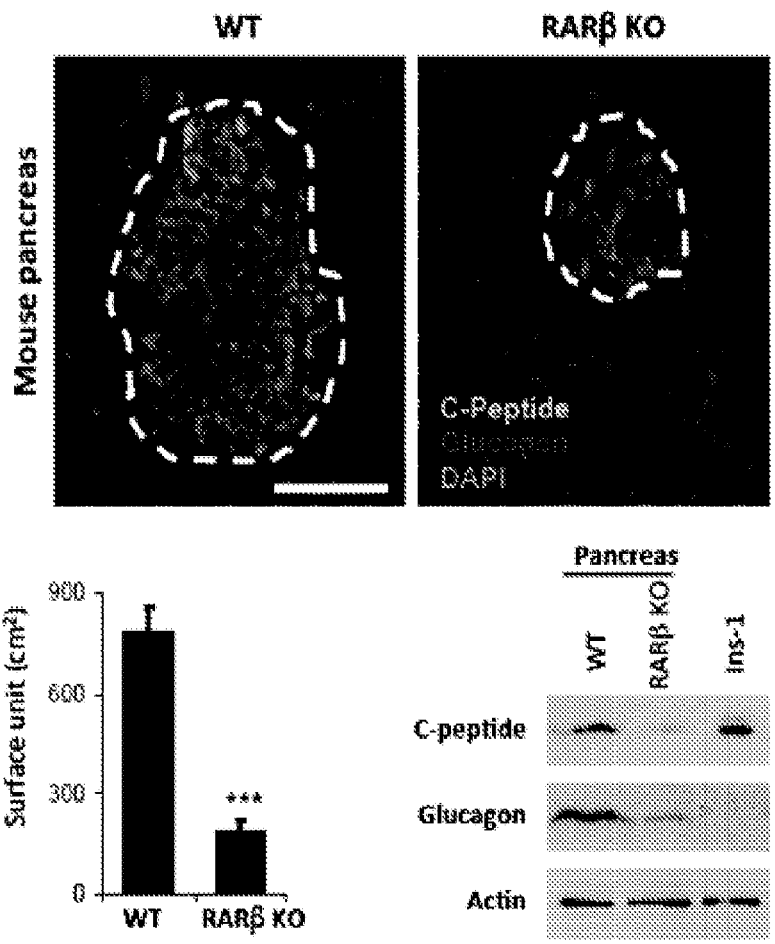
FIG. 4: In vivo characterization of RARβ deletion on islets of Langerhans functionality and glucose metabolism. (A) Indirect immunofluorescence staining of C-peptide (green) and Glucagon (red) on C57BL/6 WT and RARβ KO mouse pancreas tissue sections. Pancreatic islet-corresponding regions were circled by dashed lines and nuclei were marked with DAPI (blue) (bars=50 μm). Islet size were quantified per surface area units ($cm^2$), with respect to high resolution micrographs, for each group and presented as histogram (n=6; **: p=0.031). Western blot analysis of C-peptide and Glucagon expression was performed on WT and RARβ KO mouse pancreas protein extracts. Ins-1 cells were used as positive control for C-peptide expression, while immunodetection of actin was used as a loading control. (B) Blood glucose concentration (mg/dL) in WT and RARβ null, knockout mice after 15 h fasting (left) (n≥5; p=0.0011). Blood glucose clearance (right) for WT (♦) and RARβ KO (■) mice was measured following a 2 mg/kg dextrose i.p. injection. Relative blood glucose levels were assessed at 0, 15, 30, 45, 60, and 120 minutes post-injection (n≥6; *: p=0.0137; : p≤0.0064; *: p<0.0001).

Deletion of RARβ Affects In Vivo Glucose Metabolism and Pancreatic Islet Functionality The tissue culture system used to study diverse steps of pancreatic endocrine differentiation provided important insights about the role played by RARβ in such a physiological process. Specifically, the absence of RARβ expression leads to decreased or delayed expression of crucial transcription factors involved in islet cell differentiation, as well as decreased expression of functional differentiation markers (FIGS. 2 and 3). Thus, the inventors sought to validate the relevance of this finding in an in vivo model. A classical KO of both RARβ alleles in mice, generated and characterized by Ghyselinck et al. (26), was used to study the impact of such a deletion on pancreatic endocrine functions. By extracting pancreas from WT and RARβ-deficient mice, and performing indirect immunofluorescence staining for C-peptide, a by-product of insulin biosynthesis (48), and glucagon, the inventors observed a decrease (~75%, p<0.0001) in the size of KO mice islets as compared to WT (FIG. 4A). Western blot analysis confirmed the decrease in C-peptide and glucagon expression in RARβ KO mice pancreas extracts as compared to WT controls (FIG. 4A). These observations demonstrate that RARβ KO mice display decreased pancreatic endocrine islet cell production and/or maintenance, which could have major, deleterious effects on glucose metabolism.

Figure 4B:
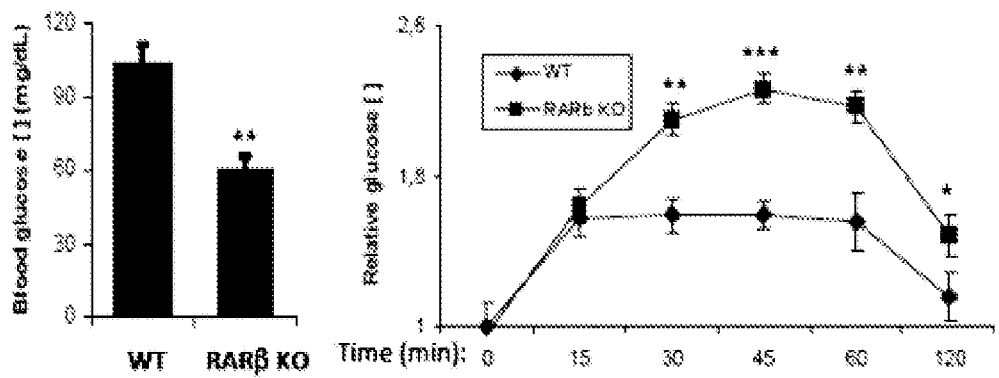

To assess the systemic effects of RARβ deletion on reduced insulin and glucagon-producing cells, mice of both groups were fasted for 15 hours and blood glucose concentration was measured. While blood glucose levels in WT were normal (between 70 and 105 mg/dL) (49), RARβ KO animals were found to be in a hypoglycemic state, slightly below normal levels (61±4.7 mg/dL) (FIG. 4B) (50). In order to test the functionality of β-cells in both mice groups, a time-course blood glucose reading experiment was performed which an intraperitonial injection of 2 mg/Kg (body weight) dextrose at time ""0"". Then, blood glucose clearance was monitored at 0, 15, 30, 45, 60, and 120 minutes in WT and RARβ KO mice. We observed that blood glucose was metabolized faster in WT mice, as compared to KO (FIG. 4B). Moreover, the average blood glucose levels in RARβ KO mice 120 min after the dextrose injection was significantly higher (~30%, p=0.014) than in WT group, suggesting a lower glucose tolerance in animals lacking such a retinoid receptor (FIG. 4B).

As described in the Examples, by using an ES cell-based directed differentiation system (Examples 2-4) and an in vivo gene knockout model (Example 5), the inventors demonstrated the crucial role for RARβ in proper pancreatic endocrine cell differentiation. In both cases, the absence of RARβ led to a decrease in terminal differentiation and functional markers, such as insulin and glucagon production. In mice, RARβ deletion resulted in impaired glucose metabolism, characterized by hypoglycemia and glucose intolerance. Taken together, these findings indicate that reduced RARβ and retinoic acid signaling are key factors in glucose metabolism disorders, such as diabetes mellitus type I and II. Hence, the administration of agonists of the RARβ receptor can prevent or treat such disorders.

The study described in Example 2 leads to the conclusion that Pdx1 expression, during the pancreatic differentiation process, was delayed in the absence of RARβ (FIG.-2). Such a transcription factor represents a key player in the early determination of pancreatic progenitors and bud expension (39, 40, 51, 52). A previous study reported that RA directly induces Pdx1 expression in ES cells (51). Strengthening such a statement, ChIP-chip analyses performed on F9 teratocarcinoma cells revealed the presence of a putative retinoic acid response element (RARE) located at ~3 kb upstream of the transcription start site of Pdx1 (not shown). That Pdx1 expression is delayed but not fully suppressed in RARβ-null ES cells opens a door on possible compensatory mechanisms exerted by other RARs. It has been previously noted that RARβ transcript levels are increased at stages of endocrine differentiation, while a peak of RARα expression is associated with late differentiation stages (24). Possibly RARα and β together participate in the Pdx1 biphasic expression pattern, as reviewed by Soria (39). Thus, suppressing RARβ would result exclusively in a late Pdx1 expression as observed in treated RARβ KO cells (FIG. 2).

Pdx1 mis-expression was previously associated with severe β-cell dysfunction and increased cell death (53). Accordingly, RARβ KO caused a reduction in β-cell terminal differentiation markers' expression, such as Ins1 and Iapp in the cell culture system (FIG. 3), as well as a decreased number of C-peptide expressing cells in RARβ null-mice pancreatic islets (FIG. 4). Recent findings by Dalgin et al. (54) also linked RA signaling and endocrine cell fate. Although the authors claimed that β-cell progenitors differentiate as α-cells in RA downstream target mnx1 morphants, the data reported here suggest that RARβ KO induces a decrease in α-cell differentiation, characterized by reduced expression of glucagon in the cell culture system (FIG. 3) and RARβ null mice (FIG. 4). Thus, the effect observed on islet cells in the absence of RARβ could be attributed to the role of RA signaling in early pancreatic differentiation events rather than lineage-specific terminal differentiation.

Like Pdx1, the bHLH transcription factor Neurogenin3 (Ngn3) constitutes another key player in the commitment of endoderm to pancreatic precursors (40, 43, 47). Among the cascade of transcription factors involved in pancreas development, Ngn3 is the earliest to be expressed in the endocrine differentiation pathway (40, 55). While no links between RA signaling and Ngn3 expression was reported in the literature, RARβ KO cells displayed decreased levels of this transcription factor during pancreatic differentiation (FIG. 3). Thus, the impact of RARβ deletion on Ngn3 could be indirect and involving the participation of intermediate factors.

Pax6 and Isl-1 represent two major transcription factors having a role in endocrine lineage specification after bud formation (45, 56) Considering that Pax6 expression is not affected by RARβ KO, and that the Isl-1 peak of expression is only delayed by such a deletion, it appears that absence of RA signaling through RARβ is insufficient to completely abrogate endocrine differentiation, but may lead to significant defects in islet cell function.

The observations reported here indicate that the absence of RARβ expression impairs development and maintenance of pancreatic islets in vivo (FIG. 4). In mammals, glucose intolerance is characterized by sustained high blood glucose levels (above 140 mg/dL) during at least two hours, while hypoglycemia is decreed when blood concentration goes below 70 mg/dL (50, 57). Blood glucose assessment 1) after 15 h fasting and 2) upon dextrose injection led us to suggest that RARβ-null mice have a predisposition to fasting hypoglycemia and increased glucose intolerance, two conditions associated with diabetes mellitus (58).

Close correlations have been made between dietary habits and diabetes, especially for type II (59). Considering the role of RARβ in pancreatic endocrine cell differentiation, and that the RARβ gene itself is up-regulated by retinoic acid, a sustained vitamin A deficient diet could lead to insufficient islet cell turnover, and eventually to diabetes. RARβ expression is also known to depend on epigenetic regulation (60, 61). For instance, aberrant hypermethylation of various promoter elements was reported in different pancreatic disorders such as cancer, diabetes, and chronic pancreatitis (62-64). Therefore, epigenetic silencing of RARβ or other associated effectors could play a role in the onset of certain cases of diabetes.

The production of insulin secreting endocrine cells from ES cells using RA-based protocols is proposed as a promising tool for diabetic therapy (9). However, ensuring accurate vitamin A consumption and proper RA signaling via RARβ represent new avenues to prevent or treat diabetic disorders. In particular, the administration of an RARβ agonist would be a specifically targeted method of enhancing this RARβ signaling to prevent or treat diabetic disorders. Taken together, these findings shed light on the role of RARβ in pancreatic endocrine differentiation, which consequently affects in vivo blood glucose metabolism.

Example 6

RARβ Agonist Treatment Preparation

Preparation of AC261066 (a RARβ agonist from Tocris) solution. AC261066 was dissolved in dimethyl sulfoxide (DMSO) at the concentration of 1.5 mg/ml and 3.0 mg/ml, and diluted in the drinking water for mice to the final concentration of 1.5 mg/100 ml and 3.0 mg/100 ml.

Mice, diet, and drug treatment. WT male C57/BL6 male mice were maintained on either a standard laboratory chow-fed diet (CFD) with 13% kcal fat, (diet #5053, Lab Diet, Inc, St. Louis, Mo.) or a high fat, western style diet (HFD) with 60% kcals from fat, (diet #58126, Lab Diet, Inc., St. Louis, Mo.) for 4 months. One month after the start of the high fat diet treatment, the high fat diet group was further split into 2 groups for 3 months: i) high fat diet and the drinking water containing 1% DMSO; ii) high fat diet and the drinking water containing 1.5 mg/100 ml AC261066, a specific RARβ agonist. Then mice were sacrificed by cervical dislocation. Blood and various tissue samples were harvested.

Example 7

Pancreas

Semi-Quantitate PCR. Total RNA was extracted from mouse tissues using TRIzol reagent (Life technologies) and (1 µg) was used to synthesize cDNA. cDNA synthesis was performed at 42° C. for 1 h in a final volume of 20 µl using qScript (Quanta, Md.). Semi-quantitative PCR were performed Taq DNA polymerase (Invitrogen, CA). Three step PCR was run as follows: 94° C. for 30 s, 58-64° C. for 45 s for primer annealing and 72° C. for 1 min for primer extension. The number of cycles for each primer pair for amplification in the linear range was determined experimentally. PCR products were resolved on 2% agarose gels and visualized by staining with ehtidium bromide. Primers for gene expression used were as follows: RARβ2, F: 5'-TGG-CATTGTTTGCACGCTGA-3' (SEQ ID No. 25), R: 5'-CCCCCCTTTGGCAAAGAATAGA-3' (SEQ ID No. 26), CYP26A1, F: 5'-CTTTATAAGGCCGCCCAGGTTAC-3' (SEQ ID No. 27), R: 5'-CCCGATCCGCAATTAAA-GATGA-3' (SEQ ID No. 28), LRAT, F: 5'-TCTGG-CATCTCTCCTACGCTG-3' (SEQ ID No. 29), R: 5'-GTTCCAAGTCCTTCAGTCTCTTGC-3' (SEQ ID No. 30), INS2, F: 5'-TGTGGGGAGCGTGGCTTCTTCT-3' (SEQ ID No. 31), R: 5'-CAGCTCCAGTTGTGC-CACTTGT-3' (SEQ ID No. 32), HPRT, F: 5'-TGCTCGAGTGTGATGAAGG-3' (SEQ ID No. 33), R: 5'-TCCCTGTTGACTGGTCATT-3' (SEQ ID No. 34).

Analysis of pancreatic retinoids. The frozen pancreas tissue samples (~100 mg) were homogenized in 500 µl cold phosphate-buffered saline (PBS). In addition, 100 µl serum was diluted in cold PBS to total volume of 500 µl. Retinyl acetate was added to each sample before the retinoid extraction for the calculation of extraction efficiency. The retinoids were extracted into 350 µl of organic solution (acetonitrile/butanol, 50:50, v/v) in the dark. The high performance liquid chromatography (HPLC) was performed using a Waters Millennium system (Waters). Each sample (100 µl of the 350 µl) was loaded onto an analytical 5-µm reverse phase C18 column (Vydac, Hesperia, Calif.) and eluted at a flow rate of 1.5 ml/min. Two mobile phase gradient systems were used. Retinoids were identified by HPLC based on two criteria: an exact match of the retention times of unknown peaks with those of authentic retinoid standards and identical UV light spectra (220-400 nm) of unknowns against spectra from authentic retinoid standards during HPLC by the use of a photodiode array detector. The amounts of retinoids were calculated from the areas under the peaks detected at the wave-length of 325 nm. The levels of retinol and retinyl esters were normalized to the tissue weight.

4-hydroxynonenal (4-HNE) staining. Paraffin-embedded sections (from two to four mice per group) were deparaffinized and rehydrated, and antigen retrieval was performed using an antigen unmasking solution (Vector Laboratories, H-3300). After quenching endogenous peroxidase with 3% $H_2O_2$, the tissue sections were blocked with the blocking reagent (from the M.O.M. kit from Vector Laboratories). Then, tissue sections were incubated with a 4-HNE antibody (1:400; mouse monoclonal antibody; Abcam, ab48506) overnight at 4° C. The sections were then incubated with secondary antibodies (1:200, anti-mouse IgG from the M.O.M kit). As a negative control, sections were stained without incubation with primary antibodies. The signals were visualized based on a peroxidase detection mechanism with 3,3-diaminobenzidine (DAB) used as the substrate.

Figure 5:
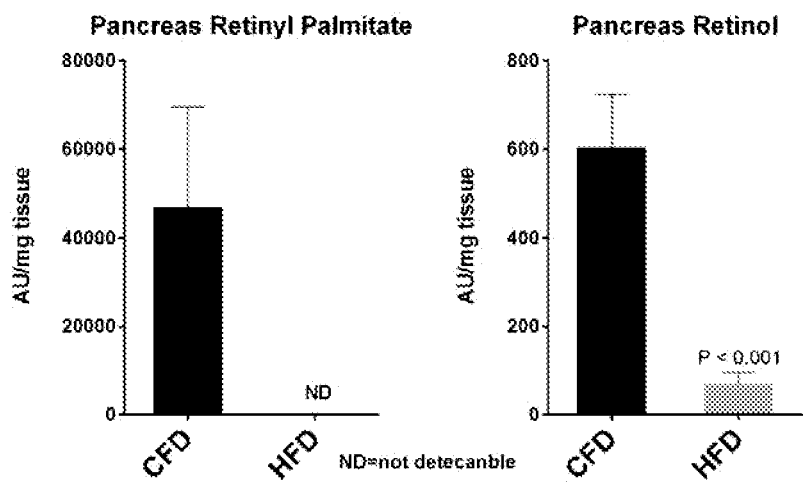
FIG. 5. Retinoid levels in mouse pancreas following the treatment indicated. Con fed diet (CFD) (n=5); HFD (n=5). Mice fed a high fat diet/obese mice have almost no retinoids in the pancreas compared to mice on a control, normal chow diet. They exhibit an organ specific vitamin A deficiency.

Retinoid levels in pancreatic tissue. Our HPLC analysis revealed that that pancreata from HF-fed obese mice had dramatically decreased levels retinol (VA, vitamin A) compared to CF (control diet) controls (FIG. 5). Retinyl palmitate was undetectable in pancreata tissue from HF-fed mice (FIG. 5), showing profound pancreas vitamin A deficiency.

Figure 6:
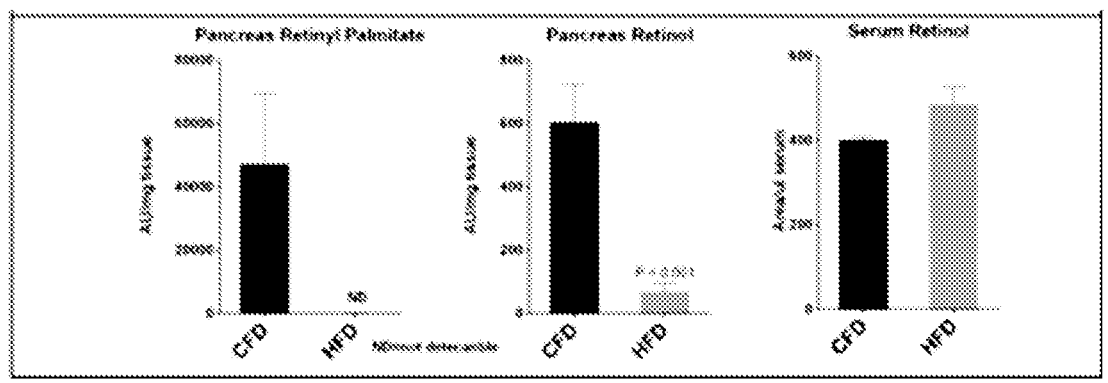
FIG. 6. Serum retinol from mice on a high fat diet vs. control diet compared to the pancreas retinol and retinyl palmitate levels from mice on a high fat vs. control diet. The serum retinol levels are similar or a bit higher in the HF diet mice, but the pancreas retinol levels are much lower in the HF diet mice, showing vitamin A deficiency in the pancreas even in the presence of normal serum vitamin A.

Serum retinol from mice on a high fat diet vs. control diet compared to the pancreas retinol and retinyl palmitate levels from mice on a high fat vs. control diet. The serum retinol levels are similar or a bit higher in the HF diet mice, but the pancreas retinol levels are much lower in the HF diet mice, showing vitamin A deficiency in the pancreas even in the presence of normal serum vitamin A (FIG. 6).

Figure 7:
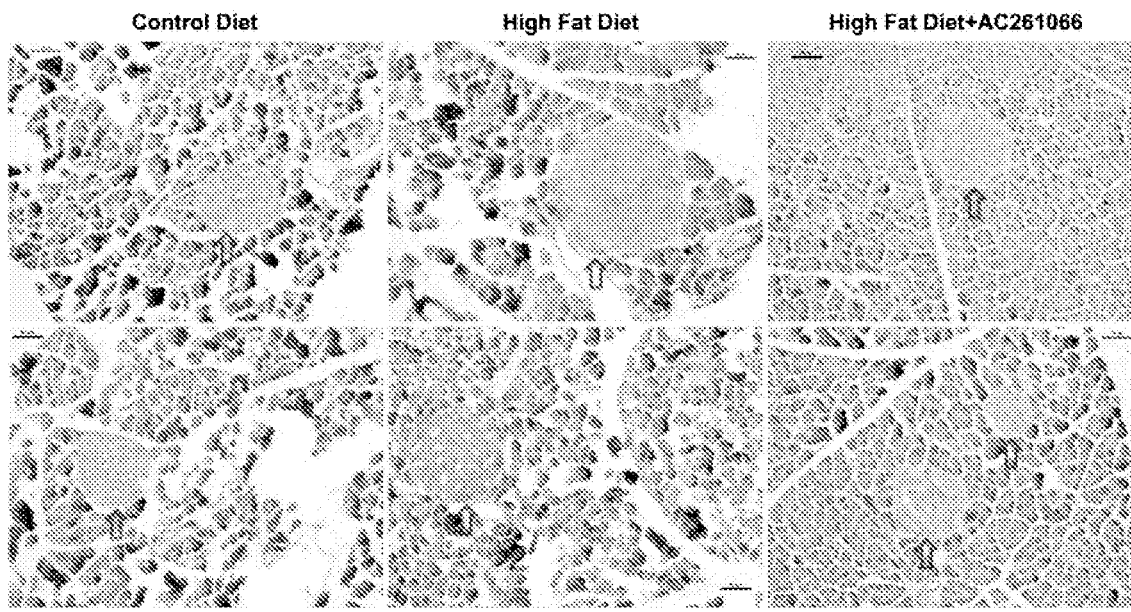
FIG. 7. 4-hydroxynonenal (4-HNE), an indicator of oxidative stress, in the pancreas. The pancreas samples were fixed, embedded in paraffin, and sectioned. Then the tissue sections were stained with an antibody against 4-HNE (magnification, 200×). Sections from two mice/group were photographed and analyzed. The arrows indicate the pancreatic islets. AC261066 reduces oxidative stress in the pancreatic islets in mice on a high fat diet (HFD+AC261066).

AC261066 decreases oxidative stress levels in the pancreas from HF-fed mice. High fat diet results in excessive reactive oxygen species (ROS) production that triggers inflammatory responses and subsequent injuries in many tissues. Therefore, we examined the levels of 4-hydroxynonenal (4-HNE), an α,β-unsaturated hydroxyalkenal that is produced by lipid peroxidation in cells during oxidative stress, and is a marker of oxidative stress caused by reactive oxygen species (ROS) in the pancreas. The pancreatic islets from HF-fed mice showed an increase in the 4-HNE levels compared to the chow-fed controls (FIG. 7). The pancreatic islet samples from the high fat diet plus AC261066 group exhibited markedly lower 4-HNE staining intensity levels compared to HF-vehicle treated mice (FIG. 7).

Figure 8:
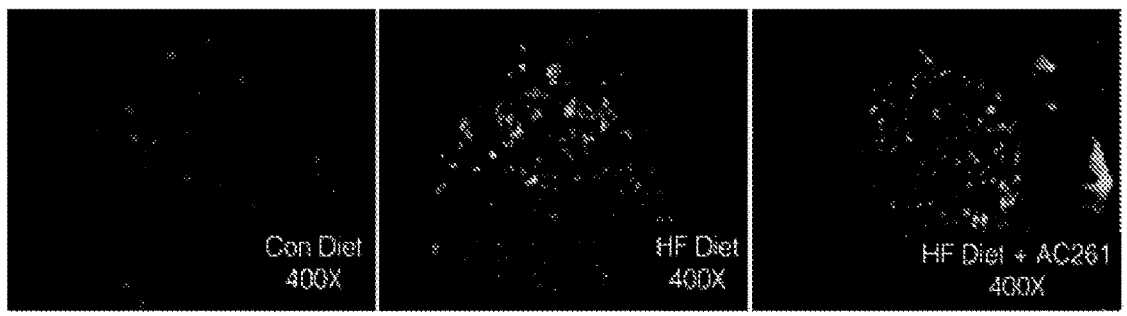
FIG. 8. AC261066 slightly reduces expression of c-peptide (marker of insulin secretion stress) in islets of HF fed mice. Representative immunofluorescence stained pancreatic sections from wild type (wt) male C57/BL6 mice fed either chow control diet (Con), high fat (HF) diet, HF diet plus AC261066 for 4 months. Con Diet (n=5); HF diet (n=5); HF Diet+AC261066 (n=5). Blue, nuclei of cells; red, glucagon; green, c-peptide.

AC261066 does diminish pancreatic islet insulin expression. Next we examined the changes to pancreatic expression of endocrine hormones in CF, HF and HF+AC261066 fed mice. Pancreatic islets stained for pro-insulin c-peptide (green) and glucagon (red) revealed that islets from HF and HF+AC261066 fed mice showed a marked increase in c-peptide staining compared to control diet controls (FIG. 8). AC261066 slightly decreased c-peptide level in the HF diet mice.

Figure 9:
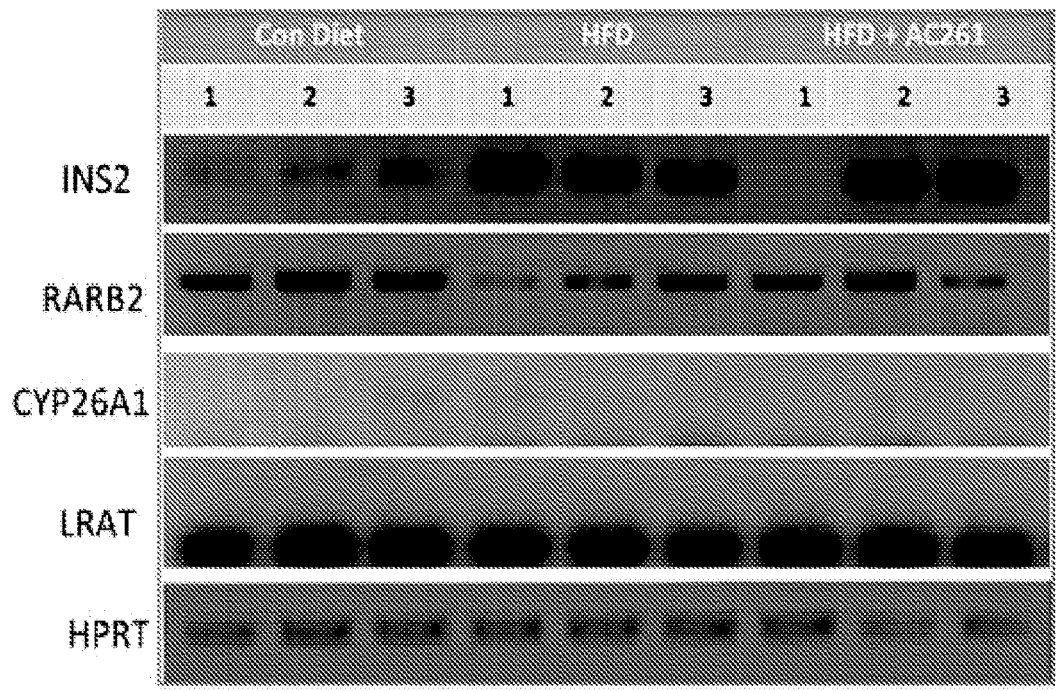
FIG. 9. Gene expression of INS2, RARB2, CYP26A1 and LRAT in pancreatic tissue from wild type (wt) male C57/BL6 mice fed either chow control diet (Con), high fat (HF) diet, HF diet plus AC261066. Cyp26 and LRAT, no detectable signal. HPRT, loading control. RAR β2 mRNA levels were decreased by the high fat diet compared to the control diet (con), consistent with the vitamin A deficiency in the pancreas. AC261066 increased the RAR β2 mRNA levels in the HF diet mice.
Figure 10:
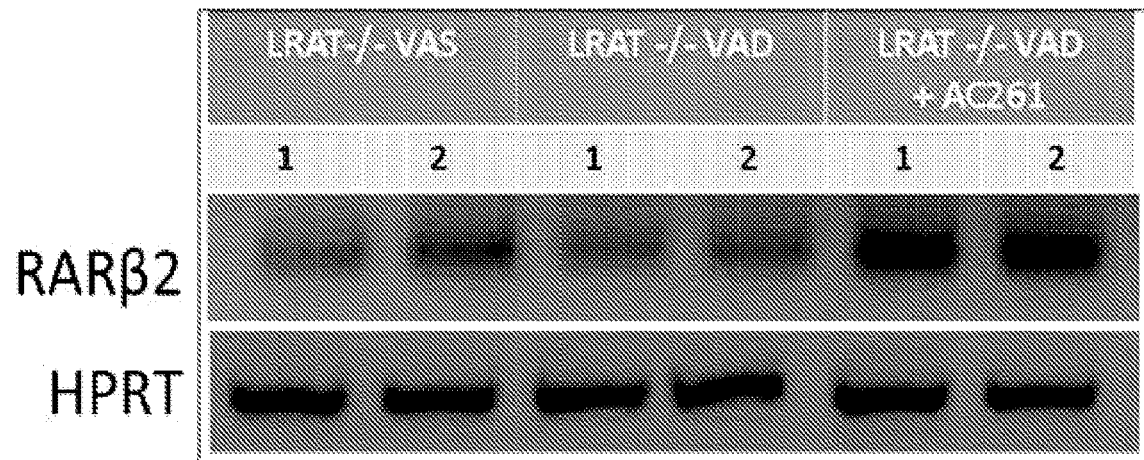
FIG. 10. Gene expression of RARβ2 in pancreatic tissue from LRAT −/− vitamin A sufficient mice (VAS, normal control diet), LRAT −/− vitamin A deficient (VAD) mice, and LRAT −/− vitamin A deficient (VAD) mice treated with AC261066 for 8 weeks. AC261066 increased the RARβ2 mRNA levels in vitamin A deficient mice (LRAT −/− on a VAD diet for 4 months.

AC2621066 increased pancreatic mRNA expression of RARβ obese and vitamin A deficient mice. Consistent with our HPLC data demonstrating that pancreata tissue from HF-fed, obese mice had significantly decreased VA (vitamin A) levels, and significantly decreased mRNA levels of the VA responsive gene and VA signaling transcription factor, RARβ. RARβ was decreased in pancreata of HF-fed obese mice compared to control diet fed mice (FIG. 9). mRNA levels of RARβ in pancreata HF-AC261066 treated mice were increased compared to HF-vehicle treated mice (FIG. 9), and near levels observed in non-obese controls, suggesting that AC261066 can prevent or reverse the loss of VA signaling in VA depleted tissue. Similar findings in vitamin A deficient mice, FIG. 10.

Example 8

Liver

Hematoxylin and Eosin Staining. At sacrifice, fresh mouse liver samples were fixed in 4% formaldehyde solution for 24 hr and embedded in paraffin blocks. Liver paraffin sections were cut 5 microns thick and mounted on glass slides and stained with hematoxylin and eosin (H and E) using standard protocols.

Combined oil red O and Immunofluorescence. Staining. Fresh mouse liver samples were embedded in optimal cutting temperature (OCT) medium and immediately frozen to −70 centigrade. Cryosections were then fixed in 4% formaldehyde for 1 hr at room temp. Slides were then rinsed three times in deionized water (dH2O) for 30 s, followed by treatment with 0.5% Triton X-100 in PBS for 5 min. Sections were then washed three times with PBS for 5 min. Samples were with incubated 2% bovine serum albumin (BSA) for 30 min at room temperature to block for unspecific antibody binding. Following blocking, sections were washed three times in PBS and incubated with mouse monoclonal antibody against α-SMA (1:500) (Dako, Inc) for 24 h at 4° C. After 24 h sections were washed three times in PB and incubated with Alexa-Flour-488 anti-mouse secondary anti-body (1:500) (Invitrogen, Inc) for 30 min at room temperature. Sections were then washed three times in PBS and incubated with working strength oil-red O solution for 30 minutes at room temperature. Sections were then rinsed for 30 minutes under running tap water and cover-slipped with Vectashield hard mount plus DAPI (Vector Labs, Inc).

Semi-Quantitate PCR (Liver). Total RNA was extracted from mouse tissues using TRIzol reagent (Life technologies) and (1 μg) was used to synthesize cDNA. cDNA synthesis was performed at 42° C. for 1 h in a final volume of 20 μl using qScript (Quanta, Md.). Semi-quantitative PCR were performed Taq DNA polymerase (Invitrogen, CA). Three step PCR was run as follows: 94° C. for 30 s, 58-64° C. for 45 s for primer annealing and 72° C. for 1 min for primer extension. The number of cycles for each primer pair for amplification in the linear range was determined experimentally. PCR products were resolved on 2% agarose gels and visualized by staining with ehtidium bromide. Primers for gene expression used were as follows: RARβ2, F: 5'-TGG-CATTGTTTGCACGCTGA-3' (SEQ ID No. 25), R: 5'-CCCCCCTTTGGCAAAGAATAGA-3' (SEQ ID No. 26), CYP26A1, F: 5'-CTTTATAAGGCCGCCCAGGTTAC-3' (SEQ ID No. 27), R: 5'-CCCGATCCGCAATTAAA-GATGA-3' (SEQ ID No. 28), LRAT, F: 5'-TCTGG-CATCTCTCCTACGCTG-3' (SEQ ID No. 29), R: 5'-GTTCCAAGTCCTTCAGTCTCTTGC-3' (SEQ ID No. 30), INS2, F: 5'-TGTGGGGAGCGTGGCTTCTTCT-3' (SEQ ID No. 31), R: 5'-CAGCTCCAGTTGTGC-CACTTGT-3' (SEQ ID No. 32), TNFα, F: 5'-CCTGTAGCCCACGTCGTAG-3' (SEQ ID No. 35), R: 5'-GGGAGTAGACAAGGTACAACCC-3' (SEQ ID No. 36), MCP1, F: 5'-TTAAAAACCTGGATCGGAACCAA-3' (SEQ ID No. 37), R: 5'-GCATTAGCTTCAGATT-TACGGGT-3' (SEQ ID No. 38), HPRT, F: 5'-TGCTCGAGTGTGATGAAGG-3' (SEQ ID No. 33), R: 5'-TCCCTGTTGACTGGTCATT-3' (SEQ ID No. 34).

Serum triglyceride level measurement. The analysis of serum triglyceride levels was carried out using a bichromatic assay at the Laboratory of Comparative Pathology of the Memorial Sloan-Kettering Cancer Center. Chow-fed diet (CFD) n=2; high fat diet (HFD) n=3; high fat diet+ AC261066 (HFDAC) n=5.

Analysis of serum and liver retinoids. The frozen liver tissue samples (~100 mg) were homogenized in 500 μl cold phosphate-buffered saline (PBS). In addition, 100 μl serum was diluted in cold PBS to total volume of 500 μl. Retinyl acetate was added to each sample before the retinoid extraction for the calculation of extraction efficiency. The retinoids were extracted into 350 μl of organic solution (acetonitrile/butanol, 50:50, v/v) in the dark. The high performance liquid chromatography (HPLC) was performed using a Waters Millennium system (Waters). Each sample (100 μl of the 350 μl) was loaded onto an analytical 5-μm reverse phase C18 column (Vydac, Hesperia, Calif.) and eluted at a flow rate of 1.5 ml/min. Two mobile phase gradient systems were used. Retinoids were identified by HPLC based on two criteria: an exact match of the retention times of unknown peaks with those of authentic retinoid standards and identical UV light spectra (220-400 nm) of unknowns against spectra from authentic retinoid standards during HPLC by the use of a photodiode array detector. The amounts of retinoids were calculated from the areas under the peaks detected at the wave-length of 325 nm. The levels of retinol and retinyl esters were normalized to the tissue weight.

4-hydroxynonenal (4-HNE) staining. Paraffin-embedded sections (from two to four mice per group) were deparaffinized and rehydrated, and antigen retrieval was performed using an antigen unmasking solution (Vector Laboratories, H-3300). After quenching endogenous peroxidase with 3% H2O2, the tissue sections were blocked with the blocking reagent (from the M.O.M. kit from Vector Laboratories). Then, tissue sections were incubated with a 4-HNE antibody (1:400; mouse monoclonal antibody; Abcam, ab48506) overnight at 4° C. The sections were then incubated with secondary antibodies (1:200, anti-mouse IgG from the M.O.M kit). As a negative control, sections were stained without incubation with primary antibodies. The signals were visualized based on a peroxidase detection mechanism with 3,3-diaminobenzidine (DAB) used as the substrate.

Analysis of serum and liver retinoids. The frozen liver tissue samples (~100 mg) were homogenized in 500 μl cold phosphate-buffered saline (PBS). In addition, 100 μl serum was diluted in cold PBS to total volume of 500 μl. Retinyl acetate was added to each sample before the retinoid extraction for the calculation of extraction efficiency. The retinoids were extracted into 350 μl of organic solution (acetonitrile/butanol, 50:50, v/v) in the dark. The high performance liquid chromatography (HPLC) was performed using a Waters Millenium system (Waters). Each sample (100 μl of the 350 μl) was loaded onto an analytical 5-μm reverse phase C18 column (Vydac, Hesperia, Calif.) and eluted at a flow rate of 1.5 ml/min. Two mobile phase gradient systems were used. Retinoids were identified by HPLC based on two criteria: an exact match of the retention times of unknown peaks with those of authentic retinoid standards and identical UV light spectra (220-400 nm) of unknowns against spectra from authentic retinoid standards during HPLC by the use of a photodiode array detector. The amounts of retinoids were calculated from the areas under the peaks detected at the wave-length of 325 nm. The levels of retinol and retinyl esters were normalized to the tissue weight.

Figure 11:
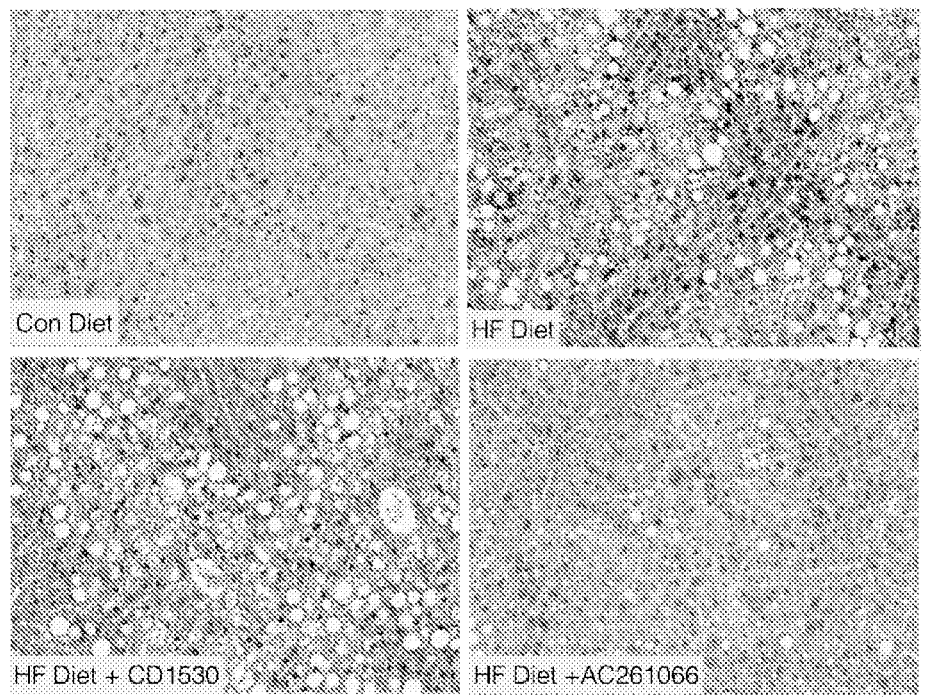
FIG. 11. AC261066 diminished hepatic steatosis. Representative hematoxylin and eosin stained liver sections from wild type (wt) male C57/BL6 mice fed either a chow control diet (Con), high fat (HF) diet, HF diet plus AC261066 or HF diet plus CD1530 (RAR gamma agonist) for 4 months. Con Diet (n=5); HF diet (n=5); HF Diet+AC261066 (n=5), or HF diet+CD1530 (RAR gamma agonist) (n=4).

AC261066 diminished hepatic steatosis. H and E staining of liver sections from treatment mice revealed that 4 months of a HF western style diet lead to increased hepatocyte lipid accumulation in HF-fed mice compared to CFD-fed mice (FIG. 11). HF-fed mice treated with AC261066 showed marked decreased hepatocyte lipid infiltration compared to HF-vehicle treated mice (FIG. 11). HF-fed mice treated with a RARγ ligand (CD1530) showed no decrease in hepatic lipid accumulation (FIG. 11).

Figure 12:
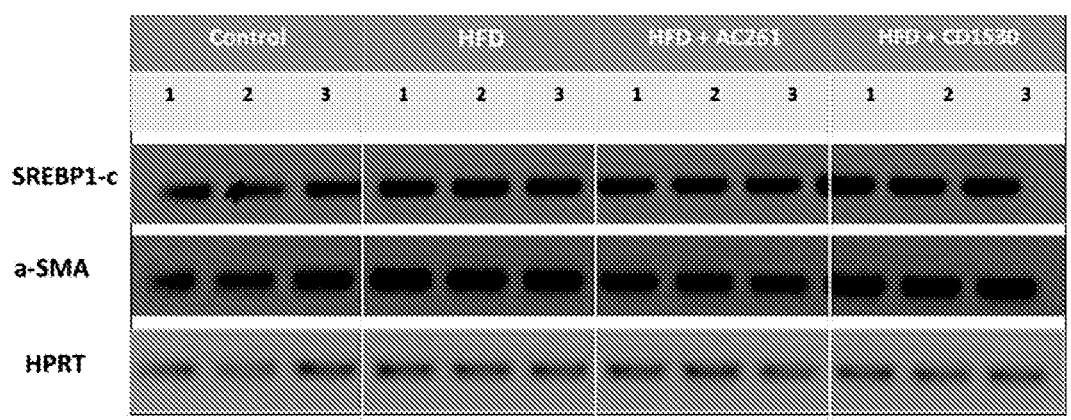
FIG. 12. Gene expression in livers of control and HF-Fed mice. Gene expression of SREBP1c and α-SMA in livers from wild type (wt) male C57/BL6 mice fed either a chow control diet (Con), high fat (HF) diet, a HF diet plus AC261066 or HF diet plus CD1530 (RAR gamma agonist) for 4 months. Con Diet (n=5); HF diet (n=5); HF Diet+AC261066 (n=5), or HF diet+CD1530 (RAR gamma agonist) (n=4).

AC261066 diminishes hepatic gene expression of alpha-SMA (alpha-smooth muscle actin) and SREBP1c. Consistent with our immunofluorescence microscopy showing that α-SMA protein is decreased in HF-AC261011 fed mice compared to HF-vehicle controls, hepatic mRNA levels of alpha-SMA were also decreased in livers of HF-AC261011 fed mice, but not in the livers of HF-CD1530 treated mice (FIG. 12). We also measured mRNA expression of SREBP1-c, which codes for a transcription factor responsible for de novo synthesis of triglyceride and is often over-expressed in livers of animals with experimentally induced NAFLD. Our analysis revealed that mRNA levels of SREBP1-c are markedly higher in livers of HF-fed and HF-fed CD1530 treated mice, but not in livers of HF-AC261011 treated mice (FIG. 12).

Figure 13:
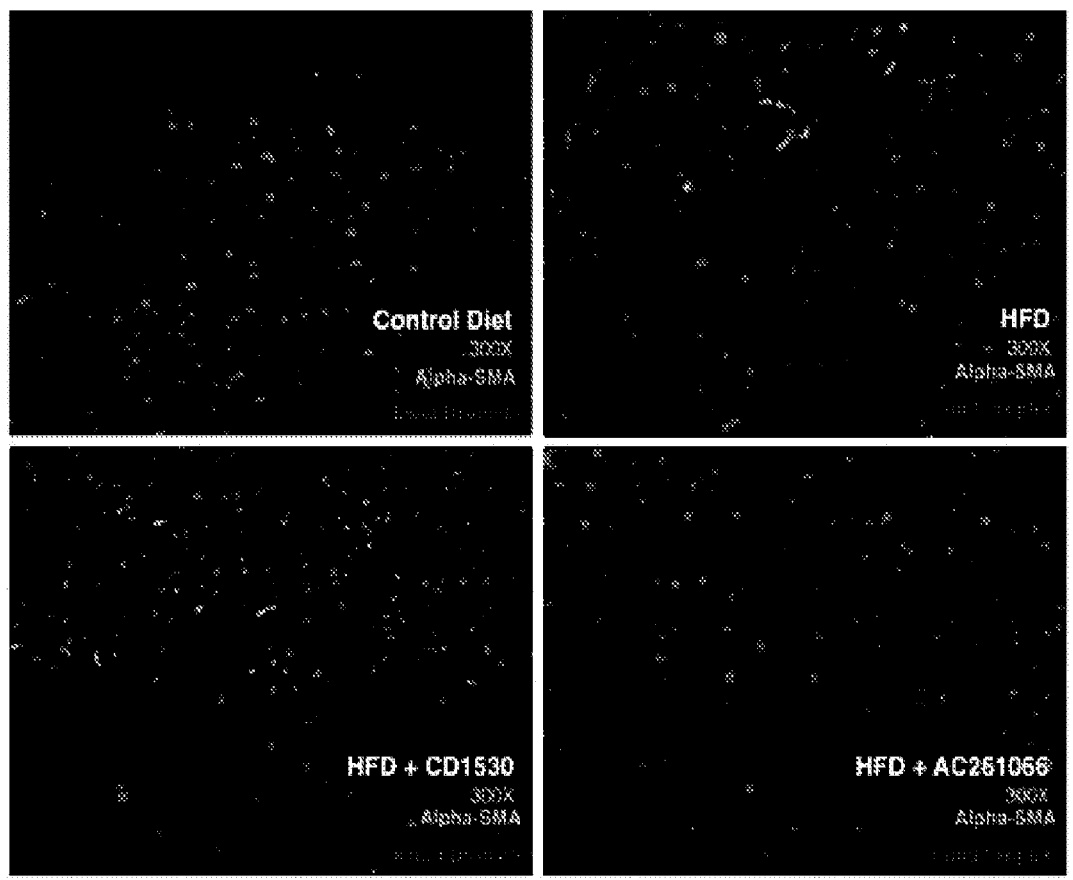
FIG. 13. AC261066 diminished activation of hepatic stellate cells. Representative immunofluorescence and oil red o stained liver sections from wild type (wt) male C57/BL6 mice fed either a chow control diet (Con), high fat (HF) diet, HF diet plus AC261066 or HF diet plus CD1530 (RAR gamma agonist) for 4 months. Control Diet (n=5); HF diet (n=5); HF Diet+AC261066 (n=5), or HF diet+CD1530 (RAR gamma agonist).

AC261066 diminishes hepatic stellate cell (HSC) activation. Liver sections co-stained with the neutral lipid stain oil-red-o were in agreement with the H and E staining, demonstrating that HF-fed obese mice had ectopic accumulation of hepatic lipids (red) compared to CF controls (FIG. 13). Livers of HF-AC261066-fed mice had marked diminished hepatic lipid accumulation compared to HF vehicle-fed mice (FIG. 13). This effect was not observed in the livers of HF-fed mice treated with the CD1530 (RARγ agonist).

Activated HSCs contribute to normal liver tissue repair processes, but unresolved HSC activation can lead to fibrotic lesion formation and the progression of steatosis to advanced NAFLD, such as non-alcoholic steatohepatitis (NASH). To examine whether HF-fed obese mice exhibited evidence of increased activation of HSCs we stained liver sections with an α-SMA antibody. This analysis revealed the livers of HF-fed mice had increased α-SMA positive (green) staining compared to lean, CF controls. α-SMA positive areas tended to cluster in areas with hepatocyte lipid infiltration (FIG. 13). Compared to HF-fed mice, livers of HF-fed-AC261066 treated mice had decreased intensity and regions of α-SMA positive staining (FIG. 13). Moreover, clustering α-SMA in lipid positive (red) regions was not observed in liver of HF-AC261066 treated mice. Livers of HF-fed CD1530 treated mice had no evidence decreased lipid accumulation or α-SMA expression intensity or patterns compared to HF fed-vehicle treated mice.

Figure 14:
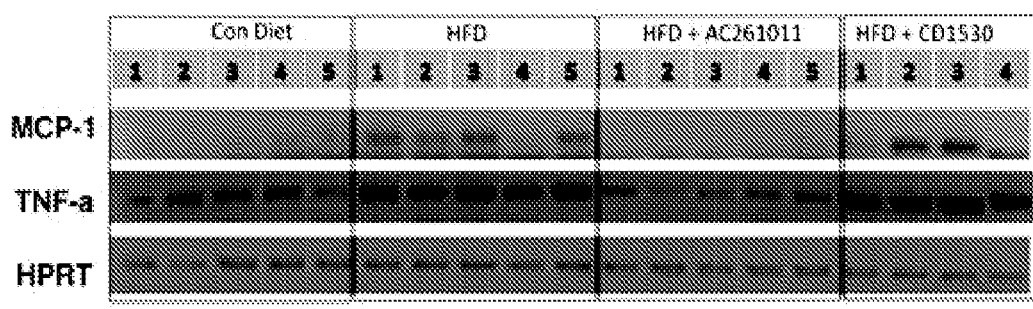
FIG. 14. Gene Expression of Inflammatory Mediators in Livers of LF and HF-Fed Mice. Gene expression of MCP-1, TNF-alpha in livers from wild type (wt) male C57/BL6 mice fed either a chow control diet (Con), high fat (HF) diet, HF diet plus AC261066 or HF diet plus CD1530 (RAR gamma agonist) for 4 months. LF Diet (n=5); HF diet (n=5); HF Diet+AC261066 (n=5), or HF diet+CD1530 (RAR gamma agonist) (n=4). AC261066 decreases levels of inflammatory proteins MCP-1 and TNF alpha in livers of HF diet fed mice.

AC261066 diminishes hepatic gene expression of pro-inflammatory mediators. NAFLD is typically associated with increased hepatic expression of pro-inflammatory cytokines and mediators such as the monocyte chemokine MCP-1 and the cytokine TNF-α. We examined expression of these genes in livers of CF and HF-fed mice. Our analysis revealed that mRNA levels of both MCP-1 and TNF-α were markedly elevated in livers of HF-fed mice HF-fed CD1530 treated mice, but not in livers of HF-fed AC261066 treated mice (FIG. 14).

Figure 15:
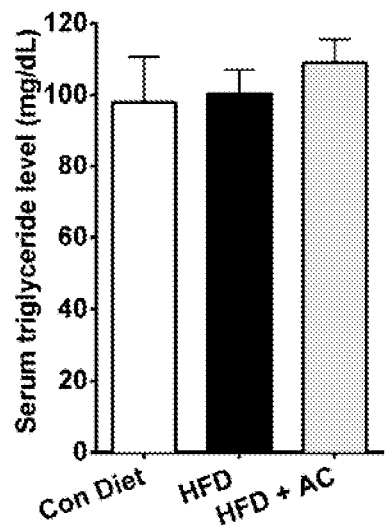
FIG. 15. Mouse serum triglyceride levels following the treatments indicated. Con diet (n=2); HFD (n=3); HFDAC (n=5). Con, control diet; HFD, high fat diet; HFD+AC, high fat diet+AC261066. AC261066 does not increase triglyceride levels at doses used.

AC261066 does not elevate serum triglyceride levels. We examined the triglyceride levels in mouse serum samples because elevated triglycerides are a risk factor for cardiovascular disease. As shown in FIG. 15, HF or HF+AC261066 feeding does not affect serum triglyceride levels compared CF controls. This suggests that AC261066 does not increase risk for cardiovascular disease and suggests that the liver lipid lowering effect of AC261066 does not correlate with increased hepatic lipid export.

Figure 16:
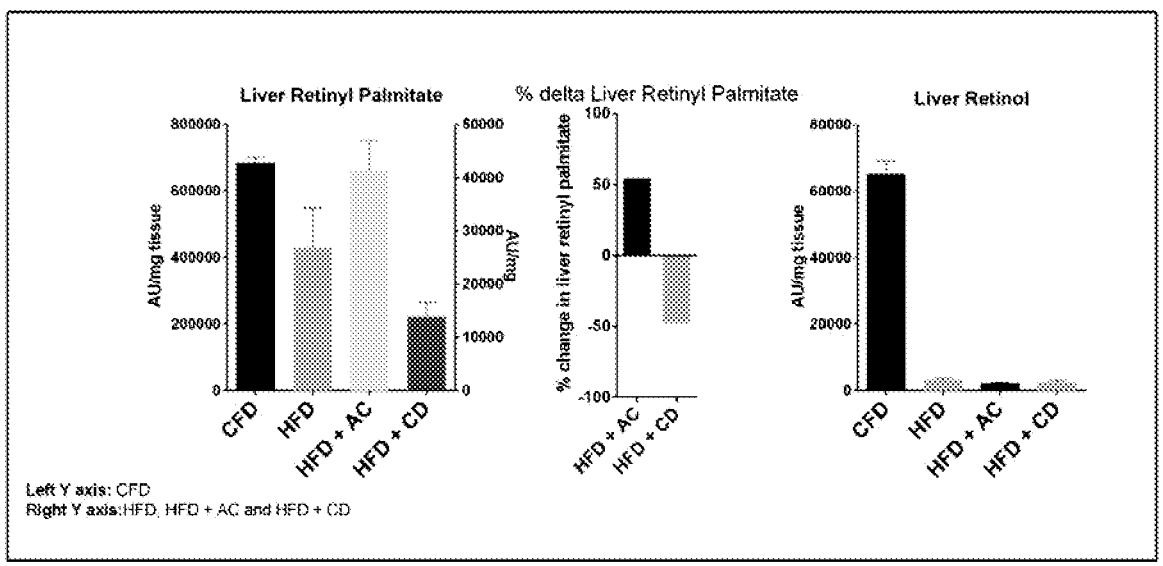
FIG. 16. Retinoid levels in mouse liver following the treatments indicated. Con fed diet (CFD) (n=5); HFD (n=5); HFD+AC261066 (n=5), HFD+CD1530 (n=4). High fat diet caused a state of vitamin A deficiency in liver and this is partially reversed by AC261066. Note that the y-axes in the left panel are different for CFD and HFD. The HFD reduced retinyl esters, (retinyl palmitate), a form of storage of vitamin A in the liver, by greater than 90% (left panel). The HFD also reduced retinol (vitamin A) levels by over 90% to result in vitamin A deficiency in the liver.

AC261066 partially reverses depletion of VA in livers of HF-fed Obese Mice. The liver stores approximately 80-90% of total body VA, therefore we conducted HPLC to determine the tissue levels of the major storage form of VA, retinyl-palmitate and of all-trans retinol in lean CF, HF and HF+AC261066 fed mice. Our analysis revealed that levels of retinyl-palmitate and retinol were decreased by 97% and 92% in livers in HF-fed, obese mice compared to lean, CF controls (FIG. 16). Serum levels of the major circulating form of VA, all-trans retinol were not different between CF, HF and HF+AC261066 fed mice, suggesting that HF-driven obesity leads to tissue VA depletion which is not reflected by serum VA levels.

Livers of mice fed HF+AC261066 and CD1530 also had significantly lowered retinyl palmitate and retinol compared to controls, however compared to HF-vehicle treated mice, we observed 55% higher levels of retinyl palmitate in the livers from HF-AC261066 fed mice, while retinyl palmitate levels in the liver of HF+CD1530 treated mice were almost 48% lower than livers from HF-vehicle treated mice (FIG. 16). This suggests that longer administration of AC261066 to HF-fed obese mice may have significantly reversed HF-obesity driven liver VA depletion.

Figure 17:
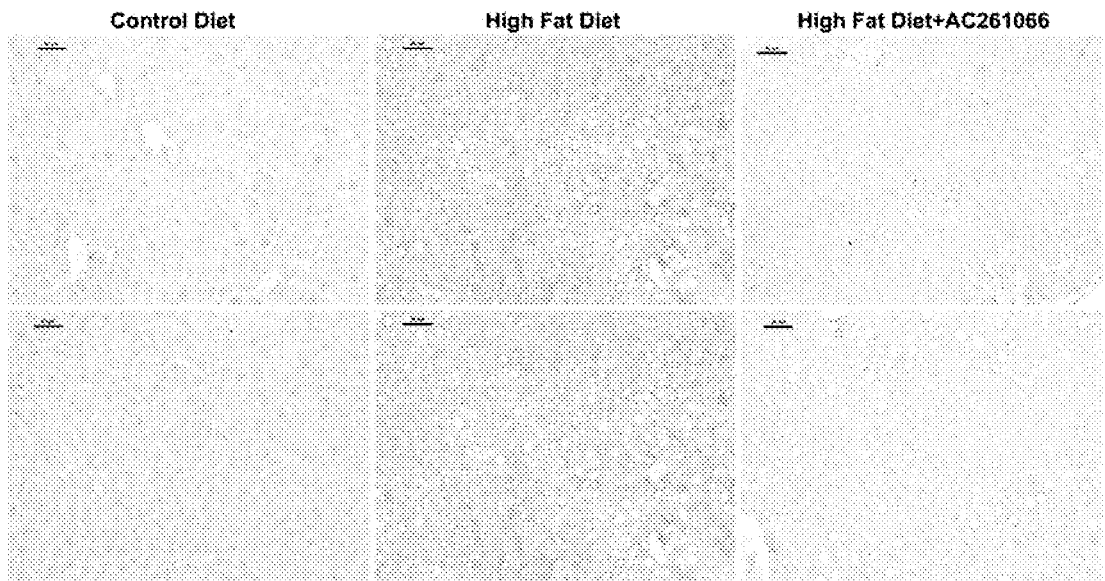
FIG. 17. 4-hydroxynonenal (4-HNE), an indicator of oxidative stress, in the liver. The liver samples were fixed, embedded in paraffin, and sectioned. Then the tissue sections were stained with an antibody against 4-HNE (magnification, 200×). Sections from two mice/group were photographed and analyzed. These data show that AC261066 reduces oxidative stress and ROS (reactive oxygen species) in the livers of HF diet fed mice. Oxidative stress damages tissues.

Oxidative stress level, as assessed by 4-hydroxynoneal (4-HNE), is lower in the liver from the high fat diet plus AC261066 group than that in the high fat diet group. High fat diet results in excessive reactive oxygen species (ROS) production that triggers inflammatory responses and subsequent injuries in many tissues. Therefore, we examined the levels of 4-hydroxynonenal (4-HNE), an α,β-unsaturated hydroxyalkenal that is produced by lipid peroxidation in cells during oxidative stress, and is a marker of oxidative stress caused by reactive oxygen species (ROS) in the liver. The liver from the high fat diet group showed a large increase in the 4-HNE levels compared to the control fat diet group, and the liver samples from the high fat diet plus AC261066 group exhibited lower 4-HNE levels than those from the high fat diet group (FIG. 17).

Example 9

Kidney

Hematoxylin and Eosin Staining. At sacrifice, fresh mouse liver samples were fixed in 4% formaldehyde solution for 24 hr and embedded in paraffin blocks. Kidney paraffin sections were cut 5 microns thick and mounted on glass slides and stained with hematoxylin and eosin (H and E) using standard protocols.

Combined oil red O and Immunofluorescence staining. Fresh mouse kidney samples were embedded in optimal cutting temperature (OCT) medium and immediately frozen to −70 centigrade. Cryosections were then fixed in 4% formaldehyde for 1 hr at room temp. Slides were then rinsed three times in deionized water (dH2O) for 30 s, followed by treatment with 0.5% Triton X-100 in PBS for 5 min. Sections were then washed three times with PBS for 5 min. Samples were with incubated 2% bovine serum albumin (BSA) for 30 min at room temperature to block for unspecific antibody binding. Following blocking, sections were washed three times in PBS and incubated with mouse monoclonal antibody against α-SMA (1:500) (Dako, Inc) for 24 h at 4° C. After 24 h sections were washed three times in PB and incubated with Alexa-Flour-488 anti-mouse secondary anti-body (1:500) (Invitrogen, Inc) for 30 min at room temperature. Sections were then washed three times in PBS and incubated with working strength oil-red O solution for 30 minutes at room temperature. Sections were then rinsed for 30 minutes under running tap water and cover-slipped with Vectashield hard mount plus DAPI (Vector Labs, Inc).

Semi-Quantitative PCR. Total RNA was extracted from mouse tissues using TRIzol reagent (Life technologies) and (1 μg) was used to synthesize cDNA. cDNA synthesis was performed at 42° C. for 1 h in a final volume of 20 μl using qScript (Quanta, Md.). Semi-quantitative PCR were performed Taq DNA polymerase (Invitrogen, CA). Three step PCR was run as follows: 94° C. for 30 s, 58-64° C. for 45 s for primer annealing and 72° C. for 1 min for primer extension. The number of cycles for each primer pair for amplification in the linear range was determined experimentally. PCR products were resolved on 2% agarose gels and visualized by staining with ehtidium bromide. Primers for gene expression used were as follows: RARβ2, F: 5'-TGG-CATTGTTTGCACGCTGA-3' (SEQ ID No. 25), R: 5'-CCCCCCTTTGGCAAAGAATAGA-3' (SEQ ID No. 26), CYP26A1, F: 5'-CTTTATAAGGCCGCCCAGGTTAC-3' (SEQ ID No. 27), R: 5'-CCCGATCCGCAATTAAA-GATGA-3' (SEQ ID No. 28), TNFα, F: 5'-CCTGTAGCC-CACGTCGTAG-3' (SEQ ID No. 35), R: 5'-GGGAGTAGACAAGGTACAACCC-3' (SEQ ID No. 36), HPRT, F: 5'-TGCTCGAGTGTGATGAAGG-3' (SEQ ID No. 33), R: 5'-TCCCTGTTGACTGGTCATT-3' (SEQ ID No. 34).

Analysis of kidney retinoids. The frozen kidney tissue samples (~100 mg) were homogenized in 500 µl cold phosphate-buffered saline (PBS). In addition, 100 µl serum was diluted in cold PBS to total volume of 500 µl. Retinyl acetate was added to each sample before the retinoid extraction for the calculation of extraction efficiency. The retinoids were extracted into 350 µl of organic solution (acetonitrile/butanol, 50:50, v/v) in the dark. The high performance liquid chromatography (HPLC) was performed using a Waters Millennium system (Waters). Each sample (100 µl of the 350 µl) was loaded onto an analytical 5-µm reverse phase C18 column (Vydac, Hesperia, Calif.) and eluted at a flow rate of 1.5 ml/min Two mobile phase gradient systems were used. Retinoids were identified by HPLC based on two criteria: an exact match of the retention times of unknown peaks with those of authentic retinoid standards and identical UV light spectra (220-400 nm) of unknowns against spectra from authentic retinoid standards during HPLC by the use of a photodiode array detector. The amounts of retinoids were calculated from the areas under the peaks detected at the wave-length of 325 nm. The levels of retinol and retinyl esters were normalized to the tissue weight.

4-hydroxynonenal (4-HNE) staining. Paraffin-embedded sections (from two to four mice per group) were deparaffinized and rehydrated, and antigen retrieval was performed using an antigen unmasking solution (Vector Laboratories, H-3300). After quenching endogenous peroxidase with 3% $H_2O_2$, the tissue sections were blocked with the blocking reagent (from the M.O.M. kit from Vector Laboratories). Then, tissue sections were incubated with a 4-HNE antibody (1:400; mouse monoclonal antibody; Abcam, ab48506) overnight at 4° C. The sections were then incubated with secondary antibodies (1:200, anti-mouse IgG from the M.O.M kit). As a negative control, sections were stained without incubation with primary antibodies. The signals were visualized based on a peroxidase detection mechanism with 3,3-diaminobenzidine (DAB) used as the substrate.

Figure 18:
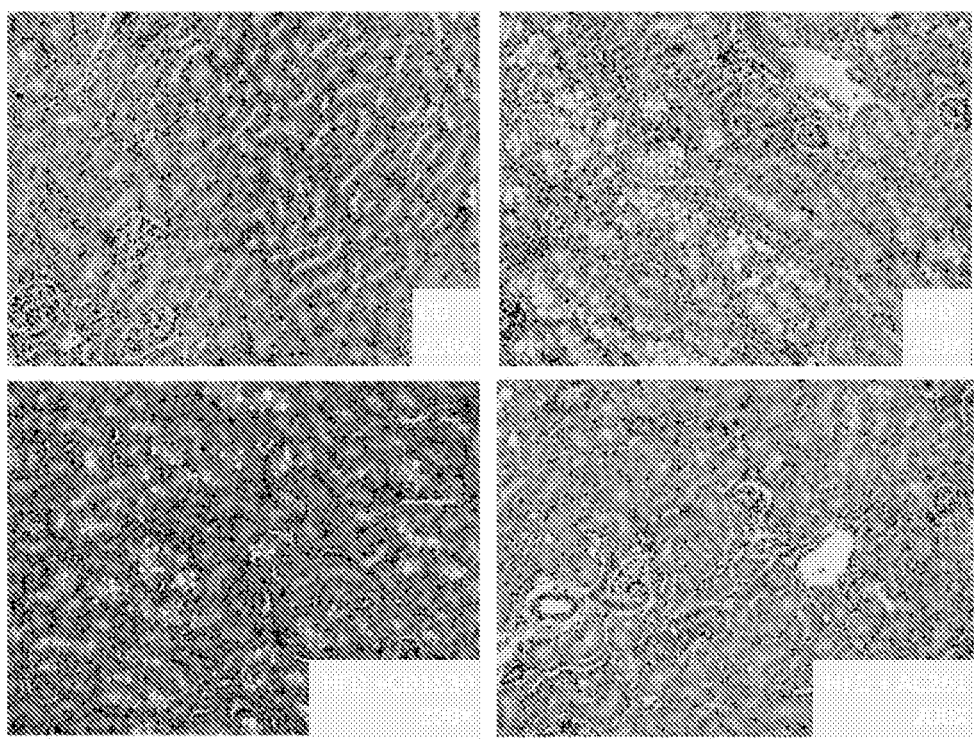
FIG. 18. AC261066 diminished renal lipid accumulation. Representative hematoxylin and eosin stained kidney sections from wild type (wt) male C57/BL6 mice fed either a chow control diet (Con), high fat (HF) diet, HF diet plus AC261066 or HF diet plus CD1530 (RAR gamma agonist) for 4 months. Con Diet (n=5); HF diet (n=5); HF Diet+AC261066 (n=5), or HF diet+CD1530 (RAR gamma agonist) (n=4).

AC261066 diminished renal lipid accumulation. H and E staining of kidney sections from treatment mice revealed that 4 months of a HF western style diet lead to increased renal lipid accumulation in HF-fed mice compared to CFD-fed mice (FIG. 18). HF-fed mice treated with AC261066 showed markedly decreased renal lipid infiltration compared to HF-vehicle treated mice (FIG. 18). HF-fed mice treated with a RARγ ligand (CD1530) showed no decrease in renal lipid accumulation (FIG. 18).

Figure 19:
FIG. 19. AC261066 diminished expression of the fibrogenic protein alpha-SMA. Representative immunofluorescence and oil red o stained kidney sections from wild type (wt) male C57/BL6 mice fed either a chow control diet (Con), high fat (HF) diet, or HF diet plus AC261066 for 4 months. Chow Diet (n=5); HF diet (n=5); HF Diet+AC261066 (n=5), or HF diet+CD1530 (RAR gamma agonist).

AC261066 diminishes renal expression of alpha-SMA. Kidney sections co-stained with the neutral lipid stain oil-red-o were in agreement with the H and E staining, demonstrating that HF-fed obese mice had ectopic accumulation of renal lipids (red) compared to CF controls (FIG. 18). Kidneys of HF-AC261066-fed mice had marked diminished hepatic lipid accumulation compared to HF vehicle-fed mice (FIG. 19). Alpha-SMA is required for normal kidney tissue repair processes, but unchecked alpha-SMA secretion can lead to fibrotic lesion formation and the progression of advanced renal disease. As expected kidney sections stained with the neutral lipid stain oil-red-o (red) showed marked increase in renal lipid droplets in kidneys of HF-fed mice compared to control fed mice. In agreement with our H and E histological analysis, kidney sections from HF+AC261066 treated mice had comparably less oil red o positive areas. α-SMA (green) staining also revealed that kidneys of HF-fed mice had increased α-SMA positive areas compared to control fed mice (FIG. 19). This increase in α-SMA positive areas was not observed in kidneys of HF+AC261066 treated mice.

Figure 20:
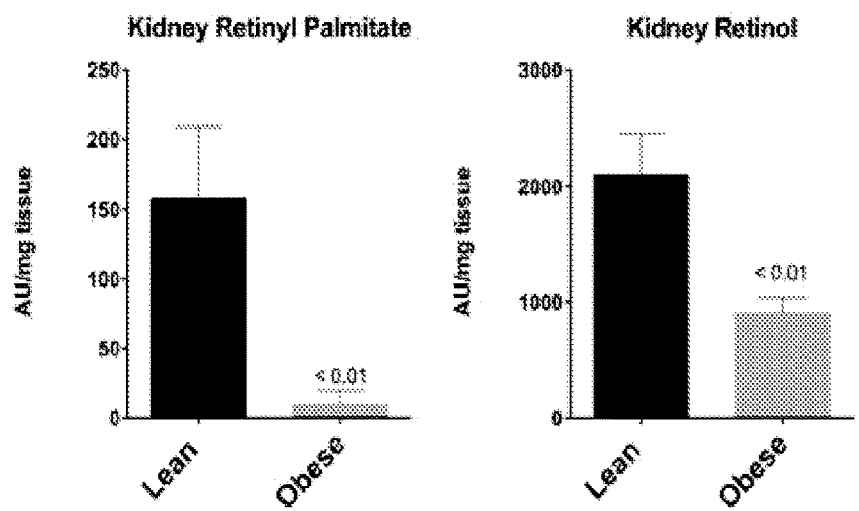
FIG. 20. Retinoid levels in mouse kidney following the treatments indicated. Con fed diet (CFD) (Lean) (n=5) or HFD (Obese) (n=5). The high fat diet led to dramatic declines in retinyl esters (retinyl palmitate) and retinol in the kidney, showing a vitamin A deficiency in kidney.

Retinoid levels in kidneys. Our HPLC analysis of kidney tissue demonstrated that HF-fed obese mice had significantly decreased levels of kidney retinyl palmitate and retinol compared to chow fed controls (FIG. 20).

Figure 21:
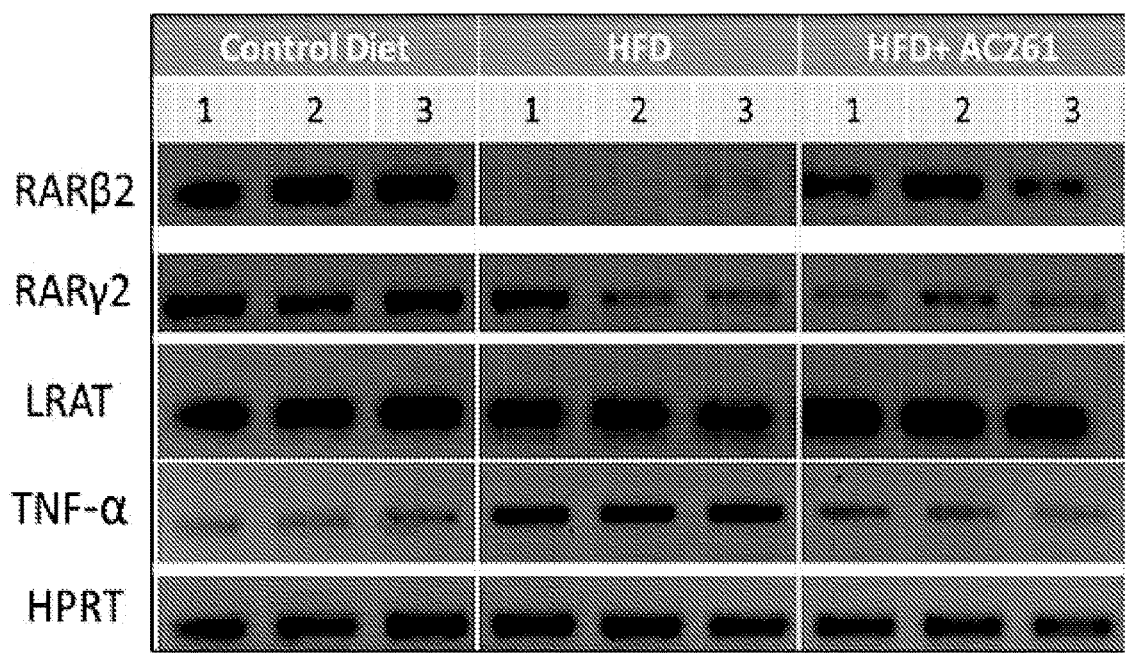
FIG. 21. Gene Expression of Inflammatory Mediators in Kidneys of Control Normal Chow (13% fat) and HF-Fed Mice and RARs. Gene expression of kidney from wild type (wt) male C57/BL6 mice fed either a chow control diet (Con), high fat (HF) diet, HF diet plus AC261066. AC261066 reduces the levels of TNF-alpha, a potent inflammatory protein, mRNA in high fat diet fed mice. AC261066 also restores RAR beta and LRAT mRNA levels, markers of functional vitamin A signaling, in the high fat diet fed mice, 4 months on the HFD. HPRT, loading control.

AC261066 diminishes kidney gene expression of pro-inflammatory mediators. Fibrosis is associated increased renal expression of pro-inflammatory cytokines and mediators. We examined whether kidneys of HF-fed mice had evidence of inflammation marked by increased expression of inflammatory cytokines such as TNF-α. Our analysis revealed that mRNA levels of TNF-α were markedly elevated in livers of HF-fed mice, but not in livers of HF-fed AC261066 treated mice (FIG. 21).

AC261066 increased kidney gene expression of RARβ2. Consistent with the HPLC data demonstrating that VA levels are diminished in kidney of HF-fed mice, our kidney gene expression analysis revealed that RARβ2 mRNA is markedly decreased in the kidney of HF-fed mice (FIG. 21). Kidney's from HF-AC261066 did not have decreased RARβ2 mRNA levels (FIG. 21).

Figure 22:
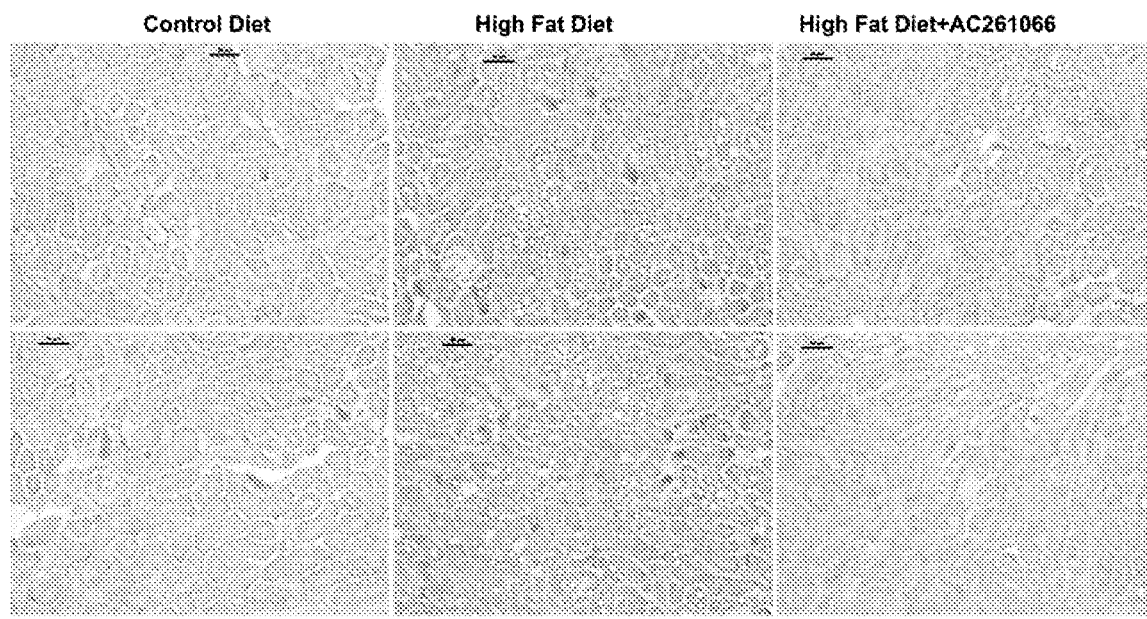
FIG. 22. 4-hydroxynonenal (4-HNE), an indicator of oxidative stress, in the kidneys. The kidney samples were fixed, embedded in paraffin, and sectioned. Then the tissue sections were stained with an antibody against 4-HNE (magnification, 200×). Sections from two mice/group were photographed and analyzed. AC261066 reduces oxidative stress (ROS) in the kidneys of mice fed the HF diet.

Oxidative stress level, as assessed by 4-hydroxynoneal (4-HNE), is lower in the kidneys from the high fat diet plus AC261066 group than that in the high fat diet group. High fat diet results in excessive reactive oxygen species (ROS) production that triggers inflammatory responses and subsequent injuries in many tissues. Therefore, we examined the levels of 4-hydroxynonenal (4-HNE), an α,β-unsaturated hydroxyalkenal that is produced by lipid peroxidation in cells during oxidative stress, and is a marker of oxidative stress caused by reactive oxygen species (ROS) in the kidneys. The kidneys from the high fat diet group showed a large increase in the 4-HNE levels compared to the control fat diet group, and the kidneys from the high fat diet plus AC261066 group exhibited lower 4-HNE levels than those from the high fat diet group (FIG. 22).

Example 10

Testes

Semi-Quantitative PCR. Total RNA was extracted from mouse tissues using TRIzol reagent (Life technologies) and (1 µg) was used to synthesize cDNA. cDNA synthesis was performed at 42° C. for 1 h in a final volume of 20 µl using qScript (Quanta, Md.). Semi-quantitative PCR were performed Taq DNA polymerase (Invitrogen, CA). Three step PCR was run as follows: 94° C. for 30 s, 58-64° C. for 45 s for primer annealing and 72° C. for 1 min for primer extension. The number of cycles for each primer pair for amplification in the linear range was determined experimentally. PCR products were resolved on 2% agarose gels and visualized by staining with ehtidium bromide. Primers for gene expression used were as follows: RARβ2, F: 5'-TGG-CATTGTTTGCACGCTGA-3' (SEQ ID No. 25), R: 5'-CCCCCCTTTGGCAAAGAATAGA-3' (SEQ ID No. 26), CYP26A1, F: 5'-CTTTATAAGGCCGCCCAGGTTAC-3' (SEQ ID No. 27), R: 5'-CCCGATCCGCAATTAAA-GATGA-3' (SEQ ID No. 28), HPRT, F: 5'-TGCTCGAGTGTGATGAAGG-3' (SEQ ID No. 33), R: 5'-TCCCTGTTGACTGGTCATT-3' (SEQ ID No. 34).

Analysis of testes retinoids. The frozen kidney tissue samples (~100 mg) were homogenized in 500 μl cold phosphate-buffered saline (PBS). In addition, 100 μl serum was diluted in cold PBS to total volume of 500 μl. Retinyl acetate was added to each sample before the retinoid extraction for the calculation of extraction efficiency. The retinoids were extracted into 350 μl of organic solution (acetonitrile/butanol, 50:50, v/v) in the dark. The high performance liquid chromatography (HPLC) was performed using a Waters Millennium system (Waters). Each sample (100 μl of the 350 μl) was loaded onto an analytical 5-μm reverse phase C18 column (Vydac, Hesperia, Calif.) and eluted at a flow rate of 1.5 ml/min. Two mobile phase gradient systems were used. Retinoids were identified by HPLC based on two criteria: an exact match of the retention times of unknown peaks with those of authentic retinoid standards and identical UV light spectra (220-400 nm) of unknowns against spectra from authentic retinoid standards during HPLC by the use of a photodiode array detector. The amounts of retinoids were calculated from the areas under the peaks detected at the wave-length of 325 nm. The levels of retinol and retinyl esters were normalized to the tissue weight.

Figure 23:
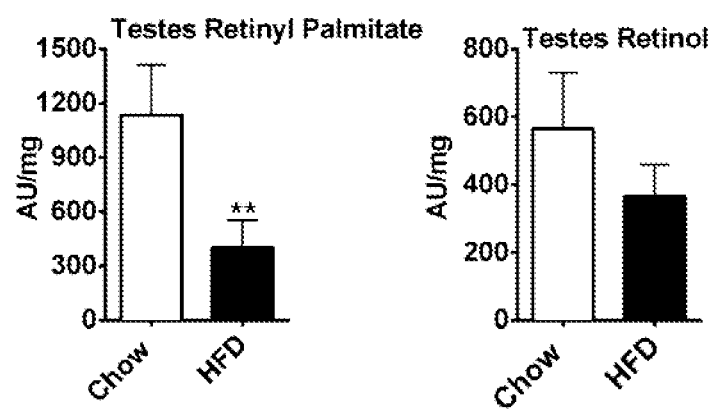
FIG. 23. Retinoid levels in mouse testes following the treatments indicated. Con fed diet (CFD) (n=5) or HFD (n=5). High fat diet results in partial vitamin A deficiency in the testes.

Retinoid levels in testes. Our HPLC analysis of testes demonstrated that HF-fed obese mice had significantly decreased levels of retinyl palmitate (storage form of VA) and decreased retinol compared to chow fed controls (FIG. 23).

Figure 24:
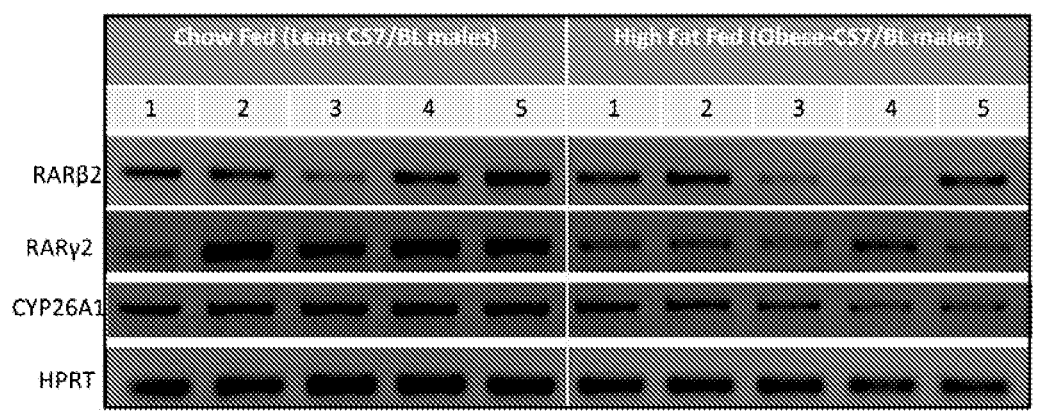
FIG. 24. Gene expression of vitamin A relevant genes in testes of chow and HF-Fed mice. Gene expression of testes from wild type (wt) male C57/BL6 mice fed either a chow control diet (Con), high fat (HF) diet, HF diet plus AC261066. (Each number is data from one mouse, five mice total in each group.)

Testes of HF-fed Mice have decreased expression of VA relevant genes expression. Consistent with the HPLC data demonstrating that VA levels are diminished in kidney of HF-fed mice, our testes gene expression analysis revealed that RARβ2 and CYP26A1, and RAR gamma2 mRNAs are markedly decreased in the testes of HF-fed mice (FIG. 24).

RARβ agonist AC55649 is prepared at a concentration of 3.0 mg/100 ml in 1% DMSO and is used to treat mice as described in Examples 6-10.

Example 11

METHODS. Preparation of AC261066 (a RARβ Agonist from Tocris) Solution. AC261066 (Lund et al., Discovery of a potent, orally available, and isoform-selective retinoic acid beta2 receptor agonist. J Med Chem. 2005; 48(24):7517-9) and CD1530 (Thacher et al. Therapeutic applications for ligands of retinoid receptors. Curr Pharm Des. 2000; 6(1): 25-58) was dissolved in dimethyl sulfoxide (DMSO) at the concentration of 1.5 mg/ml for AC261066 and 2.5 mg/ml for CD1530, and diluted in the drinking water for mice to the final concentration of 1.5 mg/100 ml and 2.5 mg/100 ml, respectively.

Example 12

Mice, diet, and drug treatment. WT male C57/BL6 male mice were maintained on either a standard laboratory chow-fed diet (Con) with 13% kcal fat, (diet #5053, Lab Diet, Inc, St. Louis, Mo.) or a high fat, western style diet (HFD) with 45% kcals from fat, (diet #58126, Lab Diet, Inc., St. Louis, Mo.) for 4 months. One month after the start of the HFD treatment, the HFD group was further split into 3 groups for 3 months: i) HFD and the drinking water containing 1% DMSO; ii) high fat diet (HFD) and drinking water containing 1.5 mg/100 ml AC261066, a specific RARβ agonist in 1% DMSO or iii) HFD and drinking water containing 1.5 mg/100 ml CD1530, a specific RARγ agonist in 1% DMSO. Then mice were sacrificed by cervical dislocation. Blood and various tissue samples were harvested.

Example 13

Serum triglyceride and cholesterol level measurements. The analysis of serum triglyceride levels was carried out using a bichromatic assay at the Laboratory of Comparative Pathology of the Memorial Sloan-Kettering Cancer Center. Chow-fed diet (Con) n=4; high fat diet (HFD) n=4; high fat diet (HFD)+AC261066 n=4; and high fat diet (HFD)+CD1530, n=4.

Example 14

Quantitative real time PCR (Q-RT-PCR). Total RNA was extracted from mouse tissues using TRIzol reagent (Life technologies) and (1 μg) was used to synthesize cDNA. cDNA synthesis was performed at 42° C. for 1 h in a final volume of 20 μl using qScript (Quanta, Md.). Q-RTPCR was performed as previously described (15). Primers for gene expression used were as follows:

```
SREBP1C,
F:
                                       (SEQ ID No. 39)
5'-CAAGGCCATCGACTACATCCG-3',

R:
                                       (SEQ ID No. 40)
5'-CACCACTTCGGGTTTCATG-3',

FAS,
F:
                                       (SEQ ID No. 41)
5'-GGAGGTGGTGATAGCCGGTAT-3',

R:
                                       (SEQ ID No. 42)
5'-TGGGTAATCCATAGAGCCCAG-3',

DGAT1,
F:
                                       (SEQ ID No. 43)
5'-ATGATGGCTCAGGTCCCACT-3',

R:
                                       (SEQ ID No. 44)
5'-CACTGGGGCATCGTAGTTGA-3',

SIRT1,
F:
                                       (SEQ ID No. 45)
5'-TCTCCTGTGGGATTCCTGAC-3',

R:
                                       (SEQ ID No. 46)
5'-CTCCACGAACAGCTTCACAA-3',

PPARα,
F:
                                       (SEQ ID No. 47)
5'-AGAGCCCCATCTGTCCTCTC-3',
```

```
R:
                                         (SEQ ID No. 48)
5'-ACTGGTAGTCTGCAAAACCAAA-3',

PPARγ,
F:
                                         (SEQ ID No. 49)
5'-CTCCAAGAATACCAAAGTGCGA-3',

R:
                                         (SEQ ID No. 50)
5'-GCCTGATGCTTTATCCCCACA-3',

SREBP2,
F:
                                         (SEQ ID No. 51)
5'-GCAGCAACGGGACCATTCT-3',

R-
                                         (SEQ ID No. 52)
5'-CCCCATGACTAAGTCCTTCAACT-3',

HMGCR,
F:
                                         (SEQ ID No. 53)
5'-AGCTTGCCCGAATTGTATGTG-3',

R-
                                         (SEQ ID No. 54)
5'-TCTGTTGTGAACCATGTGACTTC-3',

PEPCK.
F:
                                         (SEQ ID No. 55)
5'-TGCCCAAGGCAACTTAAGGG-3',

R-
                                         (SEQ ID No. 56)
5'-CAGTAAACACCCCCATCGCT-3',

FGF21,
F:
                                         (SEQ ID No. 57)
5'-GTGTCAAAGCCTCTAGGTTTCTT-3',

R-
                                         (SEQ ID No. 58)
5'-GGTACACATTGTAACCGTCCTC-3',

HPRT,
F:
                                         (SEQ ID No. 59)
5'-TGCTCGAGTGTGATGAAGG-3',

R:
                                         (SEQ ID No. 60)
5'-TCCCTGTTGACTGGTCATT-3'.
```

Example 15

Figure 25A:
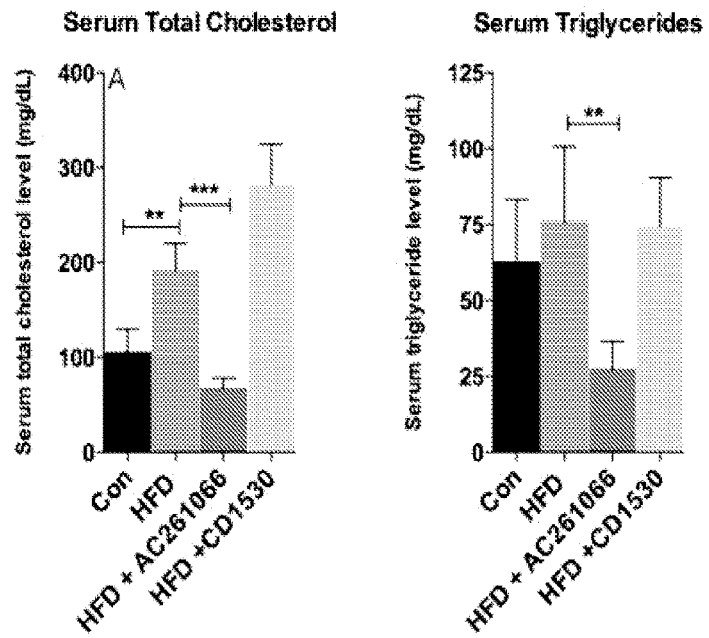
FIG. 25. AC261066 greatly reduces serum lipids and hepatic lipogenic gene expression. A) Serum triglycerides and cholesterol from control diet (Con) (n=4); high fat diet (HFD) (n=4); high fat diet (HFD) plus AC261066 (HFD+AC261066 [RARβ agonist]) (n=4), and high fat diet (HFD) plus CD1530 [RARγ agonist]) (n=4). B) Hepatic gene expression (mRNA) of mediators of lipogenesis and gluconeogesis in Con, HFD, HFD+AC261066 and HFD+CD1530-fed mice.
Figure 25B:
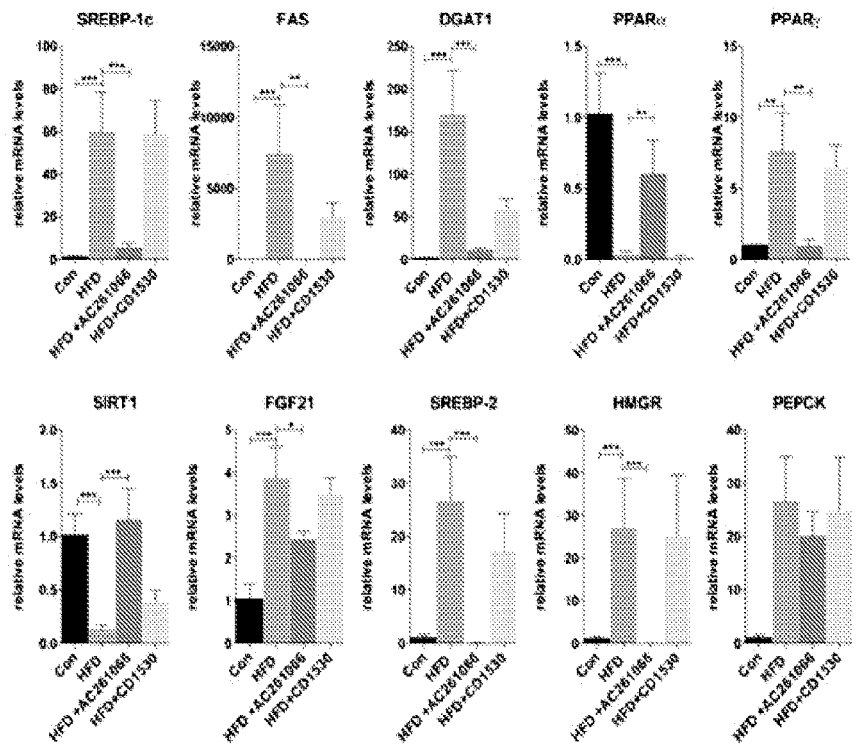

Selective RARβ (e.g., RARβ2) agonists effectively control and reduce serum triglyceride and cholesterol levels. The highly selective RARβ2 agonist, AC261066, provided at a dose of 1.5 mg/100 ml in the drinking water, can significantly lower serum cholesterol and triglycerides in mice fed a high fat diet (HFD) for 4 months (FIG. 25A). In contrast, HFD-fed mice treated with a RARγ agonist, CD1530, showed no decrease in serum cholesterol and triglycerides levels (FIG. 25A). Using quantitative real time PCR (Q-RT-PCR) we also measured hepatic mRNA levels of genes involved in de novo fatty acid, cholesterol and glucose synthesis. We demonstrated that AC261066 significantly reduced hepatic mRNA levels of the lipogenic proteins srebp1-c, fas, dgat1, fgf21, and ppar-γ in HFD-fed mice (FIG. 25B). We also demonstrated that AC261066 treatment prevented a large decrease in the hepatic mRNA levels of sirt1 and ppar-α, two proteins involved in beta-oxidation of fatty acids (FIG. 1B). Our gene expression analysis also revealed that AC261066 treatments significantly reduced hepatic mRNA levels of srebp-2 and hmgcr (FIG. 25B). Srebp-2 is a transcription factor that increases mRNA levels of hmgcr (3-hydroxy-3-methylglutaryl-coenzyme A reductase, or HMG-CoA reductase), the rate-limiting enzyme in de novo cholesterol synthesis. This effect was not observed in the livers of HFD-fed mice treated with CD1530 (RARγ agonist), showing specificity of AC261066 for RARβ2 (FIG. 1B). Gene expression of pepck, which is the rate-limiting enzyme in gluconeogenesis, was not affected by either AC261066 or CD1530 (FIG. 25B). Together, these data demonstrate that specific agonist activation of the transcription factor RARβ2 results in a significant reduction of both serum triglyceride and total cholesterol levels in the high fat diet fed mice, which coincides with hepatic transcriptional changes supporting suppression of de novo triglyceride and cholesterol synthesis. Collectively, these data strongly indicate that synthetic RARβ2 agonists are novel cholesterol lowering drugs.

TABLE 4

Gene ID and Abbreviations

| | Mouse Gene ID | Human counterpart gene gene ID |
|---|---|---|
| DGAT1, diglyceride acyltransferase 1 | 13350 | 8694 |
| FAS, fatty acid synthase | 14104 | 2194 |
| FGF21, fibroblast growth factor 21 | 56636 | 26291 |
| HMGCR, 3-hydroxy-3-methylglutaryl-Coenzyme A reductase | 15357 | 3156 |
| HPRT, hypoxanthine guanine phosphoribosyl transferas | 15452 | 3251 |
| PEPCK, phosphoenolpyruvate carboxykinase 1, cytosolic | 18534 | 5105 |
| PPARα, peroxisome proliferator activated receptor alpha | 19013 | 5465 |
| PPARγ, peroxisome proliferator activated receptor gamma | 19016 | 5468 |
| SIRT1, sirtuin 1 | 93759 | 23411 |
| SREBP1C, sterol regulatory element binding transcription factor 1c | 20787 | 6720 |
| SREBP2, sterol regulatory element binding transcription factor 2 | 20788 | 6721 |

Example 16

Figure 27:
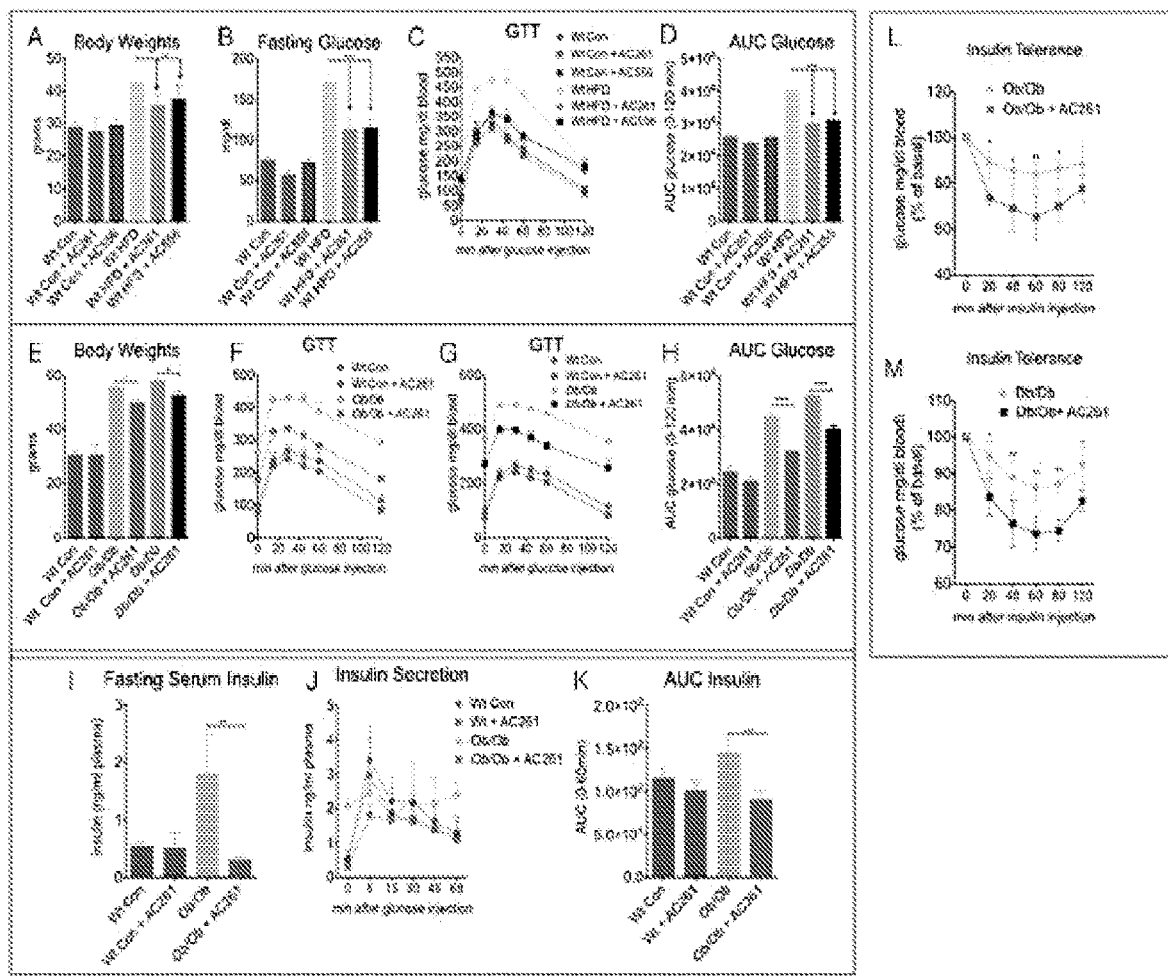
FIG. 27. Retinoic Acid Receptor β (RARβ) agonists diminish diet induced body weight increases, glucose intolerance and insulin resistance in high fat and genetic models of diabetes. A) Body weights of wild type C57/B16 male mice after 4 months of being fed either: a standard chow (13% Kcal/fat) diet (Wt Con, n=4), a high fat (45% Kcal/fat) diet (HFD, n=5) or Con and HFD with the RARβ agonists AC261066 (Wt Con+AC261, n=3, Wt HFD+AC261, n=4) or AC55649 (Wt Con+AC556, n=3, Wt HFD+AC556, n=4), in their drinking water. E) Body weights of genetically obese and diabetic Ob/Ob and Db/Db mice that were fed either a standard chow diet (n=3 per group), or a chow diet plus AC261 (n=3 per group) in their drinking water as described in A for 8 weeks. B-D) and F-H) Fasting glucose, glucose tolerance tests (GTT) and Area Under the Curve Glucose (AUC) from wt and Ob/Ob and Db/Db mice described in A an E. I-K) Fasting insulin and insulin secretion and AUC insulin of Ob/Ob and Db/Db mice subjected to GTT. L-M) Insulin tolerance testing (ITT) of Ob/Ob and Db/Db mice described in E. Errors bars represent ±SEM. *=p<0.05, =p<0.01, *=p<0.001, ****=p<0.0001.

Retinoic Acid Receptor β (RARβ) Agonists Diminish Body Weight, Diet Induced Glucose Intolerance and Insulin Resistance in High Fat and Genetic Models of Diabetes. Our metabolic studies showed that both RARβ agonists AC261066 and AC55649 lead to significant reductions in body weights of obese, high fat (HF)-fed mice (FIG. 27A) and in genetically obese and diabetic Ob/Ob and Db/Db mice (FIG. 27E). Our metabolic studies also revealed that administration of both RARβ agonists lead to a reversal of hyperglycemia in diabetic HF-fed (FIG. 27C, D) and genetically obese diabetic mice (FIG. 27F, G, H). Given that mice treated with RARβ agonists had lowered glucose levels we then sought to determine if RARβ agonists could improve insulin secretion and whole body insulin metabolism, both of which are typically altered in individuals with type 2 diabetes (T2D). Our insulin metabolism studies showed administration of RARβ agonists to genetically obese diabetic Ob/Ob and Db/Db mice led to improved insulin metabolism (FIG. 27L, M). We also found that Ob/Ob mice treated with the RARβ AC261066 had decreased pancreatic insulin secretion, which is a indicator of improved pancreatic function.

Example 17

Figure 28:
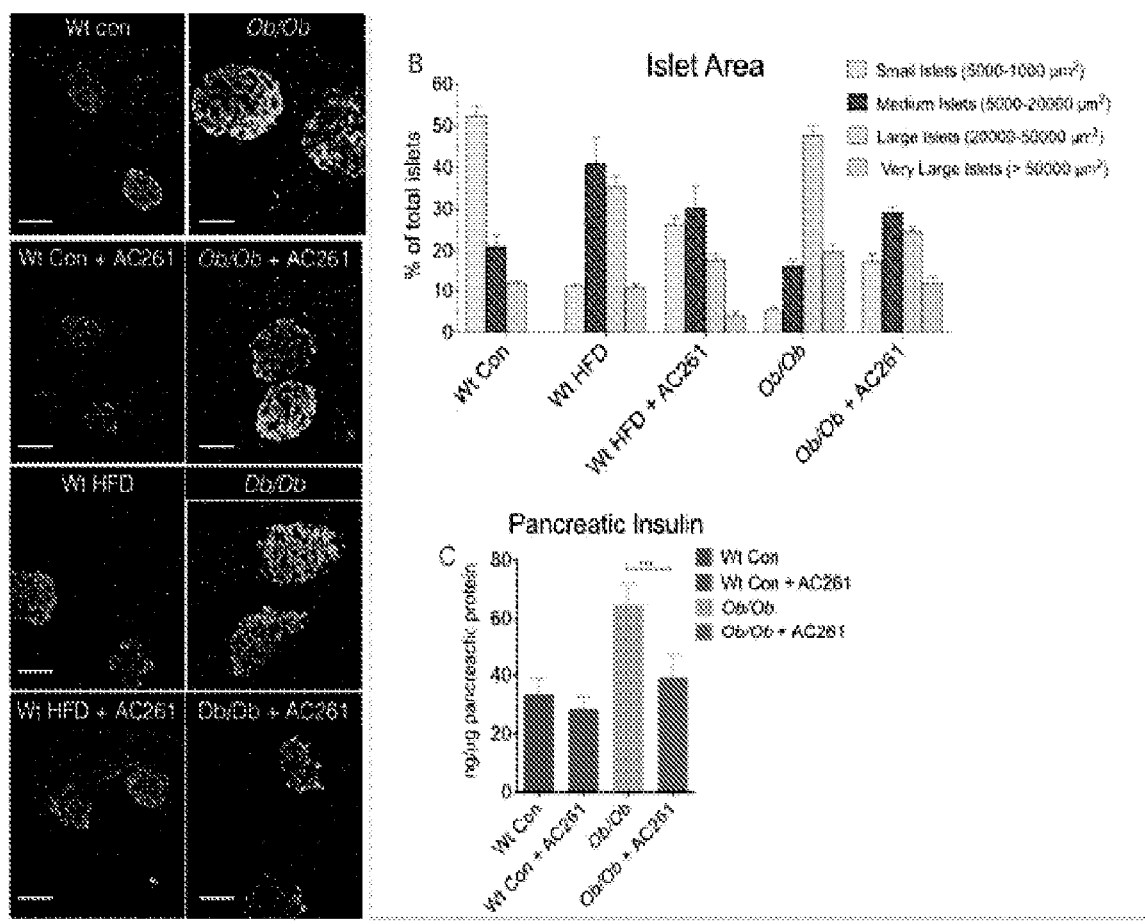
FIG. 28. Retinoic Acid Receptor β (RARβ) agonist AC261066 diminishes the number of large pancreatic islets and pancreatic insulin content in Ob/Ob and Db/Db models of obesity and diabetes. A) Representative images of pancreatic islets immunofluorescence stained with antibodies against insulin (green) in Wt and Ob/Ob and Db/Db mice fed experimental diets as descried in FIG. 1A and FIG. 1E respectively. Magnification 400×, Scale Bars=100 μm. B) Relative percentages of very large islets: (area>50,000 μm2), large islets: (area=20,000-50,000 μm2) medium islets: (area=5,000-20,000 μm2) and small islets: (area=1,000-5000 μm2) in Wt and Ob/Ob mice fed experimental diets with and without the RARβ agonist as descried in FIG. 27A and FIG. 27E respectively. C) Pancreatic insulin content (ng/μg of pancreatic protein) in Wt Con and Ob/Ob mice fed experimental diets with and without the RARβ agonist as descried in FIG. 27A and FIG. 27E respectively. Errors bars represent ±SEM. ***=p<0.0001.

Retinoic Acid Receptor β (RARβ) Agonists Diminishes the Number of Large Pancreatic Islets and Pancreatic Insulin content in Ob/Ob and Db/Db Models of Obesity and Diabetes. Early stages of T2D begins with altered insulin metabolism referred to as insulin resistance (IR), which leads to enlargement of the insulin producing cells of pancreas known as β-cells and overproduction of insulin to compensate for the IR. Our metabolic studies revealed that RARβ agonists could improve IR and as a result decrease pancreatic insulin secretion. Therefore we then sought to determine if RARβ agonists reduce the enlargement of β-cells in HF-fed and genetically diabetic mice. Using immunohistochemistry and an anti-body for insulin, we examined pancreas sections and found that RARβ agonists led to the reduction pancreatic β-cells (also known as Islets) and pancreatic insulin content (FIG. 28A, B). Collectively our metabolic and pancreas studies demonstrate that RARβ agonists i) reduce obesity in HF-fed an genetically obese Ob/Ob and Db/Db mice, ii) improve glucose intolerance and peripheral insulin resistance in a dietary and genetic model of obesity and diabetes.

Example 18

Figure 29:
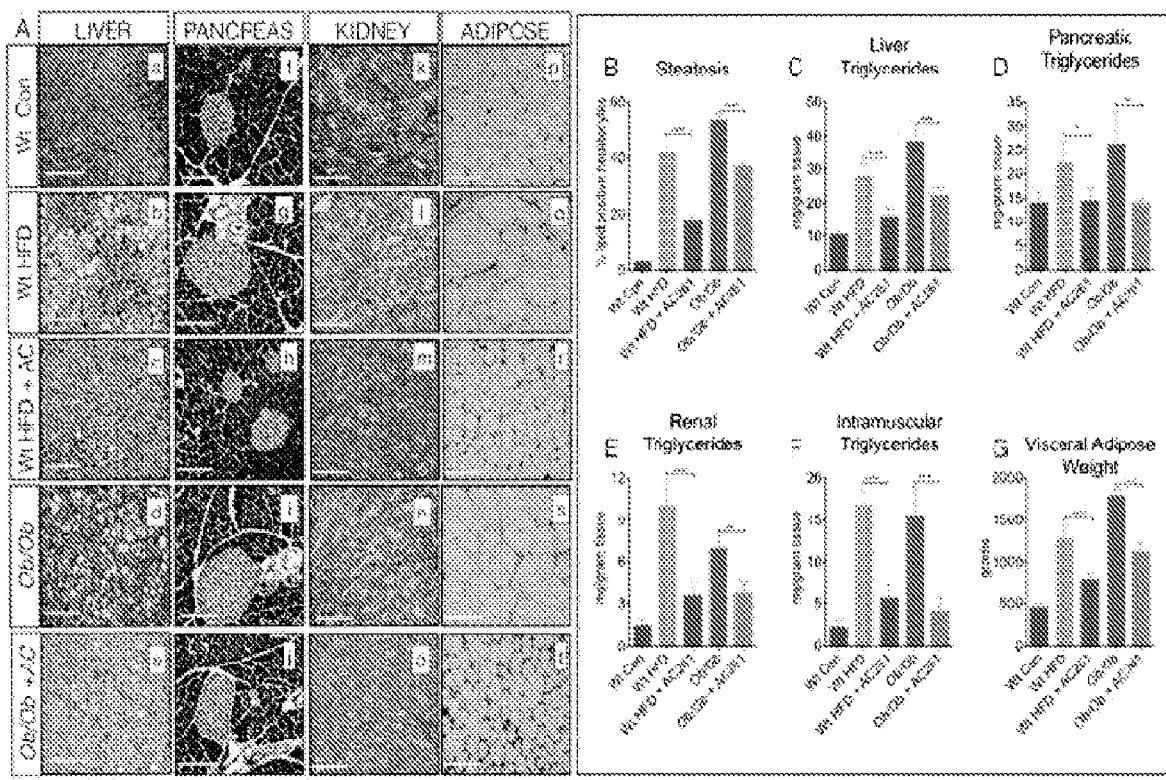
FIG. 29. Retinoic Acid Receptor β (RARβ) agonist AC261066 reduces the accumulation of liver, pancreas, kidney, muscle and adipose triglycerides in dietary and genetic models of diabetes. A) Representative images of Hematoxylin and Eosin stained liver (a-e), pancreas (f-j), kidney (k-o) and adipose tissue (p-t) from Wt and Ob/Ob mice fed experimental diets with and without the RARβ agonist as descried in FIG. 1A and FIG. 1E. Magnification 200×, Scale Bars=50 μm. B) Percent hepatic steatosis and C-F) tissue triglycerides in Wt and Ob/Ob mice fed experimental diets with and without the RARβ agonist as descried in FIG. 27A and FIG. 27E. G) Total adipose tissue weights in Wt and Ob/Ob mice fed experimental diets with and without RARβ agonist as descried in FIG. 27A and FIG. 27E. Errors bars represent ±SEM. *=p<0.05, =p<0.01, **=p<0.0001.

Retinoic Acid Receptor β (RARβ) Agonists Reduce the Accumulation of Liver, Pancreas, Kidney, Muscle and Adipose Triglycerides in Dietary and Genetic Models of Diabetes. Obesity leads to the accumulation of lipids in organs such as the liver, kidney and adipose tissue. Excessive lipids in organs can alter their function and lead to IR and promote the pathogenesis of T2D. Given the reductions in body weight and improved metabolic profile in mice treated with RARβ agonists, we examined the organs of HF and genetically obese diabetic mice for the presence of lipids. Our analysis of Hematoxylin and Eosin stained liver, pancreas, kidney and adipose tissue showed that HF-fed and genetically obese mice treated with RARβ agonists had significant reductions in lipids (triglycerides) in their liver (FIG. 29A [a-e] B, C), pancreas (FIG. 29A[f-j], D), kidneys (FIG. 29A[k-o], E), muscle, (FIG. 29F) and adipose tissue (FIG. 29A[p-t], G).

Example 19

Figure 30:
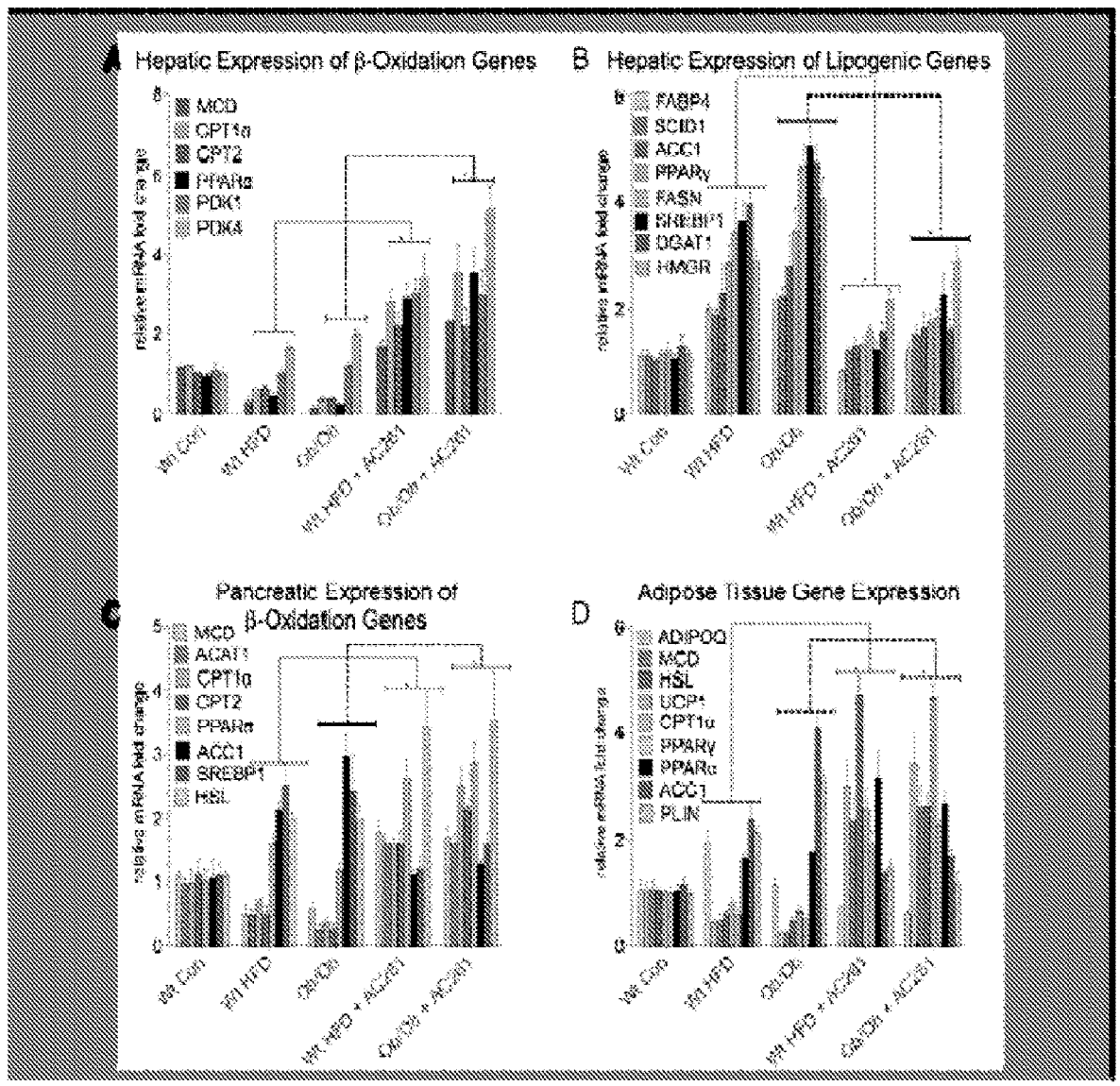
FIG. 30. Retinoic Acid Receptor β (RARβ) agonist AC261066 alters tissue expression of genes involved in lipogenesis and mitochondrial oxidation of lipids. Real-time PCR measurements of relative hepatic, pancreatic and adipose tissue transcript levels of genes involved in lipid metabolism from Wt and Ob/Ob mice fed experimental diets with and without the RARβ agonist as descried in FIG. 27A and FIG. 27E. A) Relative hepatic mRNA levels of genes involved in mitochondrial β-oxidation of lipids. B) Relative hepatic mRNA levels of genes involved in lipogenesis. C) Relative pancreatic mRNA levels of genes involved in mitochondrial β-oxidation of lipids. D) Relative adipose mRNA levels of genes involved in lipid metabolism. Relative fold mRNA levels were normalized to transcript levels of Hprt. Errors bars represent±SEM of (n=3-5) animals per experimental group.

Retinoic Acid Receptor β (RARβ) Agonist AC261066 Alters Tissue Expression of Genes Involved in Lipogenesis and Mitochondrial Oxidation of Lipids. Tissue lipids can be altered by increasing lipid breakdown (catabolism) and/or by diminishing lipid synthesis. With the exception of the liver, most organs do not synthesize lipids and will utilize lipids delivered through the blood. Type 2 diabetes (T2D) is associated with a decreased ability of organs such as muscle to catabolize lipids thus leading to the accumulation of excess lipids. We examined the expression of genes involved in the process of catabolism of lipids known as β-oxidation and in lipid synthesis in liver, pancreas, and adipose tissue. Our gene expression analysis revealed that liver, pancreas and adipose tissue from HFD-fed and genetically obese mice treated with RARβ agonist had significant increases in genes that stimulate β-oxidation of lipids including the transcription factor PPARα, the transporter proteins CPT1-α and CPT2 and the lipid catabolic enzyme acetyl-CoA acetyltransferase 1 (ACAT1) (FIGS. 30A, C and D). In liver and pancreas we also detected a significant decrease in expression of genes involved in the suppression of β-oxidation and stimulation of lipogensis, including the rate limiting enzyme in de novo fatty acid synthesis fatty acid synthase (FASN), the lipogenic transcription factor SREBP1 and acetyl-CoA acetyltransferase 1 (ACC1) (FIGS. 30B, and C). Consistent with the decreases in body and adipose tissue weights, RARβ agonist treatment also led to a significant increase in genes responsible for adipocyte lipolysis such as hormone sensitive lipase (HSL) and perilipin (PLIN) (FIG. 30D). Adipose tissue expression of the gene adiponectin (ADIPOQ), which is decreased in individuals with T2D and shown to stimulate oxidation of lipids in peripheral tissue, was significantly increased in RARβ-treated HFD-fed and genetically diabetic mice (FIG. 30D). Collectively our gene expression studies strongly suggest that RARβ agonist can regulate pathways in liver, pancreas and adipose tissue that lead to an increase the β-oxidation of lipids and a decrease in lipogenesis. The ability of AC261066 to increase lipid energy metabolism in organs that are central to glucose—energy metabolism and the pathogenesis of T2D suggests that glucose lowering and insulin sensitizing effects of this RARβ agonist are likely associated with modulation of lipid energy metabolism.

Example 20

Figure 31:
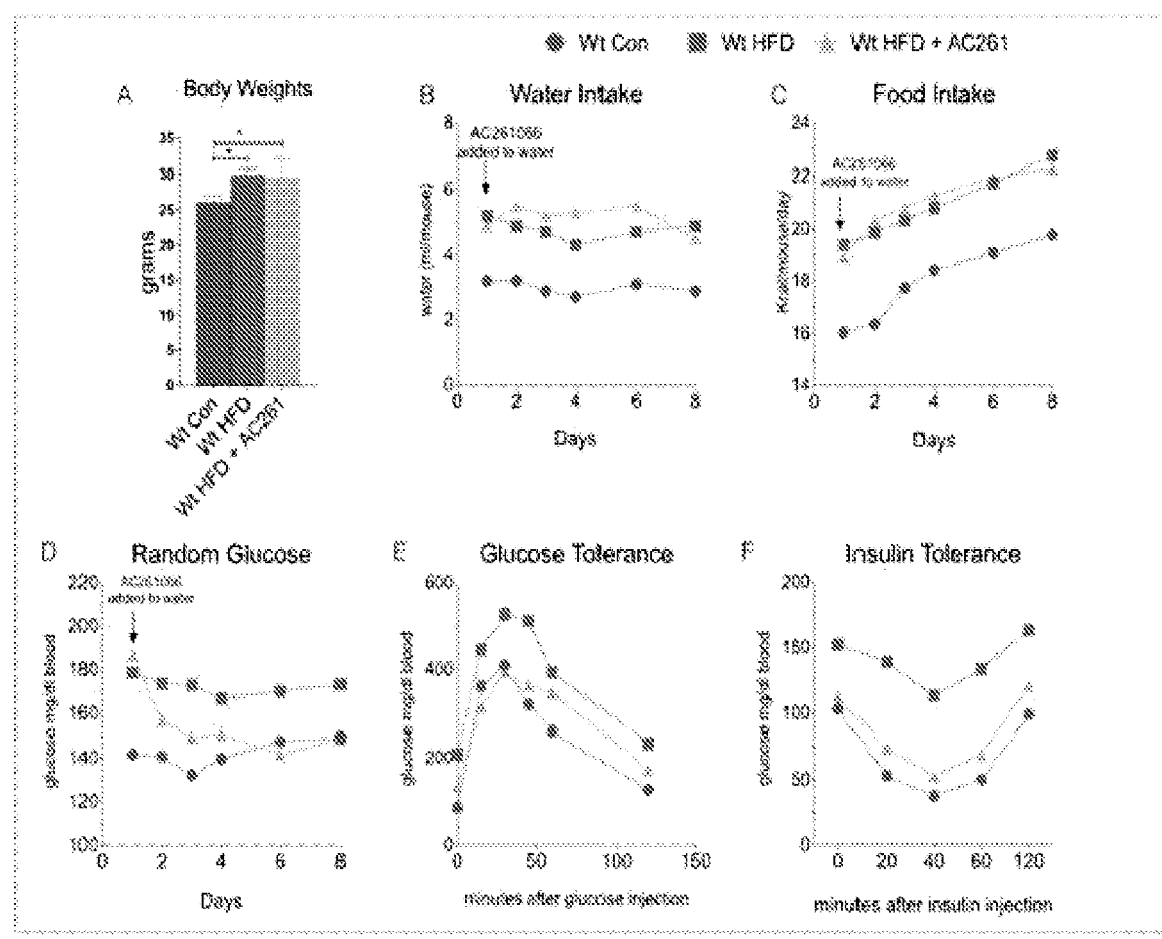
FIG. 31. Acute administration of Retinoic Acid Receptor β (RARβ) agonist AC261066 reverses high fat induced glucose intolerance and insulin resistance. A-C) Body weights, water and food intake of wild type C57/B16 male mice after 3 months of being fed either: a standard chow (13% Kcal/fat) diet (Wt Con, n=4), a high fat (45% Kcal/fat) diet (HFD, n=4) or 3 months of a HFD mice plus 8 days of administration of the RARβ agonist AC261066 (n=4) in their drinking water at a dose of 5.4 mg/Kg BW/day. On day 8 mice were tested for glucose intolerance and insulin resistance. D and E) Random glucose and glucose tolerance test (GTT) of mice described in A. F) Insulin tolerance test of mice described in A.

Acute Administration of Retinoic Acid Receptor β (RARβ) Agonist Reverses High Fat Induced Glucose Intolerance and Insulin Resistance. We tested if acute administration (8 days) of the RARβ agonist AC261066 could ameliorate hyperglycemia and insulin resistance in diabetic HFD-fed mice. Acute administration of AC261066 to HF-fed mice had no effect on body weights, food or water intake (FIGS. 31A, B and C). Our acute studies revealed that after 24 hours of administration of AC261066, HFD-fed mice had significant reductions in random glucose levels (FIG. 31D) and after 8 days of administration of the AC261066 HFD-fed mice had significant reductions in hyperglycemia and insulin resistance (FIGS. 31E and F). Our acute metabolic studies of AC261066 demonstrate that this RARβ agonist can acutely improve hyperglycemia and insulin as effective as those observed with long-term administration of RARβ agonist. The expression profile of one or more such genes (e.g., as listed in Table 5 below) may be a therapeutic effect indicator which may be used to direct therapeutic regimen and doses according to the present invention.

Example 21

Methods for Certain Examples

Mice, diet, and drug treatment. Dietary Obesity Studies: Wild type (wt) male C57/BL6 male mice were maintained on either a standard laboratory chow-fed diet (Con) with 13% kcal fat, (diet #5053, Lab Diet, Inc, St. Louis, Mo.) or a high fat, western style diet (HFD) with 45% kcals from fat, (diet #58126, Lab Diet, Inc., St. Louis, Mo.) for 4 months. One month after the start of the HFD treatment, the Con and HFD groups werefurther split into 3 additional groups for 4 months to: i) remain on either Con or HFD and the drinking water containing 1% DMSO; ii) Con or HFD and drinking water containing 3.0 mg/100 ml AC261066, a specific RARβ agonist in 1% DMSO, or iii) Con or HFD and drinking water containing 3.0 mg/100 ml of AC55649, another specific RARβ agonist in 1% DMSO. All mice remained on their diets for 4 months. After 4 months mice were subjected to metabolic studies and then sacrificed by cervical dislocation and tissues were snap frozen at −70° C. for future RNA isolation and histology. Genetically obese mice studies: Lep$^{-ob}$ and Lepr-$^{db}$ mice commonly referred to as ob/ob (stock #000632, Jackson Labs, Bar Harbor, Me.) and db/db (stock #000642, Jackson Labs, Bar Harbor, Me.) mice respectively. Ob/ob and db/db mice are homozygous knockout mice for the leptin (ob) or leptin receptor (db) genes. Both ob/ob and db/db mice were developed in a C57BL/6J background strain and both genetic alterations leads to spontaneous development of obesity by 4-5 weeks of age when fed a standard laboratory chow diet.

5-week-old male ob/ob (n=6) and db/db (n=6) mice were housed using a 12 h light dark cycle and received ad libitum access to a standard laboratory chow-fed diet (Con) with 13% kcal fat, (diet #5053, Lab Diet, Inc, St. Louis, Mo.) and drinking water. After one week ob/ob and db/db mice were randomly divided to receive either: i) con diet and drinking water containing 1% DMSO (n=3); or ii) con diet with drinking water containing 3.0 mg/100 ml AC261066. All mice remained on their diets for 8 weeks. After 8 weeks all mice were subjected to metabolic studies and then sacrificed by cervical dislocation and tissues were snap frozen at −70° C. for future RNA isolation and histology.

Metabolic Measurements-Glucose tolerance was performed using an intraperitoneal glucose tolerance test (GTT) as previously described (Trasino et al., Vitamin A Deficiency Causes Hyperglycemia and Loss of Pancreatic β-Cell Mass, J Biol Chem. 2014 Dec. 1. pii: jbc.M114.616763). Mice were fasted overnight followed by intra-peritoneal injections (n=3-5 per group) of 50% glucose in PBS at 2.0 g of glucose/kg of body weight. Tail vein blood was collected at 15, 30, 45, 60, and 120 minutes post-injection for glucose measurements using a FreeStyle Lite Blood Glucose Monitoring System (Abbott Diabetes Care, Inc. Alameda, Calif.). Insulin tolerance tests (ITT) were performed as previously described (Trasino et al., Vitamin A Deficiency Causes Hyperglycemia and Loss of Pancreatic β-Cell Mass, J Biol Chem. 2014 Dec. 1. pii: jbc.M114.616763). Mice were fasted for 4 hours followed by intra-peritoneal injections with insulin (Humulin R; Eli Lilly, 2 U/kg of body weight). Tail vein blood glucose was measured at 20, 40, 60 and 120 minutes after injection using a FreeStyle Lite Blood Glucose Monitoring System (Abbott Diabetes Care, Inc. Alameda, Calif.). To determine insulin secretion responses to glucose, serum fractions were isolated between 0-60 minutes post glucose injections and insulin concentrations were measured using an Ultrasensitive Insulin ELISA Kit (Alpco, Inc. Salem, N.H.). Random blood glucose measurements were taken from tail veins of 4 mice per group at 2-3 random time points daily Means are expressed as ±standard error of the mean (S.E.M) and P-values were calculated using one-way analysis of variance followed by Bonferroni post-hoc analysis.

Immunofluorescence and Immunostaining Microscopy—Paraffin embedded pancreatic tissue sections were incubated with antibodies against: insulin (mouse monoclonal 1:300, #1061, Beta Cell Biology Consortium). We utilized Alexafluor 488 conjugated anti-mouse secondary antibody (1:500) (Invitrogen, Carlsbad, Calif.) for immunofluorescence labeling of insulin followed by visualization using a Nikon TE2000 inverted fluorescence microscope (Nikon, Inc).

Pancreatic Insulin Measurements—Pancreatic insulin levels were measured in lysates from pancreatic tissues using an ultrasensitive Insulin ELISA Kit (Alpco, Inc. Salem, N.H.) as per the manufacturers' instructions. Insulin concentrations were normalized to pancreatic protein concentrations determined using the DC protein assay (Bio-Rad, Inc. Hercules, Calif.) according to the manufacturers' protocol. Endocrine hormones levels are reported as mean±standard error of the mean (S.E.M) and P-values calculated using one-way analysis of variance followed by Bonferroni multiple comparison test post-hoc analysis.

RNA Isolation and cDNA Synthesis—Total RNA was isolated from whole pancreas and small intestine homogenates using RNeasy mini kits (Qiagen, Valencia, Calif.) and quantified using a Nano Drop 2000 spectrophotometer (Thermo Scientific, Wilmington, Del.). Total RNA (2 µg) was used to synthesize cDNA with random primers using a qScript cDNA synthesis kit (Quanta Biosciences, Gaithersburg, Md.).

Measurement of Pancreatic Endocrine Cell Mass.—Pancreatic endocrine cell mass was determined using a direct point counting method as previously described. Between 100-200 insulin positive fields per mouse were photographed using a using a Nikon TE2000 inverted fluorescence microscope (Nikon, Inc) and analyzed for β-cell by using the following formula: β-cell mass (mg)=total insulin positive islet area (µm$^2$)/total pancreatic tissue area (µm$^2$)× pancreatic tissue weight (mg). Endocrine cell mass is reported as mean±standard error of the mean (S.E.M) and P-values were calculated using one-way analysis of variance followed by Bonferroni multiple comparison test post-hoc analysis.

Tissue Triglyceride Analysis: Total tissue lipids were extracted from using the Folch method. Briefly, total lipids were extracted from aliquots of tissue homogenates using chloroform: methanol (2:1) and partitioned using dH2O. Organic phase solvents containing lipids were evaporated under nitrogen gas and re-suspended in 0.5% (v/v) Triton X-100 solution in water. Tissue triglycerides were determined enzymatically using Triglycerides Reagent kit (Invitrogen, Life Technologies, Carlsbad, Calif., USA) according to the manufacture's protocol. Tissue triglycerides were normalized to tissue protein concentrations and reported as mean±standard error of the mean (S.E.M) and P-values were calculated using one-way analysis of variance followed by Bonferroni multiple comparison test post-hoc analysis.

Quantitative RT-PCR (Q-PCR)-Q-PCR was performed using SYBR Green PCR master mix on a Bio-Rad MyiQ2 Real Time PCR iCycler (Bio-Rad, Inc. Hercules, Calif.). Gene specific primers (Table 5) were used to amplify mRNA target genes, which were normalized to Hprt internal control genes. cDNA from 3-5 mice per experimental group was analyzed for relative mRNA fold changes, calculated using the Pfaffl method (Pfaffl M W, A new mathematical model for relative quantification in real-time RT-PCR, Nucleic Acids Res. 2001 May 1; 29(9):e45). Relative gene expression values are reported as mean±standard error of the mean (S.E.M) and P-values calculated using one-way analysis of variance followed by Bonferroni multiple comparison test post-hoc analysis.

TABLE 5

| Gene Symbol | Gene Name | NCBI Gene ID | Forward Primer (5'-3') | Reverse Primer (5'-3') |
|---|---|---|---|---|
| Pathway: Lipogenesis | | | | |
| ACC1 | Acetyl-Coenzyme A carboxylase alpha | 107476 | ATGGGCGGAATGGTCTCTTTC (SEQ ID NO. 61) | TGGGGACCTTGTCTTCATCAT (SEQ ID NO. 62) |
| DGAT1 | Diacylglycerol O-acyltransferase 1 | 13350 | ATGATGGCTCAGGTCCCACT (SEQ ID NO. 63) | CACTGGGGCATCGTAGTTGA (SEQ ID NO. 64) |
| FABP4 | Fatty Acid Binding Protein 4 | 11770 | TGAAATCACCGCAGACGACA (SEQ ID NO. 65) | ACACATTCCACCACCAGCTT (SEQ ID NO. 66) |
| FASN | Fatty Acid Synthase | 14104 | GGAGGTGGTGATAGCCGGTAT (SEQ ID NO. 67) | TGGGTAATCCATAGAGCCCAG (SEQ ID NO. 68) |
| HMGCR | 3-hydroxy-3-methylglutaryl-coenzyme A reductase | 15357 | AGCTTGCCCGAATTGTATGTG (SEQ ID NO. 69) | TCTGTTGTGAACCATGTGACTTC (SEQ ID NO. 70) |
| PPARγ | Peroxisome proliferator-activated receptor gamma | 19016 | CTCCAAGAATACCAAAGTGCGA (SEQ ID NO. 71) | GCCTGATGCTTTATCCCCACA (SEQ ID NO. 72) |
| SCD1 | Stearoyl-Coenzyme A desaturase 1 | 20249 | GCTCTACACCTGCCTCTTCG (SEQ ID NO. 73) | CAGCCGAGCCTTGTAAGTTC (SEQ ID NO. 74) |
| SREBP1 | Sterol regulatory element binding transcription factor 1 | 20787 | CAAGGCCATCGACTACATCCG (SEQ ID NO. 75) | CACCACTTCGGGTTTCATG (SEQ ID NO. 76) |
| Pathway: Lipid β-Oxidation | | | | |
| ACAT1 | Acetyl-Coenzyme A acetyltransferase 1 | 110446 | AGCCTTTCGCGTCTCCAT (SEQ ID NO. 77) | TGCATAACTTCGTTCCAGGC (SEQ ID NO. 78) |
| CPT1α | Carnitine palmitoyltransferase 1a | 12894 | GCCCATGTTGTACAGCTTCC (SEQ ID NO. 79) | AGTGGCCTCACAGACTCCAG (SEQ ID NO. 80) |
| CPT2 | Carnitine palmitoyltransferase 2 | 12896 | CAGCACAGCATCGTACCCA (SEQ ID NO. 81) | TCCCAATGCCGTTCTCAAAAT (SEQ ID NO. 82) |
| MCD | malonyl-CoA decarboxylase | 56690 | GCACGTCCGGGAAATGAAC (SEQ ID NO. 83) | GCCTCACACTCGCTGATCTT (SEQ ID NO. 84) |
| PDK1 | Pyruvate dehydrogenase kinase, isoenzyme 1 | 228026 | GTTTATCCCCCGATTCAGGT (SEQ ID NO. 85) | TTACTCAGTGGAACACCGCC (SEQ ID NO. 86) |
| PDK4 | Pyruvate dehydrogenase kinase, isoenzyme 4 | 27273 | AGTGAACACTCCTTCGGTGC (SEQ ID NO. 87) | TGACAGGGCTTTCTGGTCTT (SEQ ID NO. 88) |
| PPARα | Peroxisome proliferator-activated receptor alpha | 19013 | AGAGCCCCATCTGTCCTCTC (SEQ ID NO. 89) | ACTGGTAGTCTGCAAAACCAAA (SEQ ID NO. 90) |

TABLE 5-continued

Gene Expression Primers

| Gene Symbol | Gene Name | NCBI Gene ID | Forward Primer (5'-3') | Reverse Primer (5'-3') |
|---|---|---|---|---|
| Pathway: Adipocyte Metabolism | | | | |
| ADIPOQ | Adiponectin | 11450 | TGTTCCTCTTAATCCTGCCCA (SEQ ID NO. 91) | CCAACCTGCACAAGTTCCCTT (SEQ ID NO. 92) |
| PLIN1 | Perilipin1 | 103968 | TGAAGCAGGGCCACTCTC (SEQ ID NO. 93) | GACACCACCTGCATGGCT (SEQ ID NO. 94) |
| HSL | Hormone sensitive lipase | 16890 | GATTTACGCACGATGACACAGT (SEQ ID NO. 95) | ACCTGCAAAGACATTAGACAGC (SEQ ID NO. 96) |
| UCP1 | Uncoupling protein 1 | 22227 | GTGAACCCGACAACTTCCGAA (SEQ ID NO. 97) | TGCCAGGCAAGCTGAAACTC (SEQ ID NO. 98) |
| Pathway: Inflammation and Fibrosis | | | | |
| MCP-1 | Monocyte chemoattractant protein-1 | 20296 | TTAAAAACCTGGATCGGAACCAA (SEQ ID NO. 99) | GCATTAGCTTCAGATTTACGGGT (SEQ ID NO. 100) |
| TNF-α | Tumor necrosis factor-alpha | 21926 | CCTGTAGCCCACGTCGTAG (SEQ ID NO. 101) | GGGAGTAGACAAGGTACAACCC (SEQ ID NO. 102) |
| α-SMA | alpha-Smooth muscle actin | 11475 | GTCCCAGACATCAGGGAGTAA (SEQ ID NO. 103) | TCGGATACTTCAGCGTCAGGA (SEQ ID NO. 104) |
| Pathway: Housekeeping Reference Gene | | | | |
| HPRT | Hypoxanthine guanine phosphoribosyl transferase | 15452 | GCTTGCTGGTGAAAAGGACCTCTCGAAG (SEQ ID NO. 105) | CCCTGAAGTACTCATTATAGTCAAGGGCAT (SEQ ID NO. 106) |

Example 22

Figure 32:
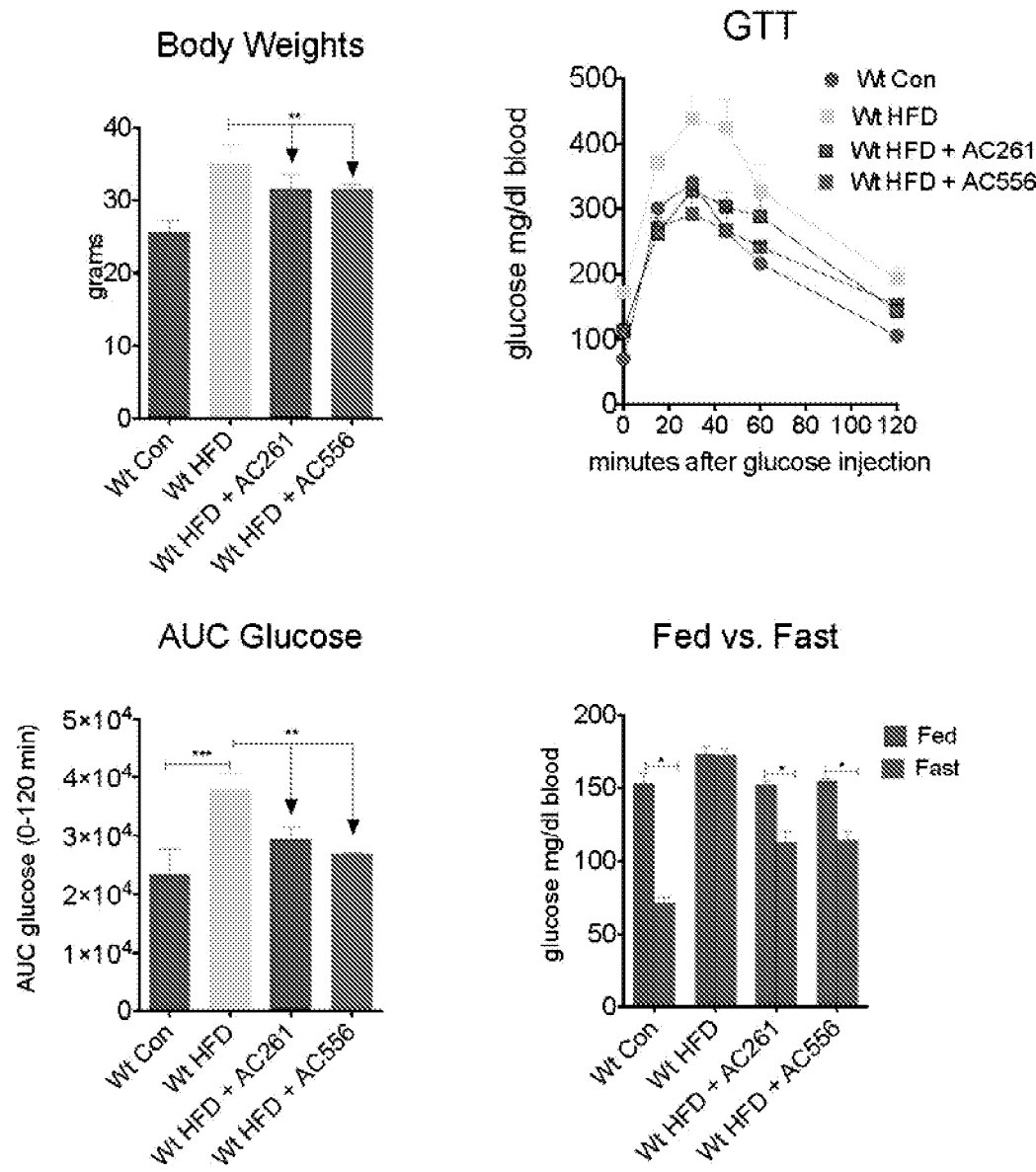
FIG. 32. Retinoic Acid Receptor β (RARβ) agonists diminish diet induced body weight increases and glucose intolerance in a high fat model of diabetes. A) Body weights of wild type C57/B16 male mice after 3 months of being fed either: a standard chow (13% Kcal/fat) diet (Wt Con, n=4), a high fat (45% Kcal/fat) diet (HFD, n=5) or a HFD with the RARβ agonists AC261066 (HFD+AC261, n=5) or AC55649 Wt HFD+AC556, n=4), in their drinking water. B and C) Glucose tolerance tests (GTT) and Area Under the Curve Glucose (AUC) from mice described in A. D) Blood glucose level in randomly tested (fed) mice and from mice fasted for 16 hours as described in A. Errors bars represent±SEM. *=p<0.05, =p<0.01, *=p<0.001.

Retinoic Acid Receptor β (RARβ) Agonists Diminish Diet Induced Body Weight Increases and Glucose Intolerance in a High Fat Model of Diabetes. Three months of HF-fat (45% Kcal/fat) feeding led to a significant increase in body weight compared to con-fed mice (FIG. 32A). However compared to HF-fed mice, HF-fed mice treated with AC261066 or AC55649 for 3 months had approximately a 10% decrease in body weights (FIG. 32A). Metabolic studies demonstrated that water administration of the RARβ AC261066 and AC55649 lead to improved glucose tolerance and area under the curve glucose in HF-fed mice (FIG. 32B, C). Compared to con-fed mice, blood glucose levels HF-fed mice were unchanged after an overnight fast suggesting impaired insulin signaling and peripheral insulin resistance (FIG. 32D). HF-fed mice treated with AC261066 or AC55649 had significant reductions in overnight fasting glucose levels (FIG. 32D). Collectively these data demonstrate that administration of the specific RARβ agonists AC261066 and AC55649 for 3 months can decrease body weight and ameliorate impaired glucose tolerance in HF-fed obese mice. These studies suggest that AC261066 or AC55649 may also lead to improved hepatic and extra-hepatic glucose and insulin metabolism based on the significant reductions in feed to fasting overnight glucose levels.

METHODS. Preparation of RARβ agonists solution. AC261066 and AC55649 were dissolved in dimethyl sulfoxide (DMSO) at the concentration of 3.0 mg/ml and diluted in the drinking water for mice to the final concentration of 3.0-mg/100 ml. Mice, diet, and drug treatments. Wt male C57/BL6 male mice were maintained on either a standard laboratory chow-fed diet (Con) with 13% kcal fat, (diet #5053, Lab Diet, Inc, St. Louis, Mo., [n=4]) or a high fat, western style diet (HFD) with 45% kcals from fat, (diet #58126, Lab Diet, Inc., St. Louis, Mo.) for 3 months. Two weeks after the start of the HFD treatment, the HFD group was further split into 3 groups for 3 months: i) HFD and drinking water containing 1% DMSO (n=5); ii) high fat diet (HFD) and drinking water containing 3.0 mg/100 ml AC261066, a specific RARβ agonist (n=5) or iii) HFD and drinking water containing 3.0 mg/100 ml AC55649, a specific RARβ agonist (n=4). After 3 months the mice were tested for glucose intolerance with an intra-peritoneal glucose tolerance test (GTT). Mice were then sacrificed by cervical dislocation. Blood and various tissue samples were harvested.

Glucose Tolerance Test (GTT). Glucose tolerance was performed using an intraperitoneal glucose tolerance test (GTT). Mice were fasted overnight (~16 hrs) followed by intra-peritoneal injections (n=3-5 per group) of 50% glucose in PBS at 2.0 g of glucose/kg of body weight. Tail vein blood was collected at 15, 30, 45, 60, and 120 minutes post-injection for glucose measurements using a FreeStyle Lite Blood Glucose Monitoring System (Abbott Diabetes Care, Inc. Alameda, Calif.). Random and fasting blood glucose measurements were taken from tail veins of 4 mice per group at 2-3 random time points daily or just prior to GTT. Means are expressed as ±standard error of the mean (S.E.M) and P-values were calculated using one-way analysis of variance followed by Bonferroni post-hoc analysis. Grubbs' maximum normal residual test was used for detection of one or more outliers.

Example 23

Figure 33:
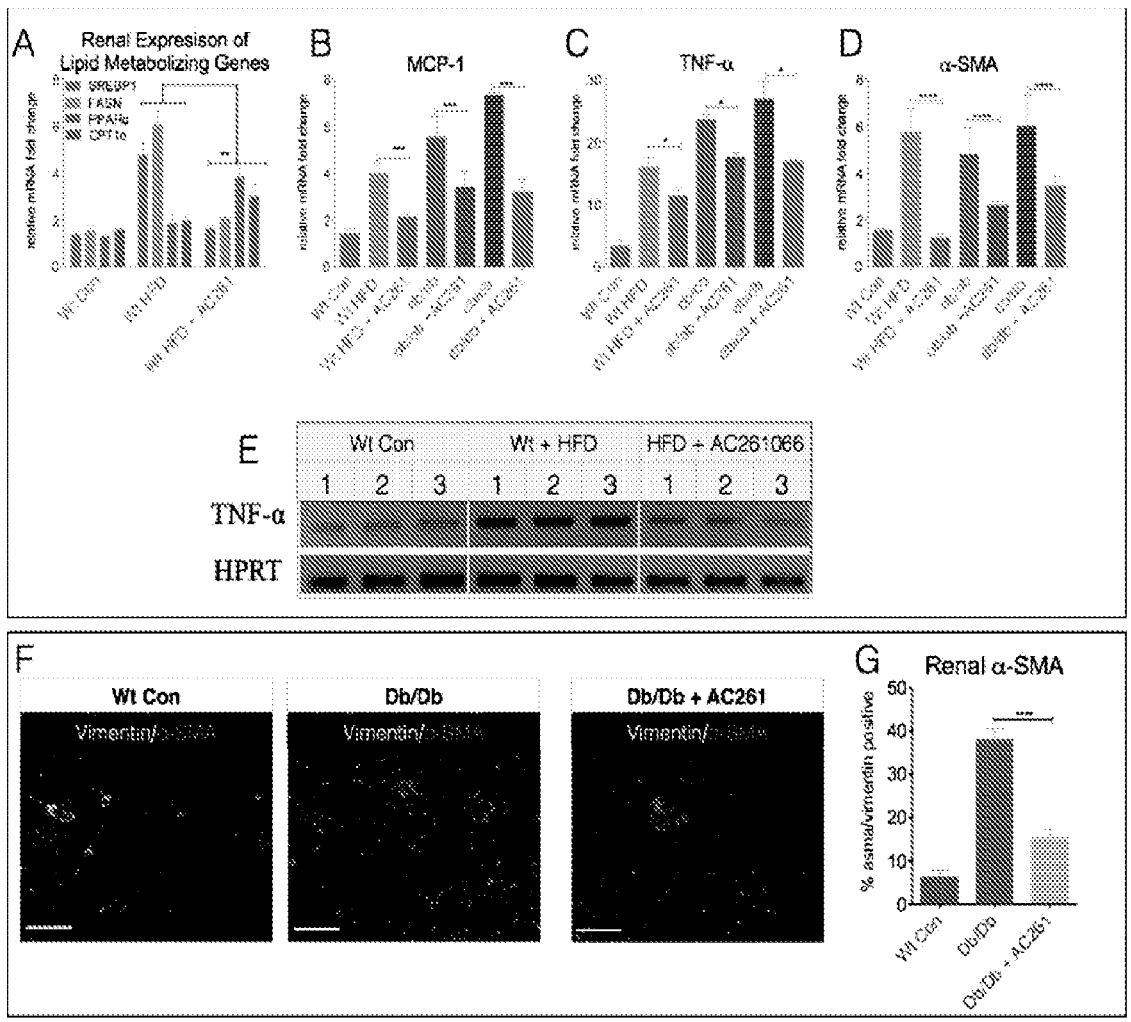
FIG. 33. Retinoic Acid Receptor β (RARβ) Agonist AC261066 Alters Renal Expression of Genes and Proteins involved in Lipid Metabolism, Inflammation and Fibrosis in Dietary and Genetic Models of Obesity and Diabetes. A) Relative kidney mRNA levels of genes involved in lipogenesis and mitochondrial β-oxidation of lipids from Wt, Ob/Ob and Db/Db mice fed experimental diets with and without the RARβ agonist AC261066. B-D) Relative kidney mRNA levels of genes involved in inflammation (MCP-1 and TNF-α) and fibrosis (α-SMA). E) Semi-quantitative PCR of TNF-α mRNA transcripts. All relative and semi-quantitative fold mRNA levels were normalized to transcript levels of Hprt. Errors bars represent±SEM of (n=3-5) animals per experimental group. F, G) Representative images of kidney tissue sections double-immunofluorescence stained with antibodies against vimentin (green) and α-SMA in Wt, Db/Db and Db/Db mice given AC261066 in their water for 8 weeks. Magnification 400×, Scale Bars=100 μm.

Retinoic Acid Receptor β (RARβ) Agonist AC261066 Alters Renal Expression of Genes involved in Lipid Metabolism and Inflammation in Models of Obesity and Diabetes. Diabetic kidney disease (aka diabetic nephropathy (DN)) frequently occurs in individuals with type 2 diabetes. The causes of DN are unclear but insulin resistance, hyperlipidemia and obesity are implicated because these states can impair renal lipid metabolism leading to the accumulation of free fatty acids (FFA), which can promote renal inflammation, fibrosis and impaired kidney function. There is evidence that transcriptions factors involved in de novo lipid synthesis such as srebp1 contribute to the pathogenesis of DN. Therefore we measured kidney mRNA transcripts of genes involved in de novo lipid synthesis (SREBP1, FASN) and β-oxidation (catabolism) of lipids (PPAR-α and CPT1-α) and found that in comparison to wt con-fed mice, HFD-fed mice had a 4-5 fold increase in kidney mRNA levels of SREBP1 and FASN (FIG. 33A). HF-fed mice treated with AC261066 had no increase in mRNA transcripts of SREBP1 and FASN (FIG. 33A). We also found that in comparison to HFD-fed mice, mRNA transcripts of PPAR-α and CPT1-α were increased approximately 2-fold in HF-fed mice treated with AC261066 (FIG. 33A).

We also measured kidney mRNA levels of pro-inflammatory and fibrogenic mediators MCP-1 (aka CCL2), TNF-α, and α-SMA in HFD-fed mice and two genetic mouse models of obesity and diabetes, Ob/Ob and Db/Db mice. MCP-1, TNF-α, and α-SMA are implicated in inflammation and fibrosis in DN and expression of these genes are frequently elevated in models of DN. Our PCR analysis results show that compared to wt con mice, HFD-fed, Ob/Ob, and Db/Db mice had a 4-8 fold and 20-30 fold increase in mRNA levels of MCP-1 (FIG. 33B) and TNF-α (FIG. 33C, E) respectively (FIG. 33B, 33C). Compared to HFD, Ob/Ob and Db/Db mice, we found that HFD, Ob/Ob and Db/Db mice treated with AC261066 had 40-50% reductions in kidney mRNA transcripts of MCP-1 (FIG. 33B) and TNF-α (FIG. 33C, E) respectively. Kidney mRNA transcripts of α-SMA, which contributes to DN fibrosis, was increased 5-6 fold in HFD Ob/Ob and Db/Db mice compared to wt con (FIG. 33D). HFD Ob/Ob and Db/Db mice treated AC261066 had 40-50% reductions in α-SMA transcripts compared to their respective HFD and genetic controls (FIG. 33D).

Retinoic Acid Receptor β (RARβ) Agonists Diminish The Activation of Fibrogenic Kidney Stellate Cells. Given that we observed a significant decrease in mRNA transcripts of α-SMA we measured kidney protein expression of α-SMA in fibrogenic renal stellate cells Renal stellate cells (RSCs) are resident kidney fibroblasts, which in response to inflammation undergo differentiation to "activated" myofibroblasts that secrete contractile proteins such as α-SMA. Quiescent RSCs do not express α-SMA, but unchecked activation of RSCs and secretion of α-SMA contributes to renal fibrosis and the pathogenesis of DN. RSCs express the mesenchymal protein marker vimentin. We used double immunofluorescence to label RSCs and determine the percentage of activated RSCs expressing the fibrogenic protein α-SMA. Using Db/Db mice, which spontaneously diabetes and DN in a similar manner to humans, we detected more than a 4-fold increase in activated α-SMA positive RSCs compared to wt con mice (FIG. 33F, G). Db/Db mice treated with AC261066 for 4 weeks had more than a 50% reduction in α-SMA positive RSCs (FIG. 33F, G).

Coupled with our PCR analysis of genes involved in lipid metabolism, inflammation and fibrogenesis, our immunofluorescence studies demonstrate in three dietary and genetic models of obesity and type 2 diabetes that treatment with the RARβ agonist AC261066 led to kidney gene and protein expression patterns consistent with a decrease in kidney lipotoxicity, inflammation and fibrogenesis and risk for developing DN.

METHODS. Immunofluorescence and Immunostaining Microscopy—Paraffin embedded pancreatic tissue sections were incubated with antibodies against: insulin (mouse monoclonal 1:300, #1061, Beta Cell Biology Consortium), vimentin (rabbit polyclonal 1:500, Santa Cruz), or α-SMA (mouse monoclonal, 1:1000, Dako, Inc).

We utilized Alexa-fluor 488 conjugated anti-mouse secondary antibody (1:500) (Invitrogen, Carlsbad, Calif.) for immunofluorescence labeling of insulin followed by visualization using a Nikon TE2000 inverted fluorescence microscope (Nikon, Inc).

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are herein described. All publications mentioned herein are hereby incorporated by reference in their entirety for the purpose of describing and disclosing the materials and methodologies that are reported in the publication which might be used in connection with the invention.

REFERENCES

1. Guariguata L, Whiting D, Weil C, Unwin N. The International Diabetes Federation diabetes atlas methodology for estimating global and national prevalence of diabetes in adults. Diabetes research and clinical practice 2011 December; 94(3):322-32.
2. Whiting D R, Guariguata L, Weil C, Shaw J. IDF diabetes atlas: global estimates of the prevalence of diabetes for 2011 and 2030. Diabetes research and clinical practice. [Research Support, Non-U.S. Gov't]. 2011 December; 94(3):311-21.
3. Huang E S, Basu A, O'Grady M, Capretta J C. Projecting the future diabetes population size and related costs for the U.S. Diabetes Care. [Research Support, N.I.H., Extramural Research Support, Non-U.S. Gov't]. 2009 December; 32(12):2225-9.
4. Oliver-Krasinski J M, Stoffers D A. On the origin of the beta cell. Genes & development. [Research Support, N.I.H., Extramural Review]. 2008 Aug. 1; 22(15):1998-2021.
5. Waldron-Lynch F, Herold K C Immunomodulatory therapy to preserve pancreatic beta-cell function in type 1 diabetes. Nature reviews Drug discovery. [Review]. 2011 June; 10(6):439-52.
6. Waldron-Lynch F, von Herrath M, Herold K C. Towards a curative therapy in type 1 diabetes: remission of autoimmunity, maintenance and augmentation of beta cell mass. Novartis Foundation symposium 2008; 292:146-55; discussion 55-8, 202-3.

7. Charbonnel B, Penfornis A, Varroud-Vial M, Kusnik-Joinville O, Detournay B. Insulin therapy for diabetes mellitus: Treatment regimens and associated costs. Diabetes & metabolism 2011 Dec. 13.
8. Soria B, Andreu E, Berná G, Fuentes E, Gil A, León-Quinto T, Martín F, Montanya E, Nadal A, Reig J A, Ripoll C, Roche E, Sanchez-Andrés J V, Segura J. Engineering pancreatic islets. Pflügers Archiv-European Journal of Physiology 2000; 440(1):1-18.
9. Zaret K S, Grompe M. Generation and regeneration of cells of the liver and pancreas. Science. [Research Support, N.I.H., Extramural Research Support, Non-U.S. Gov't Review]. 2008 Dec. 5; 322(5907):1490-4.
10. Weir G C, Cavelti-Weder C, Bonner-Weir S. Stem cell approaches for diabetes: towards beta cell replacement. Genome medicine 2011; 3 (9):61.
11. Sui J, Mehta M, Shi B, Morahan G, Jiang F X. Directed Differentiation of Embryonic Stem Cells Allows Exploration of Novel Transcription Factor Genes for Pancreas Development. Stem cell reviews 2012 Jan. 26; 1(1):1-10.
12. Ben-Yehudah A, White C, Navara C S, Castro C A, Ize-Ludlow D, Shaffer B, Sukhwani M, Mathews C E, Chaillet J R, Witchel S F. Evaluating protocols for embryonic stem cell differentiation into insulin-secreting beta-cells using insulin II-GFP as a specific and noninvasive reporter. Cloning Stem Cells 2009 June; 11(2):245-57.
13. Blyszczuk P, Czyz J, Kania G, Wagner M, Roll U, St-Onge L, Wobus A M. Expression of Pax4 in embryonic stem cells promotes differentiation of nestin-positive progenitor and insulin-producing cells. Proc Natl Acad Sci USA. [Research Support, Non-U.S. Gov't]. 2003 Feb. 4; 100(3):998-1003.
14. Borowiak M, Maehr R, Chen S, Chen A E, Tang W, Fox J L, Schreiber S L, Melton D A. Small molecules efficiently direct endodermal differentiation of mouse and human embryonic stem cells. Cell Stem Cell 2009 Apr. 3; 4(4):348-58.
15. D'Amour K A, Bang A G, Eliazer S, Kelly O G, Agulnick A D, Smart N G, Moorman M A, Kroon E, Carpenter M K, Baetge E E. Production of pancreatic hormone-expressing endocrine cells from human embryonic stem cells. Nat Biotechnol. [Research Support, Non-U.S. Gov't]. 2006 November; 24(11):1392-401.
16. Kroon E, Martinson L A, Kadoya K, Bang A G, Kelly O G, Eliazer S, Young H, Richardson M, Smart N G, Cunningham J, Agulnick A D, D'Amour K A, Carpenter M K, Baetge E E. Pancreatic endoderm derived from human embryonic stem cells generates glucose-responsive insulin-secreting cells in vivo. Nat Biotechnol 2008 April; 26(4):443-52.
17. Micallef S J, Janes M E, Knezevic K, Davis R P, Elefanty A G, Stanley E G. Retinoic acid induces Pdx1-positive endoderm in differentiating mouse embryonic stem cells. Diabetes 2005 February; 54(2):301-5.
18. Laursen K B, Wong P M, Gudas L J. Epigenetic regulation by RARalpha maintains ligand-independent transcriptional activity. Nucleic acids research 2012 January; 40(1):102-15.
19. Jaramillo M, Banerjee I. Endothelial cell co-culture mediates maturation of human embryonic stem cell to pancreatic insulin producing cells in a directed differentiation approach. J Vis Exp 2012(61).
20. Chen Y, Pan F C, Brandes N, Afelik S, Solter M, Pieler T. Retinoic acid signaling is essential for pancreas development and promotes endocrine at the expense of exocrine cell differentiation in Xenopus. Developmental biology. [Comparative Study Research Support, Non-U.S. Gov't]. 2004 Jul. 1; 271(1):144-60.
21. Ostrom M, Loffler K A, Edfalk S, Selander L, Dahl U, Ricordi C, Jeon J, Correa-Medina M, Diez J, Edlund H. Retinoic acid promotes the generation of pancreatic endocrine progenitor cells and their further differentiation into beta-cells. PLoS One. [Research Support, Non-U.S. Gov't]. 2008; 3(7):e2841.
22. Matthews K A, Rhoten W B, Driscoll H K, Chertow B S. Vitamin A deficiency impairs fetal islet development and causes subsequent glucose intolerance in adult rats. The Journal of nutrition. [Research Support, U.S. Gov't, P.H.S.]. 2004 August; 134(8):1958-63.
23. Chertow B S, Blaner W S, Baranetsky N G, Sivitz W I, Cordle M B, Thompson D, Meda P. Effects of vitamin A deficiency and repletion on rat insulin secretion in vivo and in vitro from isolated islets. J Clin Invest. [In Vitro Research Support, Non-U.S. Gov't Research Support, U.S. Gov't, P.H.S.]. 1987 January; 79(1):163-9.
24. Dodge R, Loomans C, Sharma A, Bonner-Weir S. Developmental pathways during in vitro progression of human islet neogenesis. Differentiation. [Research Support, N.I.H., Extramural Research Support, Non-U.S. Gov't]. 2009 February; 77(2):135-47.
25. Dolle P, Ruberte E, Leroy P, Morriss-Kay G, Chambon P. Retinoic acid receptors and cellular retinoid binding proteins. I. A systematic study of their differential pattern of transcription during mouse organogenesis. Development. [Research Support, Non-U.S. Gov't]. 1990 December; 110(4):1133-51.
26. Ghyselinck N B, Dupe V, Dierich A, Messaddeq N, Gamier J M, Rochette-Egly C, Chambon P, Mark M. Role of the retinoic acid receptor beta (RARβ) during mouse development. The International journal of developmental biology. [Research Support, Non-U.S. Gov't Research Support, U.S. Gov't, P.H.S.]. 1997 June; 41(3):425-47.
27. Martinez-Ceballos E, Gudas L J. Hoxa1 is required for the retinoic acid-induced differentiation of embryonic stem cells into neurons. Journal of neuroscience research. [Research Support, N.I.H., Extramural]. 2008 October; 86(13):2809-19.
28. Martinez-Ceballos E, Chambon P, Gudas L J. Differences in gene expression between wild type and Hoxa1 knockout embryonic stem cells after retinoic acid treatment or leukemia inhibitory factor (LIF) removal. The Journal of biological chemistry. [Research Support, N.I.H., Extramural Research Support, U.S. Gov't, P.H.S.]. 2005 Apr. 22; 280(16):16484-98.
29. Benoit Y D, Lussier C, Ducharme P A, Sivret S, Schnapp L M, Basora N, Beaulieu J F. Integrin alpha8beta1 regulates adhesion, migration and proliferation of human intestinal crypt cells via a predominant RhoA/ROCK-dependent mechanism. Biology of the cell/under the auspices of the European Cell Biology Organization. [Research Support, Non-U.S. Gov't]. 2009 December; 101(12):695-708.
30. Benoit Y D, Pare F, Francoeur C, Jean D, Tremblay E, Boudreau F, Escaffit F, Beaulieu J F. Cooperation between HNF-1alpha, Cdx2, and GATA-4 in initiating an enterocytic differentiation program in a normal human intestinal epithelial progenitor cell line. American journal of physiology Gastrointestinal and liver physiology. [Research Support, Non-U.S. Gov't]. 2010 April; 298(4):G504-17.
31. Auclair B A, Benoit Y D, Rivard N, Mishina Y, Perreault N. Bone morphogenetic protein signaling is essential for terminal differentiation of the intestinal secretory cell lineage. Gastroenterology 2007 September; 133(3):887-96.
32. Yoshino J, Mills K F, Yoon M J, Imai S. Nicotinamide mononucleotide, a key NAD(+) intermediate, treats the pathophysiology of diet- and age-induced diabetes in mice. Cell Metab 2011 Oct. 5; 14(4):528-36.
33. Spokoini R, Kfir-Erenfeld S, Yefenof E, Sionov R V. Glycogen synthase kinase-3 plays a central role in mediating glucocorticoid-induced apoptosis. Mol Endocrinol 2010 June; 24(6):1136-50.
34. Yamaguchi T P, Takada S, Yoshikawa Y, Wu N, McMahon A P. T (Brachyury) is a direct target of Wnt3a during paraxial mesoderm specification. Genes & development 1999 Dec. 15; 13(24):3185-90.
35. Otonkoski T, Beattie G M, Mally M I, Ricordi C, Hayek A. Nicotinamide is a potent inducer of endocrine differentiation in cultured human fetal pancreatic cells. J Clin Invest 1993 September; 92(3):1459-66.
36. Lumelsky N, Blondel O, Laeng P, Velasco I, Ravin R, McKay R. Differentiation of embryonic stem cells to insulin-secreting structures similar to pancreatic islets. Science. [Research Support, Non-U.S. Gov't]. 2001 May 18; 292(5520):1389-94.
37. Marchand M, Schroeder I S, Markossian S, Skoudy A, Negre D, Cosset F L, Real P, Kaiser C, Wobus A M, Savatier P. Mouse ES cells over-expressing the transcription factor NeuroD1 show increased differentiation towards endocrine lineages and insulin-expressing cells. The International journal of developmental biology. [Research Support, Non-U.S. Gov't]. 2009; 53(4):569-78.
38. Langton S, Gudas L J. CYP26A1 knockout embryonic stem cells exhibit reduced differentiation and growth arrest in response to retinoic acid. Developmental biology. [Research Support, N.I.H., Extramural Research Support, U.S. Gov't, Non-P.H.S.]. 2008 Mar. 15; 315(2):331-54.
39. Soria B. In-vitro differentiation of pancreatic beta-cells. Differentiation 2001 October; 68(4-5):205-19.
40. Van Hoof D, D'Amour K A, German M S. Derivation of insulin-producing cells from human embryonic stem cells. Stem cell research. [Research Support, Non-U.S. Gov't Review]. 2009 September-November; 3(2-3):73-87.
41. Bernardo A S, Hay C W, Docherty K. Pancreatic transcription factors and their role in the birth, life and survival of the pancreatic beta cell. Mol Cell Endocrinol 2008 Nov. 6; 294(1-2):1-9.
42. Kashyap V, Rezende N C, Scotland K B, Shaffer S M, Persson J L, Gudas L J, Mongan N P. Regulation of stem cell pluripotency and differentiation involves a mutual regulatory circuit of the NANOG, OCT4, and SOX2 pluripotency transcription factors with polycomb repressive complexes and stem cell microRNAs. Stem cells and development 2009 September; 18(7):1093-108.
43. Rukstalis J M, Habener J F. Neurogenin3: a master regulator of pancreatic islet differentiation and regeneration. Islets 2009 November-December; 1(3):177-84.
44. Gosmain Y, Katz L S, Masson M H, Cheyssac C, Poisson C, Philippe J. Pax6 is crucial for beta-cell function, insulin biosynthesis, and glucose-induced insulin secretion. Mol Endocrinol. [Research Support, Non-U.S. Gov't]. 2012 April; 26(4):696-709.
45. Ahlgren U, Pfaff S L, Jessell T M, Edlund T, Edlund H. Independent requirement for ISL1 in formation of pancreatic mesenchyme and islet cells. Nature. [Research Support, Non-U.S. Gov't]. 1997 Jan. 16; 385(6613):257-60.
46. Naujok O, Francini F, Picton S, Bailey C J, Lenzen S, Jorns A. Changes in gene expression and morphology of mouse embryonic stem cells on differentiation into insulin-producing cells in vitro and in vivo. Diabetes Metab Res Rev 2009 July; 25(5):464-76.
47. Gasa R, Mrejen C, Leachman N, Otten M, Barnes M, Wang J, Chakrabarti S, Mirmira R, German M. Proendocrine genes coordinate the pancreatic islet differentiation program in vitro. Proc Natl Acad Sci USA 2004 Sep. 7; 101(36):13245-50.
48. Steiner D F, Cunningham D, Spigelman L, Aten B. Insulin biosynthesis: evidence for a precursor. Science 1967 Aug. 11; 157(3789):697-700.
49. Daly M E, Vale C, Walker M, Littlefield A, Alberti K G, Mathers J C. Acute effects on insulin sensitivity and diurnal metabolic profiles of a high-sucrose compared with a high-starch diet. Am J Clin Nutr 1998 June; 67(6):1186-96.
50. Cryer P E, Axelrod L, Grossman A B, Heller S R, Montori V M, Seaquist E R, Service F J. Evaluation and management of adult hypoglycemic disorders: an Endocrine Society Clinical Practice Guideline. The Journal of clinical endocrinology and metabolism 2009 March; 94(3):709-28.
51. Cai J, Yu C, Liu Y, Chen S, Guo Y, Yong J, Lu W, Ding M, Deng H. Generation of homogeneous PDX1(+) pancreatic progenitors from human ES cell-derived endoderm cells. J Mol Cell Biol. [Research Support, Non-U.S. Gov't]. 2010 February; 2(1):50-60.
52. Jonsson J, Carlsson L, Edlund T, Edlund H. Insulin-promoter-factor 1 is required for pancreas development in mice. Nature 1994 Oct. 13; 371(6498):606-9.
53. Fujimoto K, Polonsky K S. Pdx1 and other factors that regulate pancreatic beta-cell survival. Diabetes, obesity & metabolism 2009 November; 11 Suppl 4:30-7.
54. Dalgin G, Ward A B, Hao le T, Beattie C E, Nechiporuk A, Prince V E. Zebrafish mnx1 controls cell fate choice in the developing endocrine pancreas. Development 2011 November; 138(21):4597-608.
55. Vetere A, Marsich E, Di Piazza M, Koncan R, Micali F, Paoletti S. Neurogenin3 triggers beta-cell differentiation of retinoic acid-derived endoderm cells. The Biochemical journal 2003 May 1; 371(Pt 3):831-41.
56. Dohrmann C, Gruss P, Lemaire L. Pax genes and the differentiation of hormone producing endocrine cells in the pancreas. Mech Dev 2000 Mar. 15; 92(1):47-54.
57. American Diabetes A. Diagnosis and classification of diabetes mellitus. Diabetes Care 2005 January; 28 Suppl 1:S37-42.
58. Del Prato S, Marchetti P. Beta- and alpha-cell dysfunction in type 2 diabetes. Horm Metab Res 2004 November-December; 36(11-12):775-81.
59. Riserus U, Willett W C, Hu F B. Dietary fats and prevention of type 2 diabetes. Prog Lipid Res 2009 January; 48(1):44-51.
60. Sirchia S M, Ren M, Pili R, Sironi E, Somenzi G, Ghidoni R, Toma S, Nicolo G, Sacchi N. Endogenous reactivation of the RARβ2 tumor suppressor gene epigenetically silenced in breast cancer. Cancer research 2002 May 1; 62(9):2455-61.
61. Youssef E M, Estecio M R, Issa J P. Methylation and regulation of expression of different retinoic acid receptor beta isoforms in human colon cancer. Cancer Biol Ther 2004 January; 3(1):82-6.
62. House M G, Herman J G, Guo M Z, Hooker C M, Schulick R D, Lillemoe K D, Cameron J L, Hruban R H, Maitra A, Yeo C J. Aberrant hypermethylation of tumor suppressor genes in pancreatic endocrine neoplasms. Ann Surg 2003 September; 238(3):423-31; discussion 31-2.
63. Sato N, Fukushima N, Hruban R H, Goggins M. CpG island methylation profile of pancreatic intraepithelial neoplasia. Mod Pathol 2008 March; 21(3):238-44.
64. Volkmar M, Dedeurwaerder S, Cunha D A, Ndlovu M N, Defiance M, Deplus R, Calonne E, Volkmar U, Igoillo-Esteve M, Naamane N, Del Guerra S, Masini M, Bugliani M, Marchetti P, Cnop M, Eizirik D L, Fuks F. DNA methylation profiling identifies epigenetic dysregulation in pancreatic islets from type 2 diabetic patients. EMBO J 2012 Mar. 21; 31(6):1405-26.
65. Lund, B. W.; Piu, F.; Gauthier, N. K.; Eeg, A.; Currier, E.; Sherbukhin, V.; Brann, M. R.; Hacksell, U.; Olsson, R. Discovery of a Potent, Orally Available, and Isoform-Selective Retinoic Acid beta2 Receptor Agonist. J. Med. Chem. 2005, 48, 7517-7519.
66. Vivat-Hannah V et al, Synergistic Cytotoxicity Exhibited by Combination Treatment of Selective Retinoid Ligands with Taxol (Paclitaxel). Cancer Res. 2001, 61, 8703-8711.
67. Millikan L E, Adapalene: an update on newer comparative studies between the various retinoids. Int. J. Dermatol. 2000, 39, 784-88.
68. Chen J Y et al (1995) RAR-specific agonist/antagonists which dissociate transactivation and AP1 transrepression inhibit anchorage-independent cell proliferation. EMBO J. 1995, 14, 1187-97.
69. Lazo M, Hernaez R, Eberhardt M S, Bonekamp S, Kamel I, Guallar E, Koteish A, Brancati F L, Clark J M. Prevalence of nonalcoholic fatty liver disease in the United States: the Third National Health and Nutrition Examination Survey, 1988-1994. Am J Epidemiol. 2013; 1:38-45.
70. Loomba R, Sanyal A J. The global NAFLD epidemic. Nat Rev Gastroenterol Hepatol. 2013; 11:686-90.
71. Baffy G, Brunt E M, Caldwell S H. Hepatocellular carcinoma in non-alcoholic fatty liver disease: an emerging menace. J Hepatol. 2012; 6:1384-91.
72. Reeves H L, Friedman S L. Activation of hepatic stellate cells—a key issue in liver fibrosis. Front Biosci. 2002; 7:808-26
73. Puche J E, Saiman Y, Friedman S L. Hepatic stellate cells and liver fibrosis. Compr Physiol. 2013; 4):1473-92.
74. Geerts, A. History, heterogeneity, developmental biology, and functions of quiescent hepatic stellate cells. Semin. Liver Dis. 2001; 21:311-335
75. Brun P J, Yang K J, Lee S A, Yuen J J, Blaner W S. Retinoids: Potent regulators of metabolism. Biofactors. 2013 2):151-63.
76. (CDC) CfDCaP. Vital signs: prevalence, treatment, and control of high levels of low-density lipoprotein cholesterol—United States, 1999-2002 and 2005-200. MMWR Morb Mortal Wkly Rep. 2011; 60(4):109-14. PubMed PMID:21293326.
77. Martin S S, Abd T T, Jones S R, Michos E D, Blumenthal R S, Blaha M J. 2013 American Cholesterol Treatment Guideline: What Was Done Well and What Could Be Done Better. J Am Coll Cardiol. 2014. doi: 10.1016/j.jacc.2014.02.578. PubMed PMID: 24681146.
78. Mampuya W M, Frid D, Rocco M, Huang J, Brennan D M, Hazen S L, Cho L. Treatment strategies in patients with statin intolerance: the Cleveland Clinic experience. Am Heart J. 2013; 166(3):597-603. doi: 10.1016/j.ahj.2013.06.004. PubMed PMID: 24016512.
79. Brun P J, Yang K J, Lee S A, Yuen J J, Blaner W S. Retinoids: Potent regulators of metabolism. Biofactors. 2013; 39(2):151-63. doi: 10.1002/biof.1056. PubMed PMID: 23281051; PubMed Central PMCID: PMCPMC3620893.
80. Tang X H, Gudas L J. Retinoids, retinoic acid receptors, and cancer. Annu Rev Pathol. 2011; 6:345-64. doi: 10.1146/annurev-pathol-011110-130303. PubMed PMID: 21073338.
81. Baldwin H E, Nighland M, Kendall C, Mays D A, Grossman R, Newburger J. 40 years of topical tretinoin use in review. J Drugs Dermatol. 2013; 12(6):638-42. PubMed PMID: 23839179.
82. Ellis C N, Swanson N A, Grekin R C, Goldstein N G, Bassett D R, Anderson T F, Voorhees J J. Etretinate therapy causes increases in lipid levels in patients with psoriasis. Arch Dermatol. 1982; 118(8):559-62. PubMed PMID: 7103524.
83. Lyons F, Laker M F, Marsden J R, Manuel R, Shuster S. Effect of oral 13-cis-retinoic acid on serum lipids. Br J Dermatol. 1982; 107(5):591-5. PubMed PMID: 6215057.
84. Marsden J. Hyperlipidaemia due to isotretinoin and etretinate: possible mechanisms and consequences. Br J Dermatol. 1986; 114(4):401-7. PubMed PMID: 3516195.
85. Barth J H, Macdonald-Hull S P, Mark J, Jones R G, Cunliffe W J. Isotretinoin therapy for acne vulgaris: a re-evaluation of the need for measurements of plasma lipids and liver function tests. Br J Dermatol. 1993; 129(6):704-7. PubMed PMID: 8286255.
86. Amengual J, Ribot J, Bonet M L, Palou A. Retinoic acid treatment enhances lipid oxidation and inhibits lipid biosynthesis capacities in the liver of mice. Cell Physiol Biochem. 2010; 25(6):657-66. doi: 10.1159/000315085. PubMed PMID: 20511711.
87. Kim S C, Kim C K, Axe D, Cook A, Lee M, Li T, Smallwood N, Chiang J Y, Hardwick J P, Moore D D, Lee Y K. All-trans-retinoic acid ameliorates hepatic steatosis in mice by a novel transcriptional cascade. Hepatology. 2013. doi: 10.1002/hep.26699. PubMed PMID: 24038081.
88. Lund B W, Piu F, Gauthier N K, Eeg A, Currier E, Sherbukhin V, Brann M R, Hacksell U, Olsson R. Discovery of a potent, orally available, and isoform-selective retinoic acid beta2 receptor agonist. J Med Chem. 2005; 48(24):7517-9. doi: 10.1021/jm050891r. PubMed PMID: 16302793.
89. Thacher S M, Vasudevan J, Chandraratna R A. Therapeutic applications for ligands of retinoid receptors. Curr Pharm Des. 2000; 6(1):25-58. PubMed PMID: 10637371.
90. Laursen K B, Mongan N P, Zhuang Y, Ng M M, Benoit Y D, Gudas L J. Polycomb recruitment attenuates retinoic acid-induced transcription of the bivalent NR2F1 gene. Nucleic Acids Res. 2013; 41(13):6430-43. doi: 10.1093/nar/gkt367. PubMed PMID: 23666625.
91. Buchovercky C M, Turley S D, Brown H M, Kyle S M, McDonald J G, Liu B, Pieper A A, Huang W, Katz D B, Russell D W, Shendure J, Justice M Y. A suppressor screen in Mecp2 mutant mice implicates cholesterol metabolism in Rett syndrome. Nature Genetics. September; 45(9):1013-20; Epub 2013 Jul. 28.
92. Justice, M J, Public Research Seminar (A genetic suppressor screen in mice reveals that lipid metabolism is a therapeutic target for Rett Syndrome) at Sloan Kettering Institute, May 1, 2014.

What is claimed is:

1. A method of lowering cholesterol and/or triglyceride levels in a subject in need thereof, comprising administering to said subject a pharmaceutical composition comprising a therapeutically effective amount of a retinoic acid receptor-beta (RARβ) agonist, wherein said RARβ agonist is a highly isoform-selective RARβ2 agonist selected from a compound set forth in Formula I,

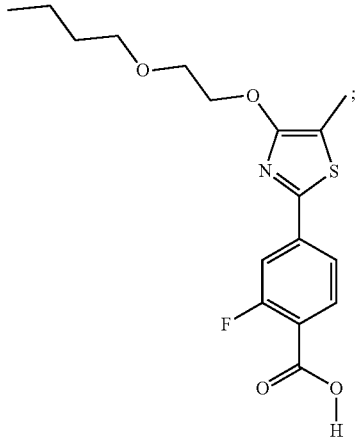

Formula I a compound set forth in Formula II,

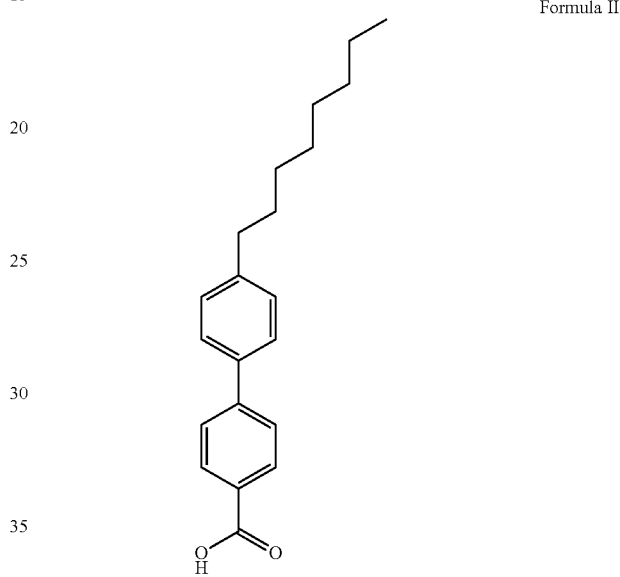

Formula II or a pharmaceutically acceptable salt thereof, and wherein said pharmaceutical composition further comprising a pharmaceutically acceptable carrier, thereby lowering said cholesterol and/or said triglyceride level in said subject.

2. The method according to claim 1, the subject in need thereof has a disease selected from the group consisting of a pancreatic disease, a cardiovascular disease, a liver disease, a kidney disease, obesity, fibrosis, hyperlipidemia, hypertriglyceridemia, hyperglycemia, or an organ-specific vitamin A deficiency.

3. The method of claim 2, wherein said pancreatic disease is diabetes.

4. The method of claim 2, wherein said liver disease is fatty liver disease (FLD), non-alcoholic steatohepatitis (NASH), liver fibrosis, or hepatic steatosis.

5. The method of claim 2, wherein said kidney disease is diabetic nephropathy.

6. The method of claim 2, wherein said disease is associated with a high fat diet.

7. The method of claim 2, wherein the pancreatic disease is Type II diabetes.

* * * * *

SEQUENCE LISTING

<160> NUMBER OF SEQ ID NOS: 106

<210> SEQ ID NO 1
<211> LENGTH: 22
<212> TYPE: DNA
<213> ORGANISM: Artificial Sequence
<220> FEATURE:
<223> OTHER INFORMATION: mIns1 primer

<400> SEQUENCE: 1
tagtgaccag ctataatcag ag                                              22

<210> SEQ ID NO 2
<211> LENGTH: 20
<212> TYPE: DNA
<213> ORGANISM: Artificial Sequence
<220> FEATURE:
<223> OTHER INFORMATION: mIns1 primer

<400> SEQUENCE: 2
acgccaaggt ctgaaggtcc                                                 20

<210> SEQ ID NO 3
<211> LENGTH: 19
<212> TYPE: DNA
<213> ORGANISM: Artificial Sequence
<220> FEATURE:
<223> OTHER INFORMATION: mGcg primer

<400> SEQUENCE: 3
ccgccgtgcc caagattt                                                   19

<210> SEQ ID NO 4
<211> LENGTH: 17
<212> TYPE: DNA
<213> ORGANISM: Artificial Sequence
<220> FEATURE:
<223> OTHER INFORMATION: mGcg primer

<400> SEQUENCE: 4
cctgcggccg agttcct                                                    17

<210> SEQ ID NO 5
<211> LENGTH: 20
<212> TYPE: DNA
<213> ORGANISM: Artificial Sequence
<220> FEATURE:
<223> OTHER INFORMATION: mSst* primer

<400> SEQUENCE: 5
gagcccaacc agacagagaa                                                 20

<210> SEQ ID NO 6
<211> LENGTH: 20
<212> TYPE: DNA
<213> ORGANISM: Artificial Sequence
<220> FEATURE:
<223> OTHER INFORMATION: mSst* primer

<400> SEQUENCE: 6
gaagttcttg cagccagctt                                                 20

<210> SEQ ID NO 7
<211> LENGTH: 24
<212> TYPE: DNA
<213> ORGANISM: Artificial Sequence
<220> FEATURE:
<223> OTHER INFORMATION: mNgn3* primer

<400> SEQUENCE: 7
ctgcgcatag cggaccacag cttc    24

<210> SEQ ID NO 8
<211> LENGTH: 26
<212> TYPE: DNA
<213> ORGANISM: Artificial Sequence
<220> FEATURE:
<223> OTHER INFORMATION: mNgn3* primer

<400> SEQUENCE: 8
cttcacaaga agtctgagaa caccag    26

<210> SEQ ID NO 9
<211> LENGTH: 20
<212> TYPE: DNA
<213> ORGANISM: Artificial Sequence
<220> FEATURE:
<223> OTHER INFORMATION: mRAR primer

<400> SEQUENCE: 9
gatcctggat ttctacaccg    20

<210> SEQ ID NO 10
<211> LENGTH: 19
<212> TYPE: DNA
<213> ORGANISM: Artificial Sequence
<220> FEATURE:
<223> OTHER INFORMATION: mRAR primer

<400> SEQUENCE: 10
cactgacgcc atagtggta    19

<210> SEQ ID NO 11
<211> LENGTH: 23
<212> TYPE: DNA
<213> ORGANISM: Artificial Sequence
<220> FEATURE:
<223> OTHER INFORMATION: mNanog primer

<400> SEQUENCE: 11
aaaggatgaa gtgcaagcgg tgg    23

<210> SEQ ID NO 12
<211> LENGTH: 21
<212> TYPE: DNA
<213> ORGANISM: Artificial Sequence
<220> FEATURE:
<223> OTHER INFORMATION: mNanog primer

<400> SEQUENCE: 12
ctggctttgc cctgacttta a    21

<210> SEQ ID NO 13
<211> LENGTH: 24
<212> TYPE: DNA
<213> ORGANISM: Artificial Sequence
<220> FEATURE:
<223> OTHER INFORMATION: mRex1 primer

<400> SEQUENCE: 13
gaaagcagga tcgcctcact gtgc    24

```
<210> SEQ ID NO 14
<211> LENGTH: 23
<212> TYPE: DNA
<213> ORGANISM: Artificial Sequence
<220> FEATURE:
<223> OTHER INFORMATION: mRex1 primer

<400> SEQUENCE: 14
cgataagaca ccacagtaca cac                                                 23

<210> SEQ ID NO 15
<211> LENGTH: 24
<212> TYPE: DNA
<213> ORGANISM: Artificial Sequence
<220> FEATURE:
<223> OTHER INFORMATION: mCyp26a1 primer

<400> SEQUENCE: 15
gaaacattgc agatggtgct tcag                                                24

<210> SEQ ID NO 16
<211> LENGTH: 23
<212> TYPE: DNA
<213> ORGANISM: Artificial Sequence
<220> FEATURE:
<223> OTHER INFORMATION: mCyp26a1 primer

<400> SEQUENCE: 16
cggctgaagg cctgcataat cac                                                 23

<210> SEQ ID NO 17
<211> LENGTH: 23
<212> TYPE: DNA
<213> ORGANISM: Artificial Sequence
<220> FEATURE:
<223> OTHER INFORMATION: mPax-6 primer

<400> SEQUENCE: 17
gcaaccccca gtccccagtc aga                                                 23

<210> SEQ ID NO 18
<211> LENGTH: 24
<212> TYPE: DNA
<213> ORGANISM: Artificial Sequence
<220> FEATURE:
<223> OTHER INFORMATION: mPax-6 primer

<400> SEQUENCE: 18
agtccattcc cgggctccag ttca                                                24

<210> SEQ ID NO 19
<211> LENGTH: 18
<212> TYPE: DNA
<213> ORGANISM: Artificial Sequence
<220> FEATURE:
<223> OTHER INFORMATION: mIsl-1* primer

<400> SEQUENCE: 19
cccgggggcc actatttg                                                       18

<210> SEQ ID NO 20
<211> LENGTH: 17
<212> TYPE: DNA
<213> ORGANISM: Artificial Sequence
<220> FEATURE:
<223> OTHER INFORMATION: mIsl-1* primer
```

<400> SEQUENCE: 20
cgggcacgca tcacgaa                                                17

<210> SEQ ID NO 21
<211> LENGTH: 20
<212> TYPE: DNA
<213> ORGANISM: Artificial Sequence
<220> FEATURE:
<223> OTHER INFORMATION: mIapp* primer

<400> SEQUENCE: 21
tgggctgtag ttcctgaagc                                             20

<210> SEQ ID NO 22
<211> LENGTH: 20
<212> TYPE: DNA
<213> ORGANISM: Artificial Sequence
<220> FEATURE:
<223> OTHER INFORMATION: mIapp* primer

<400> SEQUENCE: 22
gcacttccgt ttgtccatct                                             20

<210> SEQ ID NO 23
<211> LENGTH: 20
<212> TYPE: DNA
<213> ORGANISM: Artificial Sequence
<220> FEATURE:
<223> OTHER INFORMATION: HPRT1 primer

<400> SEQUENCE: 23
tgctcgagat gtgatgaagg                                             20

<210> SEQ ID NO 24
<211> LENGTH: 20
<212> TYPE: DNA
<213> ORGANISM: Artificial Sequence
<220> FEATURE:
<223> OTHER INFORMATION: HPRT1 primer

<400> SEQUENCE: 24
tcccctgttg actggtcatt                                             20

<210> SEQ ID NO 25
<211> LENGTH: 20
<212> TYPE: DNA
<213> ORGANISM: Artificial Sequence
<220> FEATURE:
<223> OTHER INFORMATION: RAR-beta-2 primer

<400> SEQUENCE: 25
tggcattgtt tgcacgctga                                             20

<210> SEQ ID NO 26
<211> LENGTH: 22
<212> TYPE: DNA
<213> ORGANISM: Artificial Sequence
<220> FEATURE:
<223> OTHER INFORMATION: RAR-beta-2 primer

<400> SEQUENCE: 26
cccccctttg gcaaagaata ga                                          22

<210> SEQ ID NO 27

```
<211> LENGTH: 23
<212> TYPE: DNA
<213> ORGANISM: Artificial Sequence
<220> FEATURE:
<223> OTHER INFORMATION: CYP26A1 RAR-beta-2 primer

<400> SEQUENCE: 27
ctttataagg ccgcccaggt tac                                            23

<210> SEQ ID NO 28
<211> LENGTH: 22
<212> TYPE: DNA
<213> ORGANISM: Artificial Sequence
<220> FEATURE:
<223> OTHER INFORMATION: CYP26A1 RAR-beta-2 primer

<400> SEQUENCE: 28
cccgatccgc aattaaagat ga                                             22

<210> SEQ ID NO 29
<211> LENGTH: 21
<212> TYPE: DNA
<213> ORGANISM: Artificial Sequence
<220> FEATURE:
<223> OTHER INFORMATION: LRAT primer

<400> SEQUENCE: 29
tctggcatct ctcctacgct g                                              21

<210> SEQ ID NO 30
<211> LENGTH: 24
<212> TYPE: DNA
<213> ORGANISM: Artificial Sequence
<220> FEATURE:
<223> OTHER INFORMATION: LRAT primer

<400> SEQUENCE: 30
gttccaagtc cttcagtctc ttgc                                           24

<210> SEQ ID NO 31
<211> LENGTH: 22
<212> TYPE: DNA
<213> ORGANISM: Artificial Sequence
<220> FEATURE:
<223> OTHER INFORMATION: INS2 primer

<400> SEQUENCE: 31
tgtggggagc gtggcttctt ct                                             22

<210> SEQ ID NO 32
<211> LENGTH: 22
<212> TYPE: DNA
<213> ORGANISM: Artificial Sequence
<220> FEATURE:
<223> OTHER INFORMATION: INS2 primer

<400> SEQUENCE: 32
cagctccagt tgtgccactt gt                                             22

<210> SEQ ID NO 33
<211> LENGTH: 19
<212> TYPE: DNA
<213> ORGANISM: Artificial Sequence
<220> FEATURE:
<223> OTHER INFORMATION: HPRT primer

<400> SEQUENCE: 33
```

-continued

| | |
|---|---|
| tgctcgagtg tgatgaagg | 19 |

<210> SEQ ID NO 34
<211> LENGTH: 19
<212> TYPE: DNA
<213> ORGANISM: Artificial Sequence
<220> FEATURE:
<223> OTHER INFORMATION: HPRT primer

<400> SEQUENCE: 34

| | |
|---|---|
| tccctgttga ctggtcatt | 19 |

<210> SEQ ID NO 35
<211> LENGTH: 19
<212> TYPE: DNA
<213> ORGANISM: Artificial Sequence
<220> FEATURE:
<223> OTHER INFORMATION: TNF-alpha primer

<400> SEQUENCE: 35

| | |
|---|---|
| cctgtagccc acgtcgtag | 19 |

<210> SEQ ID NO 36
<211> LENGTH: 22
<212> TYPE: DNA
<213> ORGANISM: Artificial Sequence
<220> FEATURE:
<223> OTHER INFORMATION: TNF-alpha primer

<400> SEQUENCE: 36

| | |
|---|---|
| gggagtagac aaggtacaac cc | 22 |

<210> SEQ ID NO 37
<211> LENGTH: 23
<212> TYPE: DNA
<213> ORGANISM: Artificial Sequence
<220> FEATURE:
<223> OTHER INFORMATION: MCP1 primer

<400> SEQUENCE: 37

| | |
|---|---|
| ttaaaaacct ggatcggaac caa | 23 |

<210> SEQ ID NO 38
<211> LENGTH: 23
<212> TYPE: DNA
<213> ORGANISM: Artificial Sequence
<220> FEATURE:
<223> OTHER INFORMATION: MCP1 primer

<400> SEQUENCE: 38

| | |
|---|---|
| gcattagctt cagatttacg ggt | 23 |

<210> SEQ ID NO 39
<211> LENGTH: 21
<212> TYPE: DNA
<213> ORGANISM: artificial sequences
<220> FEATURE:
<223> OTHER INFORMATION: Primers

<400> SEQUENCE: 39

| | |
|---|---|
| caaggccatc gactacatcc g | 21 |

<210> SEQ ID NO 40
<211> LENGTH: 19
<212> TYPE: DNA

```
<213> ORGANISM: artificial sequences
<220> FEATURE:
<223> OTHER INFORMATION: Primer

<400> SEQUENCE: 40
caccacttcg ggtttcatg                                                19

<210> SEQ ID NO 41
<211> LENGTH: 19
<212> TYPE: DNA
<213> ORGANISM: artificial sequences
<220> FEATURE:
<223> OTHER INFORMATION: Primer

<400> SEQUENCE: 41
ccgccgtgcc caagatttt                                                19

<210> SEQ ID NO 42
<211> LENGTH: 21
<212> TYPE: DNA
<213> ORGANISM: artificial sequences
<220> FEATURE:
<223> OTHER INFORMATION: primers

<400> SEQUENCE: 42
tgggtaatcc atagagccca g                                             21

<210> SEQ ID NO 43
<211> LENGTH: 20
<212> TYPE: DNA
<213> ORGANISM: artificial sequences
<220> FEATURE:
<223> OTHER INFORMATION: primers

<400> SEQUENCE: 43
atgatggctc aggtcccact                                               20

<210> SEQ ID NO 44
<211> LENGTH: 20
<212> TYPE: DNA
<213> ORGANISM: artificial sequences
<220> FEATURE:
<223> OTHER INFORMATION: primers

<400> SEQUENCE: 44
cactggggca tcgtagttga                                               20

<210> SEQ ID NO 45
<211> LENGTH: 20
<212> TYPE: DNA
<213> ORGANISM: artificial sequences
<220> FEATURE:
<223> OTHER INFORMATION: primers

<400> SEQUENCE: 45
tctcctgtgg gattcctgac                                               20

<210> SEQ ID NO 46
<211> LENGTH: 20
<212> TYPE: DNA
<213> ORGANISM: artificial sequences
<220> FEATURE:
<223> OTHER INFORMATION: primers

<400> SEQUENCE: 46
ctccacgaac agcttcacaa                                               20
```

<210> SEQ ID NO 47
<211> LENGTH: 20
<212> TYPE: DNA
<213> ORGANISM: artificial sequences
<220> FEATURE:
<223> OTHER INFORMATION: primers

<400> SEQUENCE: 47
agagccccat ctgtcctctc                                          20

<210> SEQ ID NO 48
<211> LENGTH: 22
<212> TYPE: DNA
<213> ORGANISM: artificial sequences
<220> FEATURE:
<223> OTHER INFORMATION: primers

<400> SEQUENCE: 48
actggtagtc tgcaaaacca aa                                       22

<210> SEQ ID NO 49
<211> LENGTH: 22
<212> TYPE: DNA
<213> ORGANISM: artificial sequences
<220> FEATURE:
<223> OTHER INFORMATION: primers

<400> SEQUENCE: 49
ctccaagaat accaaagtgc ga                                       22

<210> SEQ ID NO 50
<211> LENGTH: 21
<212> TYPE: DNA
<213> ORGANISM: artificial sequences
<220> FEATURE:
<223> OTHER INFORMATION: primers

<400> SEQUENCE: 50
gcctgatgct ttatccccac a                                        21

<210> SEQ ID NO 51
<211> LENGTH: 19
<212> TYPE: DNA
<213> ORGANISM: artificial sequences
<220> FEATURE:
<223> OTHER INFORMATION: primers

<400> SEQUENCE: 51
gcagcaacgg gaccattct                                           19

<210> SEQ ID NO 52
<211> LENGTH: 23
<212> TYPE: DNA
<213> ORGANISM: artificial sequences
<220> FEATURE:
<223> OTHER INFORMATION: primers

<400> SEQUENCE: 52
ccccatgact aagtccttca act                                      23

<210> SEQ ID NO 53
<211> LENGTH: 21
<212> TYPE: DNA
<213> ORGANISM: artificial sequences
<220> FEATURE:

```
<223> OTHER INFORMATION: primers

<400> SEQUENCE: 53
agcttgcccg aattgtatgt g                                    21

<210> SEQ ID NO 54
<211> LENGTH: 23
<212> TYPE: DNA
<213> ORGANISM: artificial sequences
<220> FEATURE:
<223> OTHER INFORMATION: primers

<400> SEQUENCE: 54
tctgttgtga accatgtgac ttc                                  23

<210> SEQ ID NO 55
<211> LENGTH: 20
<212> TYPE: DNA
<213> ORGANISM: artificial sequences
<220> FEATURE:
<223> OTHER INFORMATION: primers

<400> SEQUENCE: 55
tgcccaaggc aacttaaggg                                      20

<210> SEQ ID NO 56
<211> LENGTH: 20
<212> TYPE: DNA
<213> ORGANISM: artificial sequences
<220> FEATURE:
<223> OTHER INFORMATION: primers

<400> SEQUENCE: 56
cagtaaacac ccccatcgct                                      20

<210> SEQ ID NO 57
<211> LENGTH: 23
<212> TYPE: DNA
<213> ORGANISM: artificial sequences
<220> FEATURE:
<223> OTHER INFORMATION: primers

<400> SEQUENCE: 57
gtgtcaaagc ctctaggttt ctt                                  23

<210> SEQ ID NO 58
<211> LENGTH: 22
<212> TYPE: DNA
<213> ORGANISM: artificial sequences
<220> FEATURE:
<223> OTHER INFORMATION: primers

<400> SEQUENCE: 58
ggtacacatt gtaaccgtcc tc                                   22

<210> SEQ ID NO 59
<211> LENGTH: 19
<212> TYPE: DNA
<213> ORGANISM: artificial sequences
<220> FEATURE:
<223> OTHER INFORMATION: primers

<400> SEQUENCE: 59
tgctcgagtg tgatgaagg                                       19
```

```
<210> SEQ ID NO 60
<211> LENGTH: 19
<212> TYPE: DNA
<213> ORGANISM: artificial sequences
<220> FEATURE:
<223> OTHER INFORMATION: primers

<400> SEQUENCE: 60
tccctgttga ctggtcatt                                                19

<210> SEQ ID NO 61
<211> LENGTH: 21
<212> TYPE: DNA
<213> ORGANISM: Artificial Sequences
<220> FEATURE:
<223> OTHER INFORMATION: Primers

<400> SEQUENCE: 61
atgggcggaa tggtctcttt c                                             21

<210> SEQ ID NO 62
<211> LENGTH: 21
<212> TYPE: DNA
<213> ORGANISM: Artificial Sequences
<220> FEATURE:
<223> OTHER INFORMATION: Primers

<400> SEQUENCE: 62
tggggacctt gtcttcatca t                                             21

<210> SEQ ID NO 63
<211> LENGTH: 20
<212> TYPE: DNA
<213> ORGANISM: Artificial Sequences
<220> FEATURE:
<223> OTHER INFORMATION: Primers

<400> SEQUENCE: 63
atgatggctc aggtcccact                                               20

<210> SEQ ID NO 64
<211> LENGTH: 20
<212> TYPE: DNA
<213> ORGANISM: Artificial Sequences
<220> FEATURE:
<223> OTHER INFORMATION: Primers

<400> SEQUENCE: 64
cactggggca tcgtagttga                                               20

<210> SEQ ID NO 65
<211> LENGTH: 20
<212> TYPE: DNA
<213> ORGANISM: Artificial Sequences
<220> FEATURE:
<223> OTHER INFORMATION: Primers

<400> SEQUENCE: 65
tgaaatcacc gcagacgaca                                               20

<210> SEQ ID NO 66
<211> LENGTH: 20
<212> TYPE: DNA
<213> ORGANISM: Artificial Sequences
<220> FEATURE:
<223> OTHER INFORMATION: Primers
```

<400> SEQUENCE: 66
acacattcca ccaccagctt                                                    20

<210> SEQ ID NO 67
<211> LENGTH: 21
<212> TYPE: DNA
<213> ORGANISM: Artificial Sequences
<220> FEATURE:
<223> OTHER INFORMATION: Primers

<400> SEQUENCE: 67
ggaggtggtg atagccggta t                                                  21

<210> SEQ ID NO 68
<211> LENGTH: 21
<212> TYPE: DNA
<213> ORGANISM: Artificial Sequences
<220> FEATURE:
<223> OTHER INFORMATION: Primers

<400> SEQUENCE: 68
tgggtaatcc atagagccca g                                                  21

<210> SEQ ID NO 69
<211> LENGTH: 21
<212> TYPE: DNA
<213> ORGANISM: Artificial Sequences
<220> FEATURE:
<223> OTHER INFORMATION: Primers

<400> SEQUENCE: 69
agcttgcccg aattgtatgt g                                                  21

<210> SEQ ID NO 70
<211> LENGTH: 23
<212> TYPE: DNA
<213> ORGANISM: Artificial Sequences
<220> FEATURE:
<223> OTHER INFORMATION: Primers

<400> SEQUENCE: 70
tctgttgtga accatgtgac ttc                                                23

<210> SEQ ID NO 71
<211> LENGTH: 22
<212> TYPE: DNA
<213> ORGANISM: Artificial Sequences
<220> FEATURE:
<223> OTHER INFORMATION: Primers

<400> SEQUENCE: 71
ctccaagaat accaaagtgc ga                                                 22

<210> SEQ ID NO 72
<211> LENGTH: 21
<212> TYPE: DNA
<213> ORGANISM: Artificial Sequences
<220> FEATURE:
<223> OTHER INFORMATION: Primers

<400> SEQUENCE: 72
gcctgatgct ttatccccac a                                                  21

<210> SEQ ID NO 73
<211> LENGTH: 20

```
<212> TYPE: DNA
<213> ORGANISM: Artificial Sequences
<220> FEATURE:
<223> OTHER INFORMATION: Primers

<400> SEQUENCE: 73
gctctacacc tgcctcttcg                                              20

<210> SEQ ID NO 74
<211> LENGTH: 20
<212> TYPE: DNA
<213> ORGANISM: Artificial Sequences
<220> FEATURE:
<223> OTHER INFORMATION: Primers

<400> SEQUENCE: 74
cagccgagcc ttgtaagttc                                              20

<210> SEQ ID NO 75
<211> LENGTH: 21
<212> TYPE: DNA
<213> ORGANISM: Artificial Sequences
<220> FEATURE:
<223> OTHER INFORMATION: Primers

<400> SEQUENCE: 75
caaggccatc gactacatcc g                                            21

<210> SEQ ID NO 76
<211> LENGTH: 19
<212> TYPE: DNA
<213> ORGANISM: Artificial Sequences
<220> FEATURE:
<223> OTHER INFORMATION: Primers

<400> SEQUENCE: 76
caccacttcg ggtttcatg                                               19

<210> SEQ ID NO 77
<211> LENGTH: 18
<212> TYPE: DNA
<213> ORGANISM: Artificial Sequences
<220> FEATURE:
<223> OTHER INFORMATION: Primers

<400> SEQUENCE: 77
agcctttcgc gtctccat                                                18

<210> SEQ ID NO 78
<211> LENGTH: 20
<212> TYPE: DNA
<213> ORGANISM: Artificial Sequences
<220> FEATURE:
<223> OTHER INFORMATION: Primers

<400> SEQUENCE: 78
tgcataactt cgttccaggc                                              20

<210> SEQ ID NO 79
<211> LENGTH: 20
<212> TYPE: DNA
<213> ORGANISM: Artificial Sequences
<220> FEATURE:
<223> OTHER INFORMATION: Primers

<400> SEQUENCE: 79
```
gcccatgttg tacagcttcc                                                     20

<210> SEQ ID NO 80
<211> LENGTH: 20
<212> TYPE: DNA
<213> ORGANISM: Artificial Sequences
<220> FEATURE:
<223> OTHER INFORMATION: Primers

<400> SEQUENCE: 80
agtggcctca cagactccag                                                     20

<210> SEQ ID NO 81
<211> LENGTH: 19
<212> TYPE: DNA
<213> ORGANISM: Artificial Sequences
<220> FEATURE:
<223> OTHER INFORMATION: Primers

<400> SEQUENCE: 81
cagcacagca tcgtaccca                                                      19

<210> SEQ ID NO 82
<211> LENGTH: 21
<212> TYPE: DNA
<213> ORGANISM: Artificial Sequences
<220> FEATURE:
<223> OTHER INFORMATION: Primers

<400> SEQUENCE: 82
tcccaatgcc gttctcaaaa t                                                   21

<210> SEQ ID NO 83
<211> LENGTH: 19
<212> TYPE: DNA
<213> ORGANISM: Artificial Sequences
<220> FEATURE:
<223> OTHER INFORMATION: Primers

<400> SEQUENCE: 83
gcacgtccgg gaaatgaac                                                      19

<210> SEQ ID NO 84
<211> LENGTH: 20
<212> TYPE: DNA
<213> ORGANISM: Artificial Sequences
<220> FEATURE:
<223> OTHER INFORMATION: Primers

<400> SEQUENCE: 84
gcctcacact cgctgatctt                                                     20

<210> SEQ ID NO 85
<211> LENGTH: 20
<212> TYPE: DNA
<213> ORGANISM: Artificial Sequences
<220> FEATURE:
<223> OTHER INFORMATION: Primers

<400> SEQUENCE: 85
gtttatcccc cgattcaggt                                                     20

<210> SEQ ID NO 86
<211> LENGTH: 20
<212> TYPE: DNA
<213> ORGANISM: Artificial Sequences

```
<220> FEATURE:
<223> OTHER INFORMATION: Primers

<400> SEQUENCE: 86
ttactcagtg gaacaccgcc                                              20

<210> SEQ ID NO 87
<211> LENGTH: 20
<212> TYPE: DNA
<213> ORGANISM: Artificial Sequences
<220> FEATURE:
<223> OTHER INFORMATION: Primers

<400> SEQUENCE: 87
agtgaacact ccttcggtgc                                              20

<210> SEQ ID NO 88
<211> LENGTH: 20
<212> TYPE: DNA
<213> ORGANISM: Artificial Sequences
<220> FEATURE:
<223> OTHER INFORMATION: Primers

<400> SEQUENCE: 88
tgacagggct ttctggtctt                                              20

<210> SEQ ID NO 89
<211> LENGTH: 20
<212> TYPE: DNA
<213> ORGANISM: Artificial Sequences
<220> FEATURE:
<223> OTHER INFORMATION: Primers

<400> SEQUENCE: 89
agagccccat ctgtcctctc                                              20

<210> SEQ ID NO 90
<211> LENGTH: 22
<212> TYPE: DNA
<213> ORGANISM: Artificial Sequences
<220> FEATURE:
<223> OTHER INFORMATION: Primers

<400> SEQUENCE: 90
actggtagtc tgcaaaacca aa                                           22

<210> SEQ ID NO 91
<211> LENGTH: 21
<212> TYPE: DNA
<213> ORGANISM: Artificial Sequences
<220> FEATURE:
<223> OTHER INFORMATION: Primers

<400> SEQUENCE: 91
tgttcctctt aatcctgccc a                                            21

<210> SEQ ID NO 92
<211> LENGTH: 21
<212> TYPE: DNA
<213> ORGANISM: Artificial Sequences
<220> FEATURE:
<223> OTHER INFORMATION: Primers

<400> SEQUENCE: 92
ccaacctgca caagttccct t                                            21
```

<210> SEQ ID NO 93
<211> LENGTH: 18
<212> TYPE: DNA
<213> ORGANISM: Artificial Sequences
<220> FEATURE:
<223> OTHER INFORMATION: Primers

<400> SEQUENCE: 93
tgaagcaggg ccactctc                                                    18

<210> SEQ ID NO 94
<211> LENGTH: 18
<212> TYPE: DNA
<213> ORGANISM: Artificial Sequences
<220> FEATURE:
<223> OTHER INFORMATION: Primers

<400> SEQUENCE: 94
gacaccacct gcatggct                                                    18

<210> SEQ ID NO 95
<211> LENGTH: 22
<212> TYPE: DNA
<213> ORGANISM: Artificial Sequences
<220> FEATURE:
<223> OTHER INFORMATION: Primers

<400> SEQUENCE: 95
gatttacgca cgatgacaca gt                                               22

<210> SEQ ID NO 96
<211> LENGTH: 22
<212> TYPE: DNA
<213> ORGANISM: Artificial Sequences
<220> FEATURE:
<223> OTHER INFORMATION: Primers

<400> SEQUENCE: 96
acctgcaaag acattagaca gc                                               22

<210> SEQ ID NO 97
<211> LENGTH: 21
<212> TYPE: DNA
<213> ORGANISM: Artificial Sequences
<220> FEATURE:
<223> OTHER INFORMATION: Primers

<400> SEQUENCE: 97
gtgaacccga caacttccga a                                                21

<210> SEQ ID NO 98
<211> LENGTH: 20
<212> TYPE: DNA
<213> ORGANISM: Artificial Sequences
<220> FEATURE:
<223> OTHER INFORMATION: Primers

<400> SEQUENCE: 98
tgccaggcaa gctgaaactc                                                  20

<210> SEQ ID NO 99
<211> LENGTH: 23
<212> TYPE: DNA
<213> ORGANISM: Artificial Sequences
<220> FEATURE:
<223> OTHER INFORMATION: Primers

<400> SEQUENCE: 99
ttaaaaacct ggatcggaac caa                                              23

<210> SEQ ID NO 100
<211> LENGTH: 23
<212> TYPE: DNA
<213> ORGANISM: Artificial Sequences
<220> FEATURE:
<223> OTHER INFORMATION: Primers

<400> SEQUENCE: 100
gcattagctt cagatttacg ggt                                              23

<210> SEQ ID NO 101
<211> LENGTH: 19
<212> TYPE: DNA
<213> ORGANISM: Artificial Sequences
<220> FEATURE:
<223> OTHER INFORMATION: Primers

<400> SEQUENCE: 101
cctgtagccc acgtcgtag                                                   19

<210> SEQ ID NO 102
<211> LENGTH: 22
<212> TYPE: DNA
<213> ORGANISM: Artificial Sequences
<220> FEATURE:
<223> OTHER INFORMATION: Primers

<400> SEQUENCE: 102
gggagtagac aaggtacaac cc                                               22

<210> SEQ ID NO 103
<211> LENGTH: 21
<212> TYPE: DNA
<213> ORGANISM: Artificial Sequences
<220> FEATURE:
<223> OTHER INFORMATION: Primers

<400> SEQUENCE: 103
gtcccagaca tcagggagta a                                                21

<210> SEQ ID NO 104
<211> LENGTH: 21
<212> TYPE: DNA
<213> ORGANISM: Artificial Sequences
<220> FEATURE:
<223> OTHER INFORMATION: Primers

<400> SEQUENCE: 104
tcggatactt cagcgtcagg a                                                21

<210> SEQ ID NO 105
<211> LENGTH: 28
<212> TYPE: DNA
<213> ORGANISM: Artificial Sequences
<220> FEATURE:
<223> OTHER INFORMATION: Primers

<400> SEQUENCE: 105
gcttgctggt gaaaaggacc tctcgaag                                         28

<210> SEQ ID NO 106

```
<211> LENGTH: 30
<212> TYPE: DNA
<213> ORGANISM: Artificial Sequences
<220> FEATURE:
<223> OTHER INFORMATION: Primers

<400> SEQUENCE: 106
ccctgaagta ctcattatag tcaagggcat                                    30
```